United States Patent
Thim et al.

(10) Patent No.: US 7,411,039 B2
(45) Date of Patent: Aug. 12, 2008

(54) GLP-2 COMPOUNDS, FORMULATIONS, AND USES THEREOF

(75) Inventors: Lars Thim, Gentofte (DK); Susanne Bang, Bagsvaerd (DK); Niels Christian Kaarsholm, Vanloese (DK); Anette Sams Nielsen, Bagsvaerd (DK); Nils Langeland Johansen, Copenhagen OE. (DK); Kjeld Madsen, Vaerlose (DK); Magali Zundel, Soeborg (DK); Peter Thygesen, Copenhagen OE. (DK); Birgitte Michelsen, Denmark (DK)

(73) Assignee: Novo Nordisk A/S, Bagsvaerd (DK)

(*) Notice: Subject to any disclaimer, the term of this patent is extended or adjusted under 35 U.S.C. 154(b) by 479 days.

(21) Appl. No.: 10/685,368

(22) Filed: Oct. 14, 2003

(65) Prior Publication Data

US 2004/0122210 A1 Jun. 24, 2004

Related U.S. Application Data

(60) Provisional application No. 60/434,562, filed on Dec. 19, 2002, provisional application No. 60/434,560, filed on Dec. 19, 2002, provisional application No. 60/420,581, filed on Oct. 23, 2002, provisional application No. 60/426,273, filed on Nov. 14, 2002.

(30) Foreign Application Priority Data

| Oct. 14, 2002 | (DK) | 2002 01574 |
| Oct. 14, 2002 | (DK) | 2002 01778 |
| Oct. 15, 2002 | (DK) | 2002 01780 |

(51) Int. Cl.
*A61K 38/26* (2006.01)

(52) U.S. Cl. ............... 530/308; 530/325; 514/2; 514/12

(58) Field of Classification Search ............ None
See application file for complete search history.

(56) References Cited

U.S. PATENT DOCUMENTS

| 5,470,582 | A | 11/1995 | Supersaxo et al. ......... 424/489 |
| 5,512,549 | A | 4/1996 | Chen et al. ............... 514/12 |
| 5,624,894 | A | 4/1997 | Bodor .................... 514/2 |
| 5,789,379 | A | 8/1998 | Drucker et al. ........... 514/12 |
| 5,834,428 | A | 11/1998 | Drucker ................. 514/12 |
| 5,869,602 | A | 2/1999 | Jonassen et al. .......... 530/300 |
| 5,912,229 | A | 6/1999 | Thim et al. ............. 514/12 |
| 5,952,301 | A | 9/1999 | Drucker ................. 514/12 |
| 5,990,077 | A | 11/1999 | Drucker ................. 514/2 |
| 5,994,500 | A | 11/1999 | Drucker et al. ........... 530/324 |
| 6,051,557 | A | 4/2000 | Drucker ................. 514/12 |
| 6,184,201 | B1 | 2/2001 | Drucker et al. ........... 514/12 |
| 6,297,214 | B1 | 10/2001 | Drucker ................. 514/12 |
| 6,489,295 | B1 | 12/2002 | Drucker et al. ........... 514/12 |
| 6,586,399 | B1 | 7/2003 | Drucker ................. 514/12 |
| 2001/0016643 | A1 | 8/2001 | Jonassen et al. .......... 530/300 |
| 2001/0021767 | A1 | 9/2001 | Drucker et al. ........... 530/320 |
| 2001/0027180 | A1 | 10/2001 | Isaacs .................. 514/12 |
| 2002/0025933 | A1 | 2/2002 | Knudsen et al. ........... 514/12 |
| 2003/0040478 | A1 | 2/2003 | Drucker et al. ........... 514/12 |
| 2003/0109449 | A1 | 6/2003 | Drucker et al. ........... 514/12 |
| 2003/0158101 | A1 | 8/2003 | Drucker ................. 514/12 |
| 2003/0162703 | A1 | 8/2003 | Drucker et al. ........... 514/12 |
| 2004/0127418 | A1 | 7/2004 | Knudsen et al. |

FOREIGN PATENT DOCUMENTS

| CA | 2137206 | 12/1994 |
| EP | 0891378 B1 | 2/1997 |
| WO | WO 91/11457 A1 | 8/1991 |
| WO | WO 95/07931 A1 | 3/1995 |
| WO | 96/29342 | 9/1996 |
| WO | WO 96/32414 A1 | 10/1996 |
| WO | WO 97/31943 A1 | 9/1997 |
| WO | WO 97/39031 A1 | 10/1997 |
| WO | WO 98/03547 | 1/1998 |
| WO | WO 98/03547 A1 | 1/1998 |
| WO | 98/08871 | 3/1998 |
| WO | WO 98/08872 A1 | 3/1998 |
| WO | WO 98/25644 A1 | 6/1998 |
| WO | WO 98/52600 A1 | 11/1998 |
| WO | WO 99/43361 A1 | 9/1999 |
| WO | WO 99/58144 A1 | 11/1999 |
| WO | WO 01/41779 A2 | 6/2001 |
| WO | WO 01/49314 A2 | 7/2001 |
| WO | WO 01/49314 A3 | 7/2001 |
| WO | WO 0149314 A2 | 7/2001 |
| WO | WO 0149314 A3 | 7/2001 |

(Continued)

OTHER PUBLICATIONS

Clodfelter et al., Pharmaceutical Res. 15(2):254-262 (1998).
Shennan et al., Molecular and Cellular Endocrinology: vol. 67; pp. 93-99 (1989).
Watanabe et al., Biochem and Biophys Res. Com, vol. 152 (3); pp. 1038-1044 (May 16, 1988).
Lund et al., Digestion; pp. 371-373 (Nov.-Dec. 1993).
Orskov et al., Diabetologia, vol. 30; pp. 874-881 (1987).
Orskov et al., FEBS Letters, vol. 247 (2); pp. 193-196 (Apr. 1989).
George et al., FEBS Letters, vol. 192 (2); pp. 275-278 (1985).
Hoosein et al., FEBS Letters, vol. 178 (1); pp. 83-86 (Dec. 1984).
Buhl et al., Journ of Biol Chem, vol. 263 (18); pp. 8621-8624 (Jun. 25, 1998).

(Continued)

*Primary Examiner*—Anish Gupta
(74) *Attorney, Agent, or Firm*—Len S. Smith

(57) ABSTRACT

The present invention relates to novel human glucagon-like peptide-2 (GLP-2) peptides and human glucagon-like peptide-2 derivatives which have a protracted profile of action as well as polynucleotide constructs encoding such peptides, vectors and host cells comprising and expressing the polynucleotide, pharmaceutical compositions, uses and methods of treatment.

31 Claims, 12 Drawing Sheets

FOREIGN PATENT DOCUMENTS

| WO | 02/066511 A2 | 8/2002 |
|----|----|----|
| WO | 02/066511 A3 | 8/2002 |
| WO | WO 02/066062 A2 | 8/2002 |
| WO | WO 02/066062 A3 | 8/2002 |

OTHER PUBLICATIONS

Lee et al., Journ of Biol Chem, vol. 267 (15); pp. 10705-10708 (May 1992).
Orskov et al., Scand J. Clin. Lab. Invest, vol. 47 (2); pp. 165-174 (Apr. 1987).
Barragan et al., Am. J. of Physiol, vol. 266 (3 Part 1); pp. E459-E466 (Mar. 1994).
Brubaker et al., Endocrin., vol. 128 (6); pp. 3175-3182 (1991).
Calvo et al., J. Neurochem, vol. 64 (1); pp. 299-306 (Jan. 1995).
Drucker, Pancreas, vol. 5 (4); pp. 484-488 (1990).
Mojsov et al., Journ of Biol. Chem., vol. 261 (25); pp. 11880-11889 (Sep. 5, 1986).
Orskov et al., Endocrin., vol. 119 (4); pp. 1467-1475 (1986).
Madsen et al., Endocrin., vol. 133 (5); pp. 2022-2030 (1993).
Siegel et al., Reg. Peptides, vol. 79; pp. 93-102 (1999).
Gallwitz et al., Reg. Peptides, vol. 86; pp. 103-111 (2000).
Turton et al., Nature, vol. 379; pp. 69-71 (1996).
Flint et al., J. Clin. Invest., vol. 101 (3); pp. 515-520 (1998).
Gutzwiller et al., Gut, vol. 44; pp. 81-86 (1999).
Naslund et al., Int. J. of Obesity, vol. 23; pp. 304-311 (1999).
Sorensen et al., Int. J. of Obesity., vol. 27; pp. 450-456 (2003).
Drucker et al., J. Nature Biotech, vol. 15; pp. 673-677 (1997).
Nishi et al., Mol. Endocrin., vol. 4; pp. 1192-1198 (1990).
Mentlein et al., Eur. J. Biochem., vol. 214; pp. 829-835 (1993).
Peninsula Laboratories, Inc. Catalog 1993-1994.
Demuth et al., Dipeptidy Peptidase IV (CD26) in Metab. Immune Resp., Chptr 1, pp. 1-35 (Springer, RG Landis Co. Austin TX) (1995).
Bongers et al., Biochim et Biophys. Acta, vol. 1122; pp. 147-153 (1992).
Gallwitz et al., Eur. J. Biochem., vol. 225; pp. 1151-1156 (1994).
Deacon et al., Diabetes, vol. 44; pp. 1126-1131 (1995).
Kieffer et al., Endocrin., vol. 136 (8); pp. 3585-3596 (1995).
Drucker et al., Proc. Natl. Acad. Sci. USA, vol. 93; pp. 7911-7916 (1996).
Drucker et al., , Intestinal Growth Factors; pp. G1252-G1262.
U.S. Appl. No. 08/631,273, filed Apr. 12, 1996, Drucker et al.
Lund et al., Digestion., vol. 46 (suppl. 2); pp. 66-73 (1990).
Ehrlich et al., Reg. of Proglucagon Gene Express.; pp. E662-E671.
Orskov et al., Abstract P6.
Tang-Christiansen et al., Nature Medicine, vol. 6 (7), pp. 802-807 (Jul. 2000).
Substantive Arguments to Date from Opposition to European Patent 0 891 378.
Drucker et al., Proc. Natl. Acad. Sci. USA, vol. 93, pp. 7911-7916 (1996).

Figure 3.

| Source | GLP-2 sequence | Accession no./Ref. no. |
| --- | --- | --- |
| Human | HADGSFSDEMNTILDNLAARDFINWLIQTKITD | P01275 |
| Golden hamster | HADGSFSDEMNTILDSLATRDFINWLIQTKITD | P0127 |
| Rat | HADGSFSDEMNTILDNLATRDFINWLIQTKITD | P06883 |
| Guinea-pig | HADGSFSDEMNTILDNLATRDFINWLIQTKITD | P05110 |
| Mouse | HADGSFSDEMSTILDNLATRDFINWLIQTKITD | P55095 |
| Bovine | HADGSFSDEMNTVLDSLATRDFINWLLQTKITD | P01272 |
| Pig | HADGSFSDEMNTVLDNLATRDFINWLLHTKITD | P01274 |
| Degu (rodent) | HADGSFSDEMNTVLDHLATKDFINWLIQTKITD | P22890 |
| Chicken | HADGTFTSDINKILDDMAAKEFLKWLINTKVTQ | I51301 |
| Frog | HADGSFTSDFNKALDIKAAQEFLDWIINTPVKE | Ref. 37 |
| Salamander | HADGSFTSDINKVLDTIAAKEFLNWLISTKVTE | AAB37529 |
| Trout | HVDGSFTSDVNKVLDSLAAKEYLLWVMTSKTSG | Ref. 37 |

Figure 4.

| Tissue | F1 quantitation, copies per μg total RNA | β-Actin quantitation, copies per μg total RNA | GLP-2R/-actin, ratio |
|---|---|---|---|
| Jejunum | 11,900 | 15,500,000 | $76.8 \times 10^{-5}$ |
| Duodenum | 9,150 | 85,700,000 | $10.7 \times 10^{-5}$ |
| Ileum | 7,490 | 51,400,000 | $14.6 \times 10^{-5}$ |
| Colon | 4,150 | 19,800,000 | $21.0 \times 10^{-5}$ |
| Stomach | 1,530 | 23,600,000 | $6.48 \times 10^{-5}$ |
| Brain | <600 | 40,600,000 | $<1.48 \times 10^{-5}$ |
| Heart | <600 | 6,600,000 | $<9.09 \times 10^{-5}$ |
| Kidney | <600 | 14,900,000 | $<4.03 \times 10^{-5}$ |
| Liver | <600 | 16,700,000 | $<3.59 \times 10^{-5}$ |
| Lung | <600 | 38,500,000 | $<1.56 \times 10^{-5}$ |
| Muscle | <600 | 4,600,000 | $<13.0 \times 10^{-5}$ |
| Spleen | <600 | 44,800,000 | $<1.34 \times 10^{-5}$ |

Figure 6.
a) Example of the use of a β-alanine spacer on a lysine residue:
Lys(3-(hexadecanoylamino)propionyl):
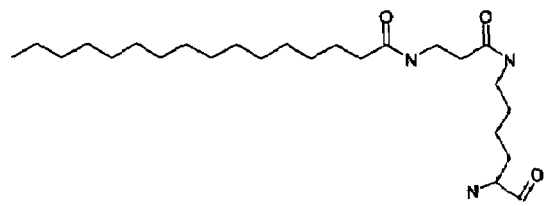
b) Example of the use of a γ-glutamic acid spacer on a lysine residue:
Lys((S)-4-carboxy-4-(hexadecanoylamino)butanoyl):
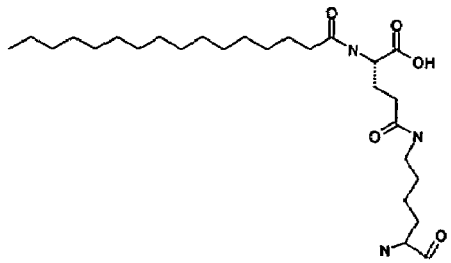
c) Example of the use of a GABA spacer on a lysine residue:
Lys(4-(hexadecanoylamino)butanoyl):
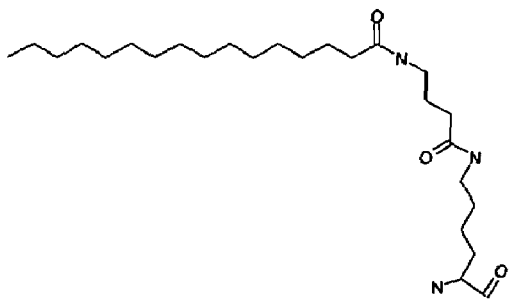

Figure 9.
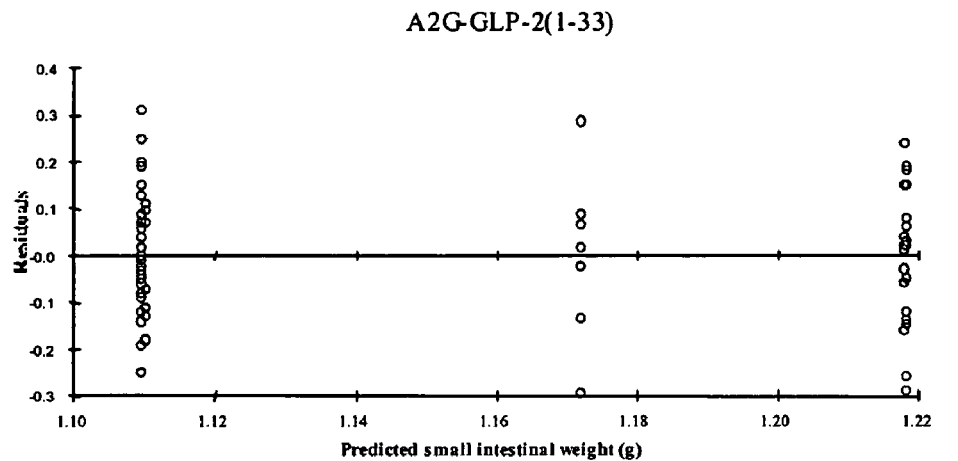
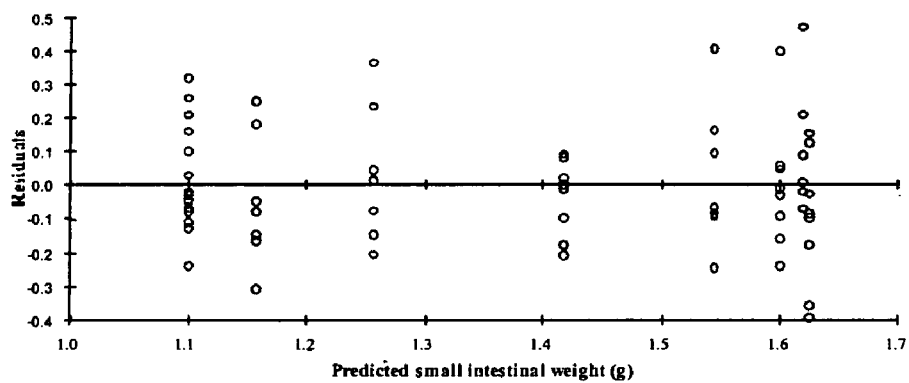
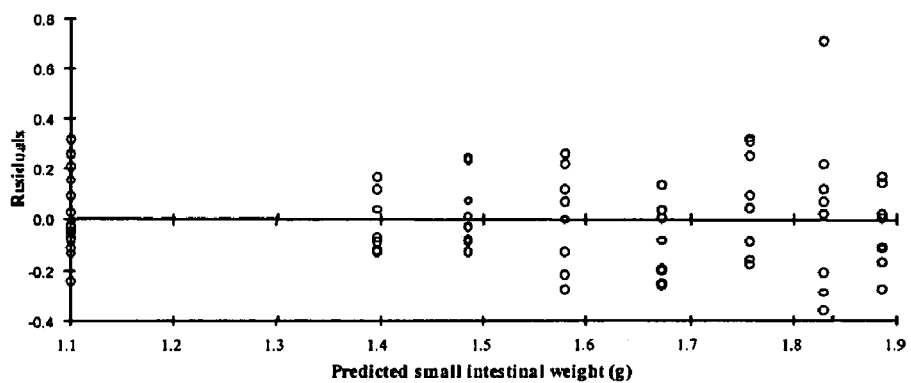

Figure 12.

SEQ ID NO. 1 (The amino acid sequence of native human GLP-2):

H A D G S F S D E M N T I L D N L A A R D F I N W L I Q T K I T D

SEQ ID NO. 2 (GLP-2 peptides according to formula I):

His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-Arg-$X^{21}$-Phe-Ile-$X^{24}$-Trp-Leu-Ile-$X^{28}$-Thr-Arg-Ile-Thr-$X^{33}$ wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{21}$ is Asp, or Lys; $X^{24}$ is Asn, or Lys; $X^{28}$ is Gln, or Lys; $X^{33}$ is Asp, Glu, or Lys.

SEQ ID NO. 3 (GLP-2 peptides according to formula II):

His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-$X^{20}$-$X^{21}$-Phe-Ile-$X^{24}$-Trp-Leu-Ile-$X^{28}$-Thr-$X^{30}$-Ile-Thr-$X^{33}$ wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{20}$ is Arg, or Lys; $X^{21}$ is Asp, or Lys; $X^{24}$ is Asn, or Lys; $X^{28}$ is Gln, or Lys; $X^{30}$ is Arg, or Lys; $X^{33}$ is Asp, Glu, or Lys.

GLP-2 COMPOUNDS, FORMULATIONS, AND USES THEREOF

CROSS-REFERENCE TO RELATED APPLICATIONS

This application claims priority under 35 U.S.C. 119 of Danish applications nos. PA 2002 01574 filed on Oct. 14, 2002; PA 2002 01780 filed on Nov. 19, 2002 and PA 2002 01778 filed on Nov. 19, 2002 and U.S. applications No. 60/434,562 filed on Dec. 19, 2002; 60/434,560 filed on Dec. 19, 2002; 60/420,581 filed on Oct. 23, 2002 and 60/426,273 filed on Nov. 14, 2002, the contents of which are fully incorporated herein by reference.

FIELD OF THE INVENTION

The present invention relates to novel human glucagon-like peptide 2 (GLP-2) peptides and derivatives thereof which have a protracted profile of action. The invention further relates to methods of making and using these GLP-2 peptides and derivatives as well as polynucleotide constructs encoding such GLP-2 peptides and host cells comprising and expressing the GLP-2 peptides, pharmaceutical formulations, methods for preparing said formulations, uses and methods of treatment.

BACKGROUND OF THE INVENTION

Glucagon-like peptide 2 (GLP-2) is a 33 amino acid residue peptide produced in intestinal L-cells and released following nutrient intake. The amino acid sequence of the human GLP-2 peptide is given in FIG. 1.

The GLP-2 peptide is a product of the proglucagon gene. Proglucagon is expressed mainly in the pancreas and the intestine and to some extent in specific neurons located in the brain. The posttranslational processing of proglucagon is however different in pancreas and intestine (FIG. 2). In the pancreas proglucagon is processed mainly to Glucagon Related Pancreatic Polypeptide (GRPP), Glucagon and Major Proglucagon Fragment. In contrast to this the processing in the intestine results in Glicentin, Glucagon-Like Peptide 1 (GLP-1) and Glucagon-Like Peptide 2 (GLP-2).

The GLP-2 peptide is rather well conserved between species although sequence differences exists (FIG. 3). The pig GLP-2 peptide for example has 4 substitutions as compared to the human GLP-2. Interestingly the mouse GLP-2 has only two substitutions compared to the human GLP-2.

GLP-2 is secreted from the L-cells in the small and large intestine. This secretion is regulated by nutrient intake. The plasma concentration of GLP-2 in normal fasting subjects is around 15 pM increasing to around 60 pM after a mixed meal.

The actions of GLP-2 are transduced by a recently cloned glucagon-like peptide-2 receptor. The GLP-2 receptor represents a new member of the G protein-coupled 7TM receptor superfamily. The GLP-2R is expressed in a highly tissue-specific manner predominantly in the gastrointestinal tract (FIG. 4) and GLP-2R activation is coupled to increased adenylate cyclase activity. Cells expressing the GLP-2R responds to GLP-2, but not to other peptide of the glucagon family (Glucagon, GLP-1 and GIP).

In the rat the GLP-2R has also been reported to be expressed in the brain or more specific the dorsomedial hypothalamic nucleus. This part of the brain is normally thought to be involved in feeding behaviour and it has been shown that GLP-2 inhibits food intake when injected directly into the brain.

Induction of intestinal epithelial proliferation by GLP-2 was demonstrated (Drucker, D. J. et al (1996) Proc. Natl. Acad. Sci. USA 93: 7911-7916) and treatment of gastrointestinal diseases by cells grown in medium containing GLP-2 was disclosed (Drucker, D. J and Keneford, J. R., WO 96/32414).

WO 97/31943 relates to GLP-2 peptide analogs and the use of certain GLP-2 peptide analogs for appetite suppression or sateity induction.

WO 98/08872 Relates to GLP-2 derivatives comprising a lipophilic substituent.

WO 96/32414 and WO 97/39031 relates to specific GLP-2 peptide analogs.

WO 98/03547 relates to specific GLP-2 peptide analogs, which exhibit antagonist activity While much attention has been focused on the pharmacological properties of GLP-2 compounds, hitherto little is known about their physico-chemical and solution structural properties. Such knowledge is a prerequisite for rational handling during e.g. production, purification and formulation work and is eventually important for understanding of the structural basis for the protraction mechanism.

It is an important technical challenge to ensure prolonged stability during storage (shelf life) of many protein based drug products due to the inherent lability of macromolecules. Hence, proteins are sensitive to both chemical and physical degradation unlike many small molecules. Chemical degradation involves covalent bonds, such as hydrolysis, racemization, oxidation or crosslinking. Physical degradation involves conformational changes relative to the native structure, which includes loss of higher order structure, aggregation, precipitation or adsorption to surfaces. GLP-2 is known to be prone to instability due to aggregation. Both degradation pathways may ultimately lead to loss of biological activity of the protein drug.

GLP-2 and analogs of GLP-2 and fragments thereof are potentially useful i.a. in the treatment of gastrointestinal diseases. However, solubility limitations and the low stability against the actions of endogenous diaminopeptidyl peptidase limits the usefulness of these compounds, and thus there still is a need for improvements in this field.

In WO 99/43361 are disclosed certain pharmaceutical formulations comprising GLP-2 having a lipophilic substituent.

In WO 01/49314 are disclosed a formulations comprising GLP-2 or GLP-2 analogs in a physiological buffer containing L-histidine and a bulk agent selected from a group consisting of mannitol and sucrose, at pH 5.5 to 7.9.

GLP-2 peptides and derivatives thereof are useful in the treatment of gastrointestinal disorders. However, the high clearance limits the usefulness of these compounds, and thus there still is a need for improvements in this field. Accordingly, it is an object of the present invention to provide peptides of GLP-2 and derivatives thereof which have a protracted profile of action relative to native GLP-2, while still retaining the GLP-2 activity. It is a further object of the invention to provide a pharmaceutical composition comprising a compound according to the invention and to use a compound of the invention to provide such a composition. Also, it is an object of the present invention to provide a method of treating gastrointestinal disorders.

SUMMARY OF THE INVENTION

It has now been shown that GLP-2 derivatives of the present invention exerts a trophic effects on the small and large intestine via stimulation of cell proliferation and inhibition of apoptosis. GLP-2 derivatives of the present invention may also stimulate enterocyte glucose transport, reduce intestinal permeability and inhibit gastric emptying and gastric acid secretion.

In its broadest aspect, the present invention relates to derivatives of GLP-2 peptides. The derivatives according to the invention have interesting pharmacological properties, in particular they have a more protracted profile of action than the parent GLP-2 peptides.

The term "parent GLP-2 peptide" as used herein refers to the amino acid sequence backbone of a GLP-2 derivative.

A simple system is used in the following to describe peptides, fragments, analogs and derivatives of GLP-2. Thus, for example, R20K-GLP-2(1-31) designates a fragment of GLP-2 formally derived from GLP-2 by deleting the amino acid residues at position 32 and 33 of SEQ ID NO:1 and substituting the naturally occurring amino acid residue arginine at position 20 of SEQ ID NO:1 by a lysine. Similarly, R20K($N^\epsilon$-tetradecanoyl)/K30R-GLP-2(1-33) designates a derivative of a GLP-2 peptide analog formally derived from GLP-2 by exchange of the naturally occurring amino acid residue lysine in position 30 of SEQ ID NO:1 with an arginine residue and exchange of the naturally occurring amino acid residue arginine in position 20 of SEQ ID NO:1 with a lysine residue and tetradecanoylation of the $\epsilon$-amino group of the lysine residue in position 20 relative to the amino acid sequence of SEQ ID NO:1.

Similarly, L17K(3-(hexadecanoylamino)propionyl)/K30R-GLP-2(1-33) designates a derivative of a GLP-2 peptide analog formally derived from GLP-2 by exchange of the naturally occurring amino acid residue lysine in position 30 of SEQ ID NO:1 with an arginine residue and exchange of the naturally occurring amino acid residue leucine in position 17 of SEQ ID NO:1 with a lysine residue and hexadecanoylation of the $\epsilon$-amino group of the lysine residue in position 17 relative to the amino acid sequence of SEQ ID NO:1 by means of the spacer β-alanine (FIGS. 5 and 6).

In a first aspect, the invention relates to a GLP-2 peptide comprising the amino acid sequence of formula I;

His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-Arg-$X^{21}$-Phe-Ile-$X^{24}$-Trp-Leu-Ile-$X^{28}$-Thr-Arg-Ile-Thr-$X^{33}$    (formula I);

or a fragment thereof; wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{21}$ is Asp, or Lys; $X^{24}$ is Asn, or Lys; $X^{28}$ is Gln, or Lys; $X^{33}$ is Asp, Glu, or Lys.

In a second aspect, the invention relates to a polynucleotide construct encoding a GLP-2 peptide comprising the amino acid sequence of formula I;

His-$X^2$-$X^3$-Gly-$X^5$-Phe-$X^7$-$X^8$-$X^9$-$X^{10}$-$X^1$-$X^{12}$-$X^{13}$-$X^{14}$-$X^{15}$-$X^{16}$-$X^{17}$-$X^{18}$-Ala-Arg-$X^{21}$-Phe-Ile-$X^{24}$-Trp-Leu-Ile-$X^{28}$-Thr-Arg-Ile-Thr-$X^{33}$    (formula I);

or a fragment thereof; wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{21}$ is Asp, or Lys; $X^{24}$ is Asn, or Lys; $X^{28}$ is Gln, or Lys; $X^{33}$ is Asp, Glu, or Lys.

In a third aspect, the invention relates to a host cell comprising a polynucleotide construct encoding a GLP-2 peptide comprising the amino acid sequence of formula I;

His-$X^2$-$X^3$-Gly-$X^5$-Phe-$X^7$-$X^8$-$X^9$-$X^{10}$-$X^1$-$X^{12}$-$X^{13}$-$X^{14}$-$X^{15}$-$X^{16}$-$X^{17}$-$X^{18}$-Ala-Arg-$X^{21}$-Phe-Ile-$X^{24}$-Trp-Leu-Ile-$X^{28}$-Thr-Arg-Ile-Thr-$X^{33}$    (formula I);

or a fragment thereof; wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{21}$ is Asp, or Lys; $X^{24}$ is Asn, or Lys; $X^{28}$ is Gln, or Lys; $X^{33}$ is Asp, Glu, or Lys. In one embodiment the host cell is a eukaryotic cell. In one embodiment the host cell is a yeast cell.

In a further aspect, the invention relates to a GLP-2 derivative comprising a GLP-2 peptide, wherein a lipophilic substituent is attached to one or more amino acid residues at a position relative to the amino acid sequence of SEQ ID NO:1 selected from the list consisting of S5, S7, D8, E9, M10, N11, T12, I13, L14, D15, N16, L17, A18, D21, N24, and Q28 with the proviso that said lipophilic substituent is not attached at the N-terminal amino acid residue or the C-terminal amino acid residue of said GLP-2 peptide. In one embodiment a lipophilic substituent is attached to an amino acid residues at the position S5 relative to the amino acid sequence of SEQ ID NO:1. In one embodiment a lipophilic substituent is attached to an amino acid residues at the position S7 relative to the amino acid sequence of SEQ ID NO:1. In one embodiment a lipophilic substituent is attached to an amino add residues at the position D8 relative to the amino acid sequence of SEQ ID NO:1. In one embodiment a lipophilic substituent is attached to an amino acid residues at the position E9 relative to the amino acid sequence of SEQ ID NO:1. In one embodiment a lipophilic substituent is attached to an amino acid residues at the position M10 relative to the amino acid sequence of SEQ ID NO:1. In one embodiment a lipophilic substituent is attached to an amino acid residues at the position N11 relative to the amino acid sequence of SEQ ID NO:1. In one embodiment a lipophilic substituent is attached to an amino acid residues at the position T12 relative to the amino acid sequence of SEQ ID NO:1. In one embodiment a lipophilic substituent is attached to an amino acid residues at the position I13 relative to the amino acid sequence of SEQ ID NO:1. In one embodiment a lipophilic substituent is attached to an amino acid residues at the position L14 relative to the amino acid sequence of SEQ ID NO:1. In one embodiment a lipophilic substituent is attached to an amino acid residues at the position D15 relative to the amino acid sequence of SEQ ID NO:1. In one embodiment a lipophilic substituent is attached to an amino acid residues at the position N16 relative to the amino acid sequence of SEQ ID NO:1. In one embodiment a lipophilic substituent is attached to an amino acid residues at the position L17 relative to the amino acid sequence of SEQ ID NO:1. In one embodiment a lipophilic substituent is attached to an amino acid residues at the position A18 relative to the amino acid sequence of SEQ ID NO:1. In one embodiment a lipophilic substituent is attached to an amino acid residues at the position D21 relative to the amino acid sequence of SEQ ID NO:1. In one embodiment a lipophilic substituent is attached to an amino acid residues at the position N24 relative to the amino acid sequence of SEQ ID NO:1. In one embodiment a lipophilic substituent is attached to an amino acid residues at the position Q28 relative to the amino acid sequence of SEQ ID NO:1. It is to be understood that an amino acid residues at the position relative to the amino acid sequence of SEQ ID NO:1 may be any amino acid residue and not only the amino acid residue naturally present at that position. In one embodiment the lipophilic substituent is attached to a lysine.

In a further aspect, the invention relates to a pharmaceutical composition comprising a GLP-2 derivative comprising a GLP-2 peptide, wherein a lipophilic substituent is attached to one or more amino acid residues at a position relative to the amino acid sequence of SEQ ID NO:1 selected from the list consisting of S5, S7, D8, E9, M10, N11, T12, I13, L14, D15, N16, L17, A18, D21, N24, and Q28 with the proviso that said lipophilic substituent is not attached at the N-terminal amino acid residue or the C-terminal amino acid residue of said GLP-2 peptide.

In a further aspect, the invention relates to the use of a GLP-2 derivative comprising a GLP-2 peptide, wherein a lipophilic substituent is attached to one or more amino acid residues at a position relative to the amino acid sequence of SEQ ID NO:1 selected from the list consisting of S5, S7, D8, E9, M10, N1, T12, I13, L14, D15, N16, L17, A18, D21, N24, and Q28 with the proviso that said lipophilic substituent is not attached at the N-terminal amino acid residue or the C-terminal amino acid residue of said GLP-2 peptide; for the preparation of a medicament.

In a further aspect, the invention relates to the use of a GLP-2 derivative comprising a GLP-2 peptide, wherein a lipophilic substituent is attached to one or more amino acid residues at a position relative to the amino acid sequence of SEQ ID NO:1 selected from the list consisting of S5, S7, D8, E9, M10, N11, T12, I13, L14, D15, N16, L17, A18, D21, N24, and Q28 with the proviso that said lipophilic substituent is not attached at the N-terminal amino acid residue or the C-terminal amino acid residue of said GLP-2 peptide; for the preparation of a medicament with protracted effect.

In a further aspect, the invention relates to the use of a GLP-2 derivative comprising a GLP-2 peptide, wherein a lipophilic substituent is attached to one or more amino acid residues at a position relative to the amino acid sequence of SEQ ID NO:1 selected from the list consisting of S5, S7, D8, E9, M10, N11, T12, I13, L14, D15, N16, L17, A18, D21, N24, and Q28 with the proviso that said lipophilic substituent is not attached at the N-terminal amino acid residue or the C-terminal amino acid residue of said GLP-2 peptide; for the preparation of a medicament for the treatment of small bowel syndrome, Inflammatory bowel syndrome, Crohns disease, colitis including collagen colitis, radiation colitis, ulcerative colitis chronic radiation enteritis, non-tropical (gluten intolerance) and tropical sprue, Coeliac disease (gluten sensitive enteropathy), damaged tissue after vascular obstruction or trauma, diarrhea e.g. tourist diarrhea and post-infective diarrhea, chronic bowel dysfunction, dehydration, bacteremia, sepsis, anorexia nervosa, damaged tissue after chemotherapy e.g. chemotherapy-induced intestinal mucositis, premature infants incl. intestinal failure in premature infants, preborn infants incl. intestinal failure in preborn infants, schleroderma, gastritis including atrophic gastritis, postantrectomy atrophic gastritis and helicobacter pylori gastritis, pancreatitis, general septic shock ulcers, enteritis, cul-de-sac, lymphatic obstruction, vascular disease and graft-versus-host, healing after surgical procedures, post radiation atrophy and chemotherapy, weight loss in Parkinson's Disease, intestinal adaptation after surgical procedure, parenteral nutrition-induced mucosal atrophy, e.g. total parenteral nutrition (TPN)-induced mucosal atrophy, and bone-related disorders including osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, or glucocorticoid-induced osteoporosis.

In a further aspect, the invention relates to the use of a GLP-2 receptor agonist for the preparation of a medicament for the treatment of small bowel syndrome, Inflammatory bowel syndrome, Crohns disease, colitis including collagen colitis, radiation colitis, ulcerative colitis, chronic radiation enteritis, non-tropical (gluten intolerance) and tropical sprue, Coeliac disease (gluten sensitive enteropathy), damaged tissue after vascular obstruction or trauma, diarrhea e.g. tourist diarrhea and post-infective diarrhea, chronic bowel dysfunction, dehydration, bacteremia, sepsis, anorexia nervosa, damaged tissue after chemotherapy e.g. chemotherapy-induced intestinal mucositis, premature infants incl. intestinal failure in premature infants, preborn infants incl. intestinal failure in preborn infants, schleroderma, gastritis including atrophic gastritis, postantrectomy atrophic gastritis and helicobacter pylori gastritis, pancreatitis, general septic shock ulcers, enteritis, cul-de-sac, lymphatic obstruction, vascular disease and graft-versus-host, healing after surgical procedures, post radiation atrophy and chemotherapy, weight loss in Parkinson's Disease, intestinal adaptation after surgical procedure, parenteral nutrition-induced mucosal atrophy, e.g. total parenteral nutrition (TPN)-induced mucosal atrophy, and bone-related disorders including osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, or glucocorticoid-induced osteoporosis.

The term "premature infants" means any infant born prior to 37 weeks of gestation. The term includes both healthy infants and infants with a damaged and/or immature intestine.

The term "preborn infants" means any infant prior to birth. The term includes both healthy foetuses and foetuses with a damaged and/or immature intestine.

Animal studies indicate that GLP-2 is important for maturation of the foetal small and large intestines. The bowels of the infant born at term are prepared for immediate digestion of food, however this is not the case for a premature baby. Therefore, the invention relates to the use of a GLP-2 receptor agonist for the general maturation of the intestines of the premature newborn to accelerate and improve oral feeding as well as for the treatment of damaged tissue that may arise in these infants.

In a further aspect, the invention relates to the GLP-2 derivative of the invention for use as a medicament.

In a further aspect, the invention relates to a method for the treatment of intestinal failure or other condition leading to malabsorption of nutrients in the intestine, the method comprising administering a therapeutically or prophylactically effective amount of a GLP-2 derivative comprising a GLP-2 peptide, wherein a lipophilic substituent is attached to one or more amino acid residues at a position relative to the amino acid sequence of SEQ ID NO:1 independtly selected from the list consisting of S5, S7, D8, E9, M10, N11, T12, I13, L14, D15, N16, L17, A18, D21, N24, and Q28 with the proviso that said lipophilic substituent is not attached at the N-terminal amino acid residue or the C-terminal amino acid residue of said GLP-2 peptide; to a subject in need thereof.

In a further aspect, the invention relates to a method for the treatment of small bowel syndrome, Inflammatory bowel syndrome, Crohns disease, colitis including collagen colitis, radiation colitis, ulcerative colitis, chronic radiation enteritis, non-tropical (gluten intolerance) and tropical sprue, Coeliac disease (gluten sensitive enteropathy), damaged tissue after vascular obstruction or trauma, diarrhea e.g. tourist diarrhea and post-infective diarrhea, chronic bowel dysfunction, dehydration, bacteremia, sepsis, anorexia nervosa, damaged tissue after chemotherapy e.g. chemotherapy-induced intestinal mucositis, premature infants incl. intestinal failure in premature infants, preborn infants incl. intestinal failure in preborn infants, scleroderma, gastritis including atrophic gastritis, postantrectomy atrophic gastritis and helicobacter pylori gastritis, pancreatitis, general septic shock ulcers, enteritis, cul-de-sac, lymphatic obstruction, vascular disease and graft-versus-host, healing after surgical procedures, post radiation atrophy and chemotherapy, weight loss in Parkinson's Disease, intestinal adaptation after surgical procedure, parenteral nutrition-induced mucosal atrophy, e.g. total parenteral nutrition (TPN)-induced mucosal atrophy, and bone-related disorders including osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, or glucocorticoid-induced osteoporosis, the method comprising administering a therapeutically or prophylactically effective amount of a GLP-2 derivative comprising a GLP-2 peptide, wherein a lipophilic substituent is attached to one or more amino acid residues at a position relative to the amino acid sequence of SEQ ID NO:1 selected from the list consisting of S5, S7, D8, E9, M10, N11, T12, I13, L14, D15, N16, L17, A18, D21, N24, and Q28 with the proviso that said lipophilic substituent is not attached at the N-terminal amino acid residue or the C-terminal amino acid residue of said GLP-2 peptide; to a subject in need thereof.

In a further aspect, the invention relates to a method for the treatment of small bowel syndrome, Inflammatory bowel syndrome, Crohns disease, colitis including collagen colitis, radiation colitis, ulcerative colitis, chronic radiation enteritis, non-tropical (gluten intolerance) and tropical sprue, Coeliac disease (gluten sensitive enteropathy), damaged tissue after vascular obstruction or trauma, diarrhea e.g. tourist diarrhea and post-infective diarrhea, chronic bowel dysfunction, dehydration, bacteremia, sepsis, anorexia nervosa, damaged tissue after chemotherapy e.g. chemotherapy-induced intestinal mucositis, premature infants incl. intestinal failure in premature infants, preborn infants incl. intestinal failure in preborn infants, scleroderma, gastritis including atrophic gastritis, postantrectomy atrophic gastritis and helicobacter pylori gastritis, pancreatitis, general septic shock ulcers, enteritis, cul-de-sac, lymphatic obstruction, vascular disease and graft-versus-host, healing after surgical procedures, post radiation atrophy and chemotherapy, weight loss in Parkinson's Disease, intestinal adaptation after surgical procedure, parenteral nutrition-induced mucosal atrophy, e.g. total parenteral nutrition (TPN)-induced mucosal atrophy, and bone-related disorders including osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, or glucocorticoid-induced osteoporosis, the method comprising administering a therapeutically or prophylactically effective amount of a GLP-2 receptor agonist.

In a further aspect, the invention relates to a method for producing the GLP-2 peptide comprising the amino acid sequence of formula I;

His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-Arg-$X^{21}$-Phe-Ile-$X^{24}$-Trp-Leu-Ile-$X^{28}$-Thr-Arg-Ile-Thr-$X^{33}$ (formula I);

or a fragment thereof; wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{21}$ is Asp, or Lys; $X^{24}$ is Asn, or Lys; $X^{28}$ is Gln, or Lys; $X^{33}$ is Asp, Glu, or Lys, the method comprising cultivating a host cell comprising a polynucleotide construct encoding a GLP-2 peptide comprising the amino acid sequence of formula I in an appropriate growth medium under conditions allowing expression of the polynucleotide construct and recovering the resulting peptide from the culture medium.

We have further discovered that GLP-2 and analogs thereof, modified GLP-2 and analogs thereof when formulated in aqueous solution together with a buffer, are physically stable when kept in the pH range from about 8 to about 10. The present formulations are physically stable within a given shelf life period at the recommended storage temperature (typically 2-3 years at 2-8° C.). Furthermore, the present formulations are physically stable during in-use (typically 1 month at accelerated temperatures e.g. 25° C. or 37° C.). The formulations of the invention are also chemically stable thus rendering them shelf-stable and suitable for invasive (e.g. injection, subcutaneous injection, intramuscular, intravenous or infusion) as well as non-invasive (e.g. nasal or pulmonary, transdermal or transmucosal e.g. buccal) means of administration. When the inventive formulation comprising a GLP-2 compound was compared to the same formulation at a pH lower than 8.0, the physical stability was increased considerably, and typically the shelf-life was increased from a few seconds to several months in the tests used.

One object of the present invention is to provide a pharmaceutical formulation comprising a GLP-2 compound, and a buffer, wherein said GLP-2 compound is present in a concentration from 0.1 mg/ml to 100 mg/ml, and wherein said formulation has a pH from 8.0 to 10.

Another object of the present invention is to provide a method of preparing a physically stable pharmaceutical formulation of a GLP-2 compound, comprising preparing a formulation containing the GLP-2 compound, and a buffer, wherein said GLP-2 compound is present in a concentration from 0.1 mg/ml to 100 mg/ml, and wherein said formulation has a pH from 8.0 to 10.

In one aspect of the invention the formulation contains a GLP-2 compound in a concentration from 1 mg/ml to 100 mg/ml.

In another aspect of the invention the formulation has a pH from 8.0 to 9.

We have further discovered that GLP-2 derivatives when formulated in aqueous solution together with a buffer, are physically stable when kept in the pH range from about 7 to about 10. The present formulations are physically stable within a given shelf life period at the recommended storage temperature (typically 2-3 years at 2-8° C.). Furthermore, the present formulations are physically stable during in-use (typically 1 month at accelerated temperatures e.g. 25° C. or 37° C.). The formulations of the invention are also chemically stable thus rendering them shelf-stable and suitable for invasive (e.g. injection, subcutaneous injection, intramuscular, intravenous or infusion) as well as non-invasive (e.g. nasal or pulmonary, transdermal or transmucosal e.g. buccal) means of administration. When the inventive formulation comprising a GLP-2 derivative was compared to the same formulation at a pH lower than 7.0, the physical stability was increased considerably, and typically the shelf-life was increased from a few seconds to several months in the tests used.

One object of the present invention is therefore to provide a pharmaceutical formulation comprising a GLP-2 derivative, and a buffer, wherein said GLP-2 derivative is present in a concentration from 0.1 mg/ml to 100 mg/ml, and wherein said formulation has a pH from 7.0 to 10.

Another object of the present invention is to provide a method of preparing a physically stable pharmaceutical formulation of a GLP-2 derivative, comprising preparing a formulation containing the GLP-2 derivative, and a buffer, wherein said GLP-2 derivative is present in a concentration from 0.1 mg/ml to 100 mg/ml, and wherein said formulation has a pH from 7.0 to 10.

In one aspect of the invention the formulation contains a GLP-2 derivative in a concentration from 1 mg/ml to 100 mg/ml. In another aspect of the invention the formulation has a pH from 7.0 to 9.

In a further aspect the invention relates to a pharmaceutical formulation comprising a GLP-2 derivative, and a buffer, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said formulation has a pH from 7.0 to 10.

In a further aspect the invention relates to a pharmaceutical formulation comprising an aqueous solution of a GLP-2 derivative, and a buffer, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said formulation has a pH from 7.0 to 10.

In a further aspect the invention relates to a method of preparing a physically stable pharmaceutical formulation of a GLP-2 derivative comprising preparing a formulation containing the GLP-2 derivative, and a buffer, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said formulation has a pH from 7.0 to 10.

In a further aspect the invention relates to a method of preparing a physically stable pharmaceutical formulation of a GLP-2 derivative comprising preparation of an aqueous solution containing the GLP-2 derivative, and a buffer, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said formulation has a pH from 7.0 to 10.

In a further aspect the invention relates to a method of preparing a physically stable pharmaceutical formulation of a GLP-2 derivative comprising preparing a formulation containing the GLP-2 derivative, water, and a buffer, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said formulation has a pH from 7.0 to 10.

In a further aspect the present invention relates to a method for the treatment of intestinal failure or other condition leading to malabsorption of nutrients in the intestine, comprising administering to a patient in need thereof an effective amount of a pharmaceutical formulation comprising an aqueous solution of a GLP-2 derivative, and a buffer, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said formulation has a pH from 7.0 to 10. In one embodiment the intestinal failure or other condition leading to malabsorption of nutrients in the intestine is selected from the list consisting of small bowel syndrome, Inflammatory bowel syndrome, Crohns disease, colitis including collagen colitis, radiation colitis, ulcerative colitis, chronic radiation enteritis, non-tropical (gluten intolerance) and tropical sprue, Coeliac disease (gluten sensitive enteropathy), damaged tissue after vascular obstruction or trauma, diarrhea e.g. tourist diarrhea and post-infective diarrhea, chronic bowel dysfunction, dehydration, bacteremia, sepsis, anorexia nervosa, damaged tissue after chemotherapy e.g. chemotherapy-induced intestinal mucositis, premature infants incl. intestinal failure in premature infants, preborn infants incl. intestinal failure in preborn infants, schleroderma, gastritis including atrophic gastritis, postantrectomy atrophic gastritis and helicobacter pylori gastritis, pancreatitis, general septic shock ulcers, enteritis, cul-de-sac, lymphatic obstruction, vascular disease and graft-versus-host, healing after surgical procedures, post radiation atrophy and chemotherapy, weight loss in Parkinson's Disease, intestinal adaptation after surgical procedure, parenteral nutrition-induced mucosal atrophy, e.g. total parenteral nutrition (TPN)-induced mucosal atrophy, and bone-related disorders including osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, or glucocorticoid-induced osteoporosis.

DETAILED DESCRIPTION OF THE INVENTION

Short Bowel Syndrome (SBS) is a devastating clinical condition encountered in a wide spectrum of medical and surgical conditions. The most common causes include irradiation, cancer, mesenteric vascular disease, Crohn's disease and trauma. With improved care of patients with SBS a greater number of patients are surviving for a longer period of time, thus magnifying the need for therapeutic interventions to reduce or eliminate the long-term problems associated with SBS. Although SBS patient have up to 7 meals a day they still have problems maintaining normal body weight and these patients are often maintained on parenteral nutrition either at home (HPN) or at the hospital.

Chemotherapy (CT) and radiation therapy (RT) for treatment of cancers target rapidly dividing cells. Since the cells of intestinal crypts (the simple tubular glands of the small intestine) are rapidly proliferating, CT/RT tends to produce intestinal mucosal damage as an adverse effect. Gastroenteritis, diarrhea, dehydration and, in some cases, bacteremia and sepsis may ensue. These side effects are severe for two reasons: They set the limit for the dose of therapy and thereby the efficacy of the treatment, and they represent a potentially life-threatening condition, which requires intensive and expensive treatment.

Animal studies have shown that CT-induced intestinal mucosal damage can be counteracted by GLP-2 peptides due to its potent intestinotrophic activity, which leads to an increase in bowel weight, villus height, crypt depth and crypt cell proliferation rate and, importantly, a reduction of crypt cell apoptosis. RT-induced GI tract damage and the potential protective effect of GLP-2 peptides follow the same rationale as that of CT.

Inflammatory bowel disease (IBD) comprises Crohn's disease, which mainly affects the small intestine, and ulcerative colitis, which mainly occurs in the distal colon and rectum. The pathology of IBD is characterized by chronic inflammation and destruction of the GI epithelium. Current treatment is directed towards suppression of inflammatory mediators. Stimulation of repair and regeneration of the epithelium by intestinotrophic agents such as GLP-2 derivatives according to the present invention might represent an alternative or adjunct strategy for treatment of IBD.

Dextran sulfate (DS)-induced colitis in rodents resembles ulcerative colitis in man, with development of mucosal edema, crypt erosions and abscesses, leading to polyp formation and progression to dysplasia and adenocarcinoma, but the precise mechanism underlying the toxicity of DS is not known. A beneficial effect of GLP-2 peptides in (DS)-induced colitis in mice have been demonstrated. Mice receiving 5% DS in the drinking water developed loose blood-streaked stools after 4-5 days and lost 20-25% of their body weight after 9-10 days. Mice that were in addition treated subcutaneously twice daily for the whole period (9-10 days) with either 350 ng or 750 ng A2G-GLP-2(1-33) lost significantly less body weight and appeared much healthier. The effects were dose-dependent. By histology, DS mice treated with A2G-GLP-2(1-33) exhibited a greater proportion of intact mucosal epithelium, increased colon length, crypt depth and mucosal area. These effects were mediated in part via enhanced stimulation of mucosal epithelial cell proliferation. It is concluded by the inventors of the present invention that there is a therapeutic potential for the treatment of IBD of GLP-2 derivatives according to the present invention, potentially in combination with anti-inflammatory drugs. Thus, there is a potential of GLP-2 derivatives according to the present invention as an adjunct to anti-inflammatory therapy in IBD. The predominant role of GLP-2 derivatives according to the present invention in IBD would be to enhance the regeneration of compromised intestinal epithelium.

The degradation of native GLP-2(1-33) in vivo in humans presumably by Dipeptidyl Peptidase IV (DPP-IV) has been studied in details. GLP-2 infusions (0.8 pmol/kg*min) increasing plasma level of intact GLP-2(1-33) from 9 pM to 131 pM was eliminated with TY2 value of 7 min. When an s.c. injection of GLP-2(1-33) was given (400 mg=106.000 pmol) the plasma concentration increased to a maximum of 1500 pM after 45 min. One hour after the s.c. injection, 69% of the injected GLP-2(1-33) was still intact GLP-2 (1-33). In both studies the only degradation product detected by HPLC was GLP-2(3-33) and it was concluded that GLP-2 is extensively degraded to GLP-2 (3-33) in humans presumably by DPP-IV. Thus the object of the present invention is to provide GLP-2 derivatives, that are resistant to DPP-IV degradation are thus more potent in vivo that the native GLP-2 peptide.

The term "GLP-2 peptide" as used herein means any protein comprising the amino acid sequence 1-33 of native human GLP-2 (SEQ ID NO: 1) or analogs thereof. This includes, but is not limited to, native human GLP-2 and analogs thereof.

The term "GLP-2" as used herein is intended to include proteins that have the amino acid sequence 1-33 of native human GLP-2 with amino acid sequence of SEQ ID NO:1. It also includes proteins with a slightly modified amino acid sequence, for instance, a modified N-terminal end including N-terminal amino acid deletions or additions so long as those proteins substantially retain the activity of GLP-2. "GLP-2" within the above definition also includes natural allelic variations that may exist and occur from one individual to another. Also, degree and location of glycosylation or other post-translation modifications may vary depending on the chosen host cells and the nature of the host cellular environment.

The terms "analog" or "analogs", as used herein, is intended to designate a GLP-2 peptide having the sequence of SEQ ID NO:1, wherein one or more amino acids of the parent GLP-2 protein have been substituted by another amino acid and/or wherein one or more amino acids of the parent GLP-2 protein have been deleted and/or wherein one or more amino acids have been inserted in protein and/or wherein one or more amino acids have been added to the parent GLP-2 protein. Such addition can take place either at the N-terminal end or at the C-terminal end of the parent GLP-2 protein or both. The "analog" or "analogs" within this definition still have GLP-2 activity as measured by the ability to exert a trophic effects on the small or large intestine. In one embodiment an analog is 70% identical with the sequence of SEQ ID NO:1. In one embodiment an analog is 80% identical with the sequence of SEQ ID NO:1. In another embodiment an analog is 90% identical with the sequence of SEQ ID NO:1. In a further embodiment an analog is 95% identical with the sequence of SEQ ID NO:1. In a further embodiment an analog is a GLP-2 peptide, wherein a total of up to ten amino acid residues of SEQ ID NO:1 have been exchanged with any amino acid residue. In a further embodiment an analog is a GLP-2 peptide, wherein a total of up to five amino acid residues of SEQ ID NO:1 have been exchanged with any amino acid residue. In a further embodiment an analog is a GLP-2 peptide, wherein a total of up to three amino acid residues of SEQ ID NO:1 have been exchanged with any amino acid residue. In a further embodiment an analog is a GLP-2 peptide, wherein a total of up to two amino acid residues of SEQ ID NO:1 have been exchanged with any amino acid residue. In a further embodiment an analog is a GLP-2 peptide, wherein a total of one amino acid residue of SEQ ID NO:1 have been exchanged with any amino acid residue.

The term "a fragment thereof", as used herein, means any fragment of the peptide according to formula I or II with at least 15 amino acids and having biological GLP-2 activity. GLP-2 acitivty may be measured be GLP-2 receptor binding affinity. In one embodiment the fragment has at least 20 amino acids. In one embodiment the fragment has at least 25 amino acids. In one embodiment the fragment has at least 30 amino acids. In one embodiment the fragment is according to formula I or II with one amino acid deletion in the C-terminal. In one embodiment the fragment is according to formula I or II with two amino acid deletions in the C-terminal. In one embodiment the fragment is according to formula I or II with three amino acid deletions in the C-terminal. In one embodiment the fragment is according to formula I or II with four amino acid deletions in the C-terminal.

In one embodiment the fragment is according to formula I or II with one amino acid deletion in the N-terminal. In one embodiment the fragment is according to formula I or II with two amino acid deletions in the N-terminal. In one embodiment the fragment is according to formula I or II with three amino acid deletions in the N-terminal. In one embodiment the fragment is according to formula I or II with four amino acid deletions in the N-terminal.

The term "derivative" is used in the present text to designate a peptide in which one or more of the amino acid residues have been chemically modified, e.g. by alkylation, acylation, ester formation or amide formation.

The term "a GLP-2 derivative" is used in the present text to designate a derivative of a GLP-2 peptide. In one embodiment the GLP-2 derivative according to the present invention has GLP-2 activity as measured by the ability to bind a GLP-2 receptor (GLP-2R) and/or exert a trophic effects on the small or large intestine. In one embodiment the GLP-2 receptor is selected from the list consisting of rat GLP-2R, mouse GLP-2R and human GLP-2R.

The term "lipophilic substituent" is characterised by comprising 4-40 carbon atoms and having a solubility in water at 20° C. in the range from about 0.1 mg/100 ml water to about 250 mg/100 ml water, such as in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml.

The term "polynucleotide construct" is intended to indicate a polynucleotide segment which may be based on a complete or partial naturally occurring nucleotide sequence encoding the peptide of interest. The construct may optionally contain other polynucleotide segments. In a similar way, the term "amino acids which can be encoded by polynucleotide constructs" covers amino acids which can be encoded by the polynucleotide constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln.

The term "a host cell", as used herein, represent any cell, including hybrid cells, in which heterologous DNA can be expressed. Typical host cells includes, but are not limited to insect cells, yeast cells, mammalian cells, including human cells, such as BHK, CHO, HEK, and COS cells.

In the present context, the term "treatment" is meant to include both prevention of an expected intestinal failure or other condition leading to malabsorption of nutrients in the intestine, such as in post radiation atrophy, and regulation of an already occurring intestinal failure, such as in Inflammatory bowel syndrome, with the purpose of inhibiting or minimising the effect of the condition leading to malabsorption of nutrients in the intestine. Prophylactic administration with the GLP-2 derivative according to the invention is thus included in the term "treatment".

The term "subject" as used herein is intended to mean any animal, in particular mammals, such as humans, and may, where appropriate, be used interchangeably with the term "patient".

As used herein the term "appropriate growth medium" means a medium containing nutrients and other components required for the growth of cells and the expression of the nucleic acid sequence encoding the GLP-2 peptide of the invention.

To obtain a satisfactory protracted profile of action of the GLP-2 derivative, the lipophilic substituent attached to the GLP-2 moiety, as an example comprises 4-40 carbon atoms, such as 8-25 carbon atoms. The lipophilic substituent may be attached to an amino group of the GLP-2 moiety by means of a carboxyl group of the lipophilic substituent which forms an amide bond with an amino group of the amino acid to which it is attached. As an alternative, the lipophilic substituent may be attached to said amino acid in such a way that an amino group of the lipophilic substituent forms an amide bond with a carboxyl group of the amino acid. As a further option, the lipophililic substituent may be linked to the GLP-2 moiety via an ester bond. Formally, the ester can be formed either by reaction between a carboxyl group of the GLP-2 moiety and a hydroxyl group of the substituent-to-be or by reaction between a hydroxyl group of the GLP-2 moiety and a carboxyl group of the substituent-to-be. As a further alternative, the lipophilic substituent can be an alkyl group which is introduced into a primary amino group of the GLP-2 moiety.

In one embodiment the GLP-2 peptide is an isolated GLP-2 compound.

In one embodiment the GLP-2 derivative is an isolated GLP-2 compound.

In one embodiment the GLP-2 compound is an isolated GLP-2 compound.

The term "isolated GLP-2 compound" refers to a compound of the present invention that (1) has been separated from at least about 50 percent of free polynucleotides, lipids, carbohydrates or other materials (i.e., contaminants) with which it is naturally associated. Preferably, the isolated compound or polypeptide is substantially free from any other contaminating polypeptides or other contaminants that are found in its natural environment which would interfere with its therapeutic, diagnostic, prophylactic or research use.

Preferably, the isolated compound or polypeptide has been separated from at least about 70, such as 80, such as 90, such as 95 percent of free polynucleotides, lipids, carbohydrates or other materials (i.e., contaminants) with which it is naturally associated In one embodiment of the invention the GLP-2 peptide consists of the amino acid sequence

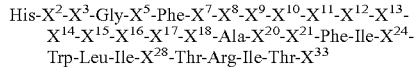
His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-$X^{20}$-$X^{21}$-Phe-Ile-$X^{24}$-Trp-Leu-Ile-$X^{28}$-Thr-Arg-Ile-Thr-$X^{33}$ or a fragment thereof; wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{20}$ is Arg, or Lys; $X^{21}$ is Asp, or Lys; $X^{24}$ is Asn, or Lys; $X^{28}$ is Gln, or Lys; $X^{33}$ is Asp, Glu, or Lys.

In one embodiment of the invention the GLP-2 peptide is according to formula II

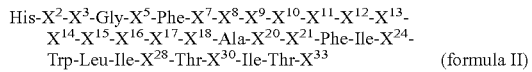
His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-$X^{20}$-$X^{21}$-Phe-Ile-$X^{24}$-Trp-Leu-Ile-$X^{28}$-Thr-$X^{30}$-Ile-Thr-$X^{33}$ (formula II)

or a fragment thereof; wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{20}$ is Arg, or Lys; $X^{21}$ is Asp, or Lys; $X^{24}$ is Asn, or Lys; $X^{28}$ is Gln, or Lys; $X^{30}$ is Arg, or Lys; $X^{33}$ is Asp, Glu, or Lys (formula II).

In one embodiment $X^2$ is Ala. In one embodiment $X^2$ is Gly. In one embodiment $X^3$ is Asp. In one embodiment $X^3$ is Glu. In one embodiment $X^5$ is Ser. In one embodiment $X^7$ is Ser. In one embodiment $X^8$ is Asp. In one embodiment $X^8$ is Glu. In one embodiment $X^9$ is Asp. In one embodiment $X^9$ is Glu. In one embodiment $X^{10}$ is selected from the group consisting of Met, Leu, Ile, and Nor-Leucine. In one embodiment $X^{11}$ is Asn. In one embodiment $X^{12}$ is Thr. In one embodiment $X^{13}$ is Ile. In one embodiment $X^{14}$ is Leu. In one embodiment $X^{15}$ is Asp. In one embodiment $X^{16}$ is Asn. In one embodiment $X^{17}$ is Leu. In one embodiment $X^{18}$ is Ala. In one embodiment $X^{21}$ is Asp. In one embodiment $X^{24}$ is Asn. In one embodiment $X^{28}$ is Gln. In one embodiment $X^{33}$ is Asp. In one embodiment $X^{33}$ is Glu. In one embodiment at least one amino acid independently selected from the list consisting of $X^5, X^7, X^8, X^9, X^{10}, X^{11}, X^{12}, X^{13}, X^{14}, X^{15}, X^{16}, X^{17}, X^{18}, X^{20}, X^{21}, X^{24}, X^{28}$, and $X^{33}$ is a Lys. In one embodiment the amino acid independently selected from the list consisting of $X^5, X^7, X^8, X^9, X^{10}, X^{11}, X^{12}, X^{13}, X^{14}, X^{15}, X^{16}, X^{17}, X^{18}, X^{20}, X^{21}, X^{24}, X^{28}$, and $X^{33}$ is Lys. In one embodiment the amino acid $X^5$ is Lys. In one embodiment the amino acid $X^7$ is Lys. In one embodiment the amino acid $X^8$ is Lys. In one embodiment the amino acid $X^9$ is Lys. In one embodiment the amino acid $X^{10}$ is Lys. In one embodiment the amino acid $X^{11}$ is Lys. In one embodiment the amino acid $X^{12}$ is Lys. In one embodiment the amino acid $X^{13}$ is Lys. In one embodiment the amino acid $X^{14}$ is Lys. In one embodiment the amino acid $X^{15}$ is Lys. In one embodiment the amino acid $X^{16}$ is Lys. In one embodiment the amino acid $X^{17}$ is Lys. In one embodiment the amino acid $X^{18}$ is Lys. In one embodiment the amino acid $X^{20}$ is Lys. In one embodiment the amino acid $X^{21}$ is Lys. In one embodiment the amino acid $X^{24}$ is Lys. In one embodiment the amino acid $X^{28}$ is Lys. In one embodiment the amino acid $X^{30}$ is Lys. In one embodiment the amino acid $X^{30}$ is Arg. In one embodiment the amino acid $X^{33}$ is Lys.

In one embodiment of the invention the GLP-2 peptide is a GLP-2 peptide, wherein a total of up to 5 amino acid residues have been exchanged with any α-amino acid residue, such as 4 amino acid recidues, 3 amino acid residues, 2 amino acid residues, or 1 amino acid residue.

In one embodiment of the invention the GLP-2 peptide is selected from the list consisting of: GLP-2(1-33), A2G-GLP-2(1-33), K30R-GLP-2(1-33); S5K-GLP-2(1-33); S7K-GLP-2(1-33); D8K-GLP-2(1-33); E9K-GLP-2(1-33); M10K-GLP-2(1-33); N11 K-GLP-2(1-33); T12K-GLP-2(1-33); 113K-GLP-2(1-33); L14K-GLP-2(1-33); D15K-GLP-2(1-33); N16K-GLP-2(1-33); L17K-GLP-2(1-33); A18K-GLP-2 (1-33); D21K-GLP-2(1-33); N24K-GLP-2(1-33); Q28K-GLP-2(1-33); S5K/K30R-GLP-2(1-33); S7K/K30R-GLP-2 (1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); 113K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/113K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); and D3E/Q28K/K30R/D33E-GLP-2(1-33).

In one embodiment of the invention the GLP-2 receptor agonist is selected from the list consisting of: GLP-2(1-33), A2G-GLP-2(1-33), K30R-GLP-2(1-33); S5K-GLP-2(1-33); S7K-GLP-2(1-33); D8K-GLP-2(1-33); E9K-GLP-2(1-33); M10K-GLP-2(1-33); N11 K-GLP-2(1-33); T12K-GLP-2(1-33); 113K-GLP-2(1-33); L14K-GLP-2(1-33); D15K-GLP-2 (1-33); N16K-GLP-2(1-33); L17K-GLP-2(1-33); A18K-GLP-2(1-33); D21K-GLP-2(1-33); N24K-GLP-2(1-33); Q28K-GLP-2(1-33); S5K/K30R-GLP-2(1-33); S7K/K30R-GLP-2(1-33); D8K/K30R-GLP-2(1-33); E9K/K30R-GLP-2 (1-33); M10K/K30R-GLP-2(1-33); N11K/K30R-GLP-2(1-33); T12K/K30R-GLP-2(1-33); 113K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/113K/K30R/D33E-GLP-2(1-33); D3E/L14K/K30R/D33E-GLP-2(1-33); D3E/D15K/K30R/D33E-GLP-2(1-33); D3E/N 16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); and D3E/Q28K/K30R/D33E-GLP-2(1-33).

In one embodiment of the invention the GLP-2 receptor agonist is a GLP-2 peptide.

In one embodiment of the invention the GLP-2 receptor agonist is a GLP-2 derivative.

In one embodiment of the invention the GLP-2 derivative comprises a GLP-2 peptide, wherein the GLP-2 peptide is according to formula II

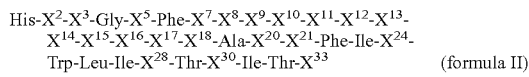

His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-$X^{20}$-$X^{21}$-Phe-Ile-$X^{24}$-Trp-Leu-Ile-$X^{28}$-Thr-$X^{30}$-Ile-Thr-$X^{33}$ (formula II)

or a fragment thereof; wherein $X^2$ is Ala, Val or Gly; $X^3$ is Asp, or Glu; $X^5$ is Ser, or Lys; $X^7$ is Ser, or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn, or Lys; $X^{12}$ is Thr, or Lys; $X^{13}$ is Ile, or Lys; $X^{14}$ is Leu, or Lys; $X^{15}$ is Asp, or Lys; $X^{16}$ is Asn, or Lys; $X^{17}$ is Leu, or Lys; $X^{18}$ is Ala, or Lys; $X^{20}$ is Arg, or Lys; $X^{21}$ is Asp, or Lys; $X^{24}$ is Asn, or Lys; $X^{28}$ is Gln, or Lys; $X^{30}$ is Arg, or Lys; $X^{33}$ is Asp, Glu, or Lys (formula II).

In one embodiment of the invention the GLP-2 derivative only has one lipophilic substituent attached to the GLP-2 peptide.

In one embodiment of the invention the lipophilic substituent comprises from 4 to 40 carbon atoms.

In one embodiment of the invention the lipophilic substituent comprises from 8 to 25 carbon atoms.

In one embodiment of the invention the lipophilic substituent comprises from 12 to 20 carbon atoms.

In one embodiment of the invention the lipophilic substituent is attached to an amino acid residue in such a way that a carboxyl group of the lipophilic substituent forms an amide bond with an amino group of the amino acid residue.

In one embodiment of the invention the lipophilic substituent is attached to a Lys residue.

In one embodiment of the invention the lipophilic substituent is attached to an amino acid residue in such a way that an amino group of the lipophilic substituent forms an amide bond with a carboxyl group of the amino acid residue.

In one embodiment of the invention the lipophilic substituent is attached to the GLP-2 peptide by means of a spacer.

In one embodiment of the invention the spacer is an unbranched alkane α,ω-dicarboxylic acid group having from 1 to 7 methylene groups, such as two methylene groups which spacer forms a bridge between an amino group of the GLP-2 peptide and an amino group of the lipophilic substituent.

In one embodiment of the invention the spacer is an amino acid residue except a Cys residue, or a dipeptide. Examples of suitable spacers includes β-alanine, gamma-aminobutyric acid (GABA), γ-glutamic acid, succinic acid, Lys, Glu or Asp, or a dipeptide such as Gly-Lys. When the spacer is succinic acid, one carboxyl group thereof may form an amide bond with an amino group of the amino acid residue, and the other carboxyl group thereof may form an amide bond with an amino group of the lipophilic substituent. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the ε-amino group of Lys and the lipophilic substituent. In one embodiment, such a further spacer is succinic acid which forms an amide bond with the ε-amino group of Lys and with an amino group present in the lipophilic substituent. In another embodiment such a further spacer is Glu or Asp which forms an amide bond with the ε-amino group of Lys and another amide bond with a carboxyl group present in the lipophilic substituent, that is, the lipophilic substituent is a $N^\epsilon$-acylated lysine residue.

In one embodiment of the invention the spacer is selected from the list consisting of β-alanine, gamma-aminobutyric acid (GABA), γ-glutamic acid, Lys, Asp, Glu, a dipeptide containing Asp, a dipeptide containing Glu, or a dipeptide containing Lys. In one embodiment of the invention the spacer is β-alanine. In one embodiment of the invention the spacer is gamma-aminobutyric acid (GABA). In one embodiment of the invention the spacer is γ-glutamic acid.

In one embodiment of the invention a carboxyl group of the parent GLP-2 peptide forms an amide bond with an amino group of a spacer, and the carboxyl group of the amino acid or dipeptide spacer forms an amide bond with an amino group of the lipophilic substituent.

In one embodiment of the invention an amino group of the parent GLP-2 peptide forms an amide bond with a carboxylic group of a spacer, and an amino group of the spacer forms an amide bond with a carboxyl group of the lipophilic substituent.

In one embodiment of the invention the lipophilic substituent comprises a partially or completely hydrogenated cyclopentanophenathrene skeleton.

In one embodiment of the invention the lipophilic substituent is an straight-chain or branched alkyl group. In one embodiment of the invention the lipophilic substituent is the acyl group of a straight-chain or branched fatty acid.

In one embodiment of the invention the acyl group of a lipophilic substituent is selected from the group comprising $CH_3(CH_2)_nCO$—, wherein n is 4 to 38, such as $CH_3(CH_2)_6CO$—, $CH_3(CH_2)_8CO$—, $CH_3(CH_2)_{10}CO$—, $CH_3(CH_2)_{12}CO$—, $CH_3(CH_2)_{14}CO$—, $CH_3(CH_2)_{16}CO$—, $CH_3(CH_2)_{18}CO$—, $CH_3(CH_2)_{20}CO$— and $CH_3(CH_2)_{22}CO$—.

In one embodiment of the invention the lipophilic substituent is an acyl group of a straight-chain or branched alkane α,ω-dicarboxylic acid.

In one embodiment of the invention the acyl group of the lipophilic substituent is selected from the group comprising $HOOC(CH_2)_mCO$—, wherein m is 4 to 38, such as $HOOC(CH_2)_{14}CO$—, $HOOC(CH_2)_{16}CO$—, $HOOC(CH_2)_{18}CO$—, $HOOC(CH_2)_{20}CO$— and $HOOC(CH_2)_{22}CO$—.

In one embodiment of the invention the lipophilic substituent is a group of the formula $CH_3(CH_2)_p((CH_2)_qCOOH)CHNH$—$CO(CH_2)_2CO$—, wherein p and q are integers and p+q is an integer of from 8 to 40, such as from 12 to 35.

In one embodiment of the invention the lipophilic substituent is a group of the formula $CH_3(CH_2)_rCO$—$NHCH(COOH)(CH_2)_2CO$—, wherein r is an integer of from 10 to 24.

In one embodiment of the invention the lipophilic substituent is a group of the formula $CH_3(CH_2)_5CO$—$NHCH((CH_2)_2COOH)CO$—, wherein s is an integer of from 8 to 24.

In one embodiment of the invention the lipophilic substituent is a group of the formula $COOH(CH_2)_tCO$— wherein t is an integer of from 8 to 24.

In one embodiment of the invention the lipophilic substituent is a group of the formula —$NHCH(COOH)(CH_2)_4NH$—$CO(CH_2)_uCH_3$, wherein u is an integer of from 8 to 18.

In one embodiment of the invention the lipophilic substituent is a group of the formula —$NHCH(COOH)(CH_2)_4NH$—$COCH((CH_2)_2COOH)NH$—$CO(CH_2)_wCH_3$, wherein w is an integer of from 10 to 16.

In one embodiment of the invention the lipophilic substituent is a group of the formula —$NHCH(COOH)(CH_2)_4NH$—$CO(CH_2)_2CH(COOH)NH$—$CO(CH_2)_xCH_3$, wherein x is an integer of from 10 to 16.

In one embodiment of the invention the lipophilic substituent is a group of the formula —$NHCH(COOH)(CH_2)_4NH$—$CO(CH_2)_2CH(COOH)NHCO(CH_2)_yCH_3$, wherein y is zero or an integer of from 1 to 22.

In one embodiment of the invention the lipophilic substituent is N-Lithocholoyl.

In one embodiment of the invention the lipophilic substituent is N-Choloyl.

In one embodiment of the invention the GLP-2 derivative has one lipophilic substituent. In one embodiment of the invention the GLP-2 derivative has two lipophilic substituents. In one embodiment of the invention the GLP-2 derivative has three lipophilic substituents. In one embodiment of the invention the GLP-2 derivative has four lipophilic substituents.

In one embodiment of the invention the GLP-2 derivative is selected from the group consisting of
S5K(3-(hexadecanoylamino)propionyl)-GLP-2(1-33);
S7K(3-(hexadecanoylamino)propionyl)-GLP-2(1-33);
D8K(3-(hexadecanoylamino)propionyl)-GLP-2(1-33);
E9K(3-(hexadecanoylamino)propionyl)-GLP-2(1-33);
M10K(3-(hexadecanoylamino)propionyl)-GLP-2(1-33);
N11 K(3-(hexadecanoylamino)propionyl)-GLP-2(1-33);
T12K(3-(hexadecanoylamino)propionyl)-GLP-2(1-33);
I13K(3-(hexadecanoylamino)propionyl)-GLP-2(1-33);
L14K(3-(hexadecanoylamino)propionyl)-GLP-2(1-33);
D15K(3-(hexadecanoylamino)propionyl)-GLP-2(1-33);
N16K(3-(hexadecanoylamino)propionyl)-GLP-2(1-33);
L17K(3-(octanoylamino)propionyl)-GLP-2(1-33);
L17K(3-(nonanoylamino)propionyl)-GLP-2(1-33);
L17K(3-(decanoylamino)propionyl)-GLP-2(1-33);
L17K(3-(undecanoylamino)propionyl)-GLP-2(1-33);
L17K(3-(dodecanoylamino)propionyl)-GLP-2(1-33);
L17K(3-(tridecanoylamino)propionyl)-GLP-2(1-33);
L17K(3-(tetradecanoylamino)propionyl)-GLP-2(1-33);
L17K(3-(pentadecanoylamino)propionyl)-GLP-2(1-33);
L17K(3-(hexadecanoylamino)propionyl)-GLP-2(1-33);
L17K(3-(heptadecanoylamino)propionyl)-GLP-2(1-33);
L17K(3-(octadecanoylamino)propionyl)-GLP-2(1-33);
L17K(3-(nonadecanoylamino)propionyl)-GLP-2(1-33);
L17K(3-(eicosanoylamino)propionyl)-GLP-2(1-33);
L17K((S)-4-carboxy-4-(octanoylamino)butanoyl)-GLP-2(1-33);
L17K((S)-4-carboxy-4-(nonanoylamino)butanoyl)-GLP-2(1-33);
L17K((S)-4-carboxy-4-(decanoylamino)butanoyl)-GLP-2(1-33);
L17K((S)-4-carboxy-4-(undecanoylamino)butanoyl)-GLP-2(1-33);
L17K((S)-4-carboxy-4-(dodecanoylamino)butanoyl)-GLP-2(1-33);
L17K((S)-4-carboxy-4-(tridecanoylamino)butanoyl)-GLP-2(1-33);
L17K((S)-4-carboxy-4-(tetradecanoylamino)butanoyl)-GLP-2(1-33);
L17K((S)-4-carboxy-4-(pentadecanoylamino)butanoyl)-GLP-2(1-33);
L17K((S)-4-carboxy-4-(hexadecanoylamino)butanoyl)-GLP-2(1-33);
L17K((S)-4-carboxy-4-(heptadecanoylamino)butanoyl)-GLP-2(1-33);
L17K((S)-4-carboxy-4-(octadecanoylamino)butanoyl)-GLP-2(1-33);
L17K((S)-4-carboxy-4-(nonadecanoylamino)butanoyl)-GLP-2(1-33);
L17K((S)-4-carboxy-4-(eicosanoylamino)butanoyl)-GLP-2(1-33);
L17K(4-(octanoylamino)butanoyl)-GLP-2(1-33);
L17K(4-(nonanoylamino)butanoyl)-GLP-2(1-33);
L17K(4-(decanoylamino)butanoyl)-GLP-2(1-33);
L17K(4-(undecanoylamino)butanoyl)-GLP-2(1-33);
L17K(4-(dodecanoylamino)butanoyl)-GLP-2(1-33);
L17K(4-(tridecanoylamino)butanoyl)-GLP-2(1-33);
L17K(4-(tetradecanoylamino)butanoyl)-GLP-2(1-33);
L17K(4-(pentadecanoylamino)butanoyl)-GLP-2(1-33);
L17K(4-(hexadecanoylamino)butanoyl)-GLP-2(1-33);
L17K(4-(heptadecanoylamino)butanoyl)-GLP-2(1-33);
L17K(4-(octadecanoylamino)butanoyl)-GLP-2(1-33);
L17K(4-(nonadecanoylamino)butanoyl)-GLP-2(1-33);
L17K(4-(eicosanoylamino)butanoyl)-GLP-2(1-33);
A18K(3-(hexadecanoylamino)propionyl)-GLP-2(1-33);
D21 K(3-(hexadecanoylamino)propionyl)-GLP-2(1-33);
N24K(3-(hexadecanoylamino)propionyl)-GLP-2(1-33);
Q28K(3-(hexadecanoylamino)propionyl)-GLP-2(1-33);
S5K(3-(hexadecanoylamino)propionyl)/K30R-GLP-2(1-33);
S7K(3-(hexadecanoylamino)propionyl)/K30R-GLP-2(1-33);
D8K(3-(hexadecanoylamino)propionyl)/K30R-GLP-2(11-33);
E9K(3-(hexadecanoylamino)propionyl)/K30R-GLP-2(1-33);
M10K(3-(hexadecanoylamino)propionyl)/K30R-GLP-2(1-33);
N11 K(3-(hexadecanoylamino)propionyl)/K30R-GLP-2(1-33);
T12K(3-(hexadecanoylamino)propionyl)/K30R-GLP-2(1-33);
I13K(3-(hexadecanoylamino)propionyl)/K30R-GLP-2(1-33);
L14K(3-(hexadecanoylamino)propionyl)/K30R-GLP-2(1-33);
D15K(3-(hexadecanoylamino)propionyl)/K30R-GLP-2(1-33);
N16K(3-(hexadecanoylamino)propionyl)/K30R-GLP-2(1-33);
L17K(3-(octanoylamino)propionyl)/K30R-GLP-2(1-33);
L17K(3-(nonanoylamino)propionyl)/K30R-GLP-2(1-33);
L17K(3-(decanoylamino)propionyl)/K30R-GLP-2(1-33);
L17K(3-(undecanoylamino)propionyl)/K30R-GLP-2(1-33);
L17K(3-(dodecanoylamino)propionyl)/K30R-GLP-2(1-33);
L17K(3-(tridecanoylamino)propionyl)/K30R-GLP-2(1-33);
L17K(3-(tetradecanoylamino)propionyl)/K30R-GLP-2(1-33);
L17K(3-(pentadecanoylamino)propionyl)/K30R-GLP-2(1-33);
L17K(3-(hexadecanoylamino)propionyl)/K30R-GLP-2(1-33);
L17K(3-(heptadecanoylamino)propionyl)/K30R-GLP-2(1-33);
L17K(3-(octadecanoylamino)propionyl)/K30R-GLP-2(1-33);
L17K(3-(nonadecanoylamino)propionyl)/K30R-GLP-2(1-33);
L17K(3-(eicosanoylamino)propionyl)/K30R-GLP-2(1-33);
L17K((S)-4-carboxy-4-(octanoylamino)butanoyl)/K30R-GLP-2(1-33);
L17K((S)-4-carboxy-4-(nonanoylamino)butanoyl)/K30R-GLP-2(1-33);
L17K((S)-4-carboxy-4-(decanoylamino)butanoyl)/K30R-GLP-2(1-33);
L17K((S)-4-carboxy-4-(undecanoylamino)butanoyl)/K30R-GLP-2(1-33);
L17K((S)-4-carboxy-4-(dodecanoylamino)butanoyl)/K30R-GLP-2(1-33);
L17K((S)-4-carboxy-4-(tridecanoylamino)butanoyl)/K30R-GLP-2(1-33);
L17K((S)-4-carboxy-4-(tetradecanoylamino)butanoyl)/K30R-GLP-2(1-33);

L17K((S)-4-carboxy-4-(pentadecanoylamino)butanoyl)/
K30R-GLP-2(1-33);
L17K((S)-4-carboxy-4-(hexadecanoylamino)butanoyl)/
K30R-GLP-2(1-33);
L17K((S)-4-carboxy-4-(heptadecanoylamino)butanoyl)/
K30R-GLP-2(1-33);
L17K((S)-4-carboxy-4-(octadecanoylamino)butanoyl)/
K30R-GLP-2(1-33);
L17K((S)-4-carboxy-4-(nonadecanoylamino)butanoyl)/
K30R-GLP-2(1-33);
L17K((S)-4-carboxy-4-(eicosanoylamino)butanoyl)/K30R-
GLP-2(1-33);
L17K(4-(octanoylamino)butanoyl)/K30R-GLP-2(1-33);
L17K(4-(nonanoylamino)butanoyl)/K30R-GLP-2(1-33);
L17K(4-(decanoylamino)butanoyl)/K30R-GLP-2(1-33);
L17K(4-(undecanoylamino)butanoyl)/K30R-GLP-2(1-33);
L17K(4-(dodecanoylamino)butanoyl)/K30R-GLP-2(1-33);
L17K(4-(tridecanoylamino)butanoyl)/K30R-GLP-2(1-33);
L17K(4-(tetradecanoylamino)butanoyl)/K30R-GLP-2(1-
33);
L17K(4-(pentadecanoylamino)butanoyl)/K30R-GLP-2(1-
33);
L17K(4-(hexadecanoylamino)butanoyl)/K30R-GLP-2(1-
33);
L17K(4-(heptadecanoylamino)butanoyl)/K30R-GLP-2(1-
33);
L17K(4-(octadecanoylamino)butanoyl)/K30R-GLP-2(1-
33);
L17K(4-(nonadecanoylamino)butanoyl)/K30R-GLP-2(1-
33);
L17K(4-(eicosanoylamino)butanoyl)/K30R-GLP-2(1-33);
A18K(3-(hexadecanoylamino)propionyl)/K30R-GLP-2(1-
33);
D21 K(3-(hexadecanoylamino)propionyl)/K30R-GLP-2(1-
33);
N24K(3-(hexadecanoylamino)propionyl)/K30R-GLP-2(1-
33);
Q28K(3-(hexadecanoylamino)propionyl)/K30R-GLP-2(11-
33);
D3E/S5K(3-(hexadecanoylamino)propionyl)/K30R/D33E-
GLP-2(1-33);
D3E/S7K(3-(hexadecanoylamino)propionyl)/K30R/D33E-
GLP-2(1-33);
D3E/D8K(3-(hexadecanoylamino)propionyl)/K30R/D33E-
GLP-2(1-33);
D3E/E9K(3-(hexadecanoylamino)propionyl)/K30R/D33E-
GLP-2(1-33);
D3E/M 10K(3-(hexadecanoylamino)propionyl)/K30R/
D33E-GLP-2(1-33);
D3E/N11 K(3-(hexadecanoylamino)propionyl)/K30R/
D33E-GLP-2(1-33);
D3E/T12K(3-(hexadecanoylamino)propionyl)/K30R/
D33E-GLP-2(1-33);
D3E/I13K(3-(hexadecanoylamino)propionyl)/K30R/D33E-
GLP-2(1-33);
D3E/L14K(3-(hexadecanoylamino)propionyl)/K30R/
D33E-GLP-2(1-33);
D3E/D15K(3-(hexadecanoylamino)propionyl)/K30R/
D33E-GLP-2(1-33);
D3E/N 16K(3-(hexadecanoylamino)propionyl)/K30R/
D33E-GLP-2(1-33);
D3E/L17K(3-(octanoylamino)propionyl)/K30R/D33E-
GLP-2(1-33);
D3E/L17K(3-(nonanoylamino)propionyl)/K30R/D33E-
GLP-2(1-33);
D3E/L17K(3-(decanoylamino)propionyl)/K30R/D33E-
GLP-2(1-33);
D3E/L 17K(3-(undecanoylamino)propionyl)/K30R/D33E-
GLP-2(1-33);
D3E/L17K(3-(dodecanoylamino)propionyl)/K30R/D33E-
GLP-2(1-33);
D3E/L17K(3-(tridecanoylamino)propionyl)/K30R/D33E-
GLP-2(1-33);
D3E/L17K(3-(tetradecanoylamino)propionyl)/K30R/D33E-
GLP-2(1-33);
D3E/L 17K(3-(pentadecanoylamino)propionyl)/K30R/
D33E-GLP-2(1-33);
D3E/L17K(3-(hexadecanoylamino)propionyl)/K30R/
D33E-GLP-2(1-33);
D3E/L17K(3-(heptadecanoylamino)propionyl)/K30R/
D33E-GLP-2(1-33);
D3E/L17K(3-(octadecanoylamino)propionyl)/K30R/D33E-
GLP-2(1-33);
D3E/L17K(3-(nonadecanoylamino)propionyl)/K30R/
D33E-GLP-2(1-33);
D3E/L17K(3-(eicosanoylamino)propionyl)/K30R/D33E-
GLP-2(1-33);
D3E/L17K((S)-4-carboxy-4-(octanoylamino)butanoyl)/
K30R/D33E-GLP-2(1-33);
D3E/L17K((S)-4-carboxy-4-(nonanoylamino)butanoyl)/
K30R/D33E-GLP-2(1-33);
D3E/L17K((S)-4-carboxy-4-(decanoylamino)butanoyl)/
K30R/D33E-GLP-2(1-33);
D3E/L17K((S)-4-carboxy-4-(undecanoylamino)butanoyl)/
K30R/D33E-GLP-2(1-33);
D3E/L17K((S)-4-carboxy-4-(dodecanoylamino)butanoyl)/
K30R/D33E-GLP-2(1-33);
D3E/L17K((S)-4-carboxy-4-(tridecanoylamino)butanoyl)/
K30R/D33E-GLP-2(1-33);
D3E/L17K((S)-4-carboxy-4-(tetradecanoylamino)bu-
tanoyl)/K30R/D33E-GLP-2(1-33);
D3E/L17K((S)-4-carboxy-4-(pentadecanoylamino)bu-
tanoyl)/K30R/D33E-GLP-2(1-33);
D3E/L17K((S)-4-carboxy-4-(hexadecanoylamino)bu-
tanoyl)/K30R/D33E-GLP-2(1-33);
D3E/L17K((S)-4-carboxy-4-(heptadecanoylamino)bu-
tanoyl)/K30R/D33E-GLP-2(1-33);
D3E/L17K((S)-4-carboxy-4-(octadecanoylamino)bu-
tanoyl)/K30R/D33E-GLP-2(1-33);
D3E/L17K((S)-4-carboxy-4-(nonadecanoylamino)bu-
tanoyl)/K30R/D33E-GLP-2(1-33);
D3E/L17K((S)-4-carboxy-4-(eicosanoylamino)butanoyl)/
K30R/D33E-GLP-2(1-33);
D3E/L17K(4-(octanoylamino)butanoyl)/K30R/D33E-GLP-
2(1-33);
D3E/L17K(4-(nonanoylamino)butanoyl)/K30R/D33E-
GLP-2(1-33);
D3E/L17K(4-(decanoylamino)butanoyl)/K30R/D33E-
GLP-2(1-33);
D3E/L17K(4-(undecanoylamino)butanoyl)/K30R/D33E-
GLP-2(1-33);
D3E/L17K(4-(dodecanoylamino)butanoyl)/K30R/D33E-
GLP-2(1-33);
D3E/L17K(4-(tridecanoylamino)butanoyl)/K30R/D33E-
GLP-2(1-33);
D3E/L17K(4-(tetradecanoylamino)butanoyl)/K30R/D33E-
GLP-2(1-33);
D3E/L17K(4-(pentadecanoylamino)butanoyl)/K30R/D33E-
GLP-2(1-33);
D3E/L17K(4-(hexadecanoylamino)butanoyl)/K30R/D33E-
GLP-2(1-33);
D3E/L17K(4-(heptadecanoylamino)butanoyl)/K30R/D33E-
GLP-2(1-33);

D3E/L17K(4-(octadecanoylamino)butanoyl)/K30R/D33E-GLP-2(1-33);
D3E/L17K(4-(nonadecanoylamino)butanoyl)/K30R/D33E-GLP-2(1-33);
D3E/L17K(4-(eicosanoylamino)butanoyl)/K30R/D33E-GLP-2(1-33);
D3E/A18K(3-(hexadecanoylamino)propionyl)/K30R/D33E-GLP-2(1-33);
D3E/D21 K(3-(hexadecanoylamino)propionyl)/K30R/D33E-GLP-2(1-33);
D3E/N24K(3-(hexadecanoylamino)propionyl)/K30R/D33E-GLP-2(1-33); and
D3E/Q28K(3-(hexadecanoylamino)propionyl)/K30R/D33E-GLP-2(1-33).

In a further embodiment, the present invention relates to a GLP-2 derivative in which the C-terminal amino acid residue is present in the form of the amide.

In a further embodiment, the present invention relates to a GLP-2 derivative having a lipophilic substituent which can be negatively charged. In one embodiment the group which can be negatively charged is a carboxylic acid group.

The parent GLP-2 peptide can be produced by a method which comprises culturing a host cell containing a DNA sequence encoding the GLP-2 peptide and capable of expressing the GLP-2 peptide in a suitable nutrient medium under conditions permitting the expression of the GLP-2 peptide, after which the resulting GLP-2 peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The GLP-2 peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of GLP-2 peptide in question.

The DNA sequence encoding the parent GLP-2 peptide may suitably be of genomic or cDNA origin, for instance obtained by preparing a genomic or cDNA library and screening for DNA sequences coding for all or part of the GLP-2 peptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the GLP-2 peptide may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the GLP-2 peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the GLP-2 peptide of the invention in a variety of host cells are well known in the art, cf. for instance Sambrook et al., supra.

The DNA sequence encoding the GLP-2 peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent GLP-2 peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the GLP-2 peptide in the correct reading frame. Secretory signal sequences are commonly positioned 5' to the DNA sequence encoding the GLP-2 peptide. The secretory signal sequence may be that normally associated with the GLP-2 peptide or may be from a gene encoding another secreted protein.

The procedures used to ligate the DNA sequences coding for the present GLP-2 peptides, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present GLP-2 peptides and includes bacteria, yeast, fungi and higher eukaryotic cells. Examples of suitable host cells well known and used in the art are, without limitation, *E coli, Saccharomyces cerevisiae*, or mammalian BHK or CHO cell lines.

The GLP-2 derivatives of the invention can be prepared by introducing the lipophilic substituent into the parent GLP-2 peptide using methods known per se, see for example WO 95/07931, the contents of which is hereby incorporated in its entirety by reference.

$N^\epsilon$ acylation of a Lys residue can be carried out by using an activated amide of the acyl group to be introduced as the acylating agent, e.g. the amide with benzotriazole. The acylation is carried out in a polar solvent in the presence of a base.

Pharmaceutical Compositions

Pharmaceutical compositions containing a GLP-2 derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the GLP-2 derivative in the form of a nasal or pulmonal spray. As a still further option, the GLP-2 derivatives of the invention can also be administered transdermally, e.g. from a patch, optionally a iontophoretic patch, or transmucosally, e.g. bucally.

Pharmaceutical compositions containing a GLP-2 derivative of the present invention may be prepared by conventional techniques, e.g. as described in *Remington's Pharmaceutical Sciences*, 1985 or in Remington: *The Science and Practice of Pharmacy*, 19th edition, 1995.

Thus, the injectable compositions of the GLP-2 derivative of the invention can be prepared using the conventional techniques of the pharmaceutical industry which involves dissolving and mixing the ingredients as appropriate to give the desired end product.

Thus, according to one procedure, the GLP-2 derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

Further to the above-mentioned components, solutions containing a GLP-2 derivative according to the present invention may also contain a surfactant in order to improve the solubility and/or the stability of the derivative.

A composition for nasal administration of GLP-2 may, for example, be prepared as described in European Patent No. 272097 (to Novo Nordisk A/S) or in WO 93/18785.

The GLP-2 derivatives of this invention can be used in the treatment of various diseases. The particular GLP-2 derivative to be used and the optimal dose level for any patient will depend on the disease to be treated and on a variety of factors including the efficacy of the specific peptide derivative employed, the age, body weight, physical activity, and diet of the patient, on a possible combination with other drugs, and on the severity of the case. It is recommended that the dosage of the GLP-2 derivative of this invention be determined for each individual patient by those skilled in the art in a similar way as for known parent GLP-2 peptides.

The pharmacological properties of the compounds of the invention can be tested e.g. as described in our International Patent Application No. PCT/DK97/00086, WO 97/31943 the contents of which is hereby incorporated in its entirety by reference.

In a further aspect the invention relates to a pharmaceutical formulation comprising a GLP-2 compound, and a buffer, wherein said GLP-2 compound is present in a concentration from 0.1 mg/ml to 100 mg/ml, and wherein said formulation has a pH from 8.0 to 10.

In a further aspect the invention relates to a pharmaceutical formulation comprising an aqueous solution of a GLP-2 compound, and a buffer, wherein said GLP-2 compound is present in a concentration from 0.1 mg/ml to 100 mg/ml, and wherein said formulation has a pH from 8.0 to 10.

In a further aspect the invention relates to a method of preparing a physically stable pharmaceutical formulation of a GLP-2 compound comprising preparing a formulation containing the GLP-2 compound, and a buffer, wherein said GLP-2 compound is present in a concentration from 0.1 mg/ml to 100 mg/ml, and wherein said formulation has a pH from 8.0 to 10.

In a further aspect the invention relates to a method of preparing a physically stable pharmaceutical formulation of a GLP-2 compound comprising preparation of an aqueous solution containing the GLP-2 compound, and a buffer, wherein said GLP-2 compound is present in a concentration from 0.1 mg/ml to 100 mg/ml, and wherein said formulation has a pH from 8.0 to 10.

In a further aspect the invention relates to a method of preparing a physically stable pharmaceutical formulation of a GLP-2 compound comprising preparing a formulation containing the GLP-2 compound, water, and a buffer, wherein said GLP-2 compound is present in a concentration from 0.1 mg/ml to 100 mg/ml, and wherein said formulation has a pH from 8.0 to 10.

In a further aspect the present invention relates to a method for the treatment of intestinal failure or other condition leading to malabsorption of nutrients in the intestine, comprising administering to a patient in need thereof an effective amount of a pharmaceutical formulation comprising an aqueous solution of a GLP-2 compound, and a buffer, wherein said GLP-2 compound is present in a concentration from 0.1 mg/ml to 100 mg/ml, and wherein said formulation has a pH from 8.0 to 10. In one embodiment the intestinal failure or other condition leading to malabsorption of nutrients in the intestine is selected from the list consisting of small bowel syndrome, Inflammatory bowel syndrome, Crohns disease, colitis including collagen colitis, radiation colitis, ulcerative colitis, chronic radiation enteritis, non-tropical (gluten intolerance) and tropical sprue, Coeliac disease (gluten sensitive enteropathy), damaged tissue after vascular obstruction or trauma, diarrhea e.g. tourist diarrhea and post-infective diarrhea, chronic bowel dysfunction, dehydration, bacteremia, sepsis, anorexia nervosa, damaged tissue after chemotherapy e.g. chemotherapy-induced intestinal mucositis, premature infants incl. intestinal failure in premature infants, preborn infants incl. intestinal failure in preborn infants, schleroderma, gastritis including atrophic gastritis, postantrectomy atrophic gastritis and helicobacter pylori gastritis, pancreatitis, general septic shock ulcers, enteritis, cul-de-sac, lymphatic obstruction, vascular disease and graft-versus-host, healing after surgical procedures, post radiation atrophy and chemotherapy, weight loss in Parkinson's Disease, intestinal adaptation after surgical procedure, parenteral nutrition-induced mucosal atrophy, e.g. total parenteral nutrition (TPN)-induced mucosal atrophy, and bone-related disorders including osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, or glucocorticoid-induced osteoporosis.

The term "an effective amount" is the effective dose to be determined by a qualified practitioner, who may titrate dosages to achieve the desired response. Factors for consideration of dose will include potency, bioavailability, desired pharmacokinetic/pharmacodynamic profiles, condition of treatment (e.g. diabetes, obesity, weight loss, gastric ulcers), patient-related factors (e.g. weight, health, age, etc.), presence of co-administered medications (e.g. insulin), time of administration, or other factors known to a medical practitioner.

In one embodiment of the invention the pharmaceutical formulation is an aqueous formulation, i.e. a formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds the solvent prior to use.

In another embodiment the pharmaceutical formulation is a lyophilised formulation whereto the physician or the patient adds the solvent prior to use.

Pharmaceutical compositions containing a GLP-2 compound according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a solution or suspension for the administration of the GLP-2 compound in the form of a nasal or pulmonal spray. As a still further option, the pharmaceutical compositions containing the GLP-2 compound of the invention can also be adapted to transdermal administration, e.g. from a patch, optionally a iontophoretic patch, or transmucosal, e.g. bucal, administration.

A pharmaceutical formulation is found to be physically unstable when it exhibits turbidity. Some of the present formulations may be physically stable for more than 11 months and for more than 22 months at 5° C.

Physical stability of the formulations is evaluated by means of visual inspection and turbidity after storage of the formulation at different temperatures in top filled glass cartridges for various time periods. Visual inspection of the formulations is performed in a sharp focused light with a dark background. The turbidity of the formulation is characterized by a visual score ranking the degree of turbidity from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight.

In one embodiment of the invention the pharmaceutical formulation comprising the GLP-2 compound is physically stable for more than 12 weeks and for more than 15 months at 5° C. as measured by visual inspection.

In another embodiment of the invention the pharmaceutical formulation comprising the GLP-2 compound is physically stable for more than 12 weeks at 25° C. as measured by visual inspection.

In a further embodiment of the invention the pharmaceutical formulation comprising the GLP-2 compound is physically stable for more than 12 weeks at 37° C. as measured by visual inspection.

In a further embodiment of the invention the formulation has a pH in the range from 7.6 to 10. In a further embodiment of the invention the formulation has a pH in the range from 7.7 to 10. In a further embodiment of the invention the formulation has a pH in the range from 7.8 to 10. In a further embodiment of the invention the formulation has a pH in the range from 7.9 to 10. In a further embodiment of the invention the formulation has a pH in the range from 8.0 to 10. In a further embodiment of the invention the formulation has a pH in the range from 8.0 to 9.5. In a further embodiment of the invention the formulation has a pH in the range from 8.0 to 9.0. In a further embodiment of the invention the formulation has a pH in the range from 8.0 to 8.5. In a further embodiment of the invention the formulation has a pH in the range from 8.5 to 10. In a further embodiment of the invention the formulation has a pH in the range from 8.5 to 9.5. In a further embodiment of the invention the formulation has a pH in the range from 8.5 to 9.0. In a further embodiment of the invention the formulation has a pH in the range from 9.0 to 10. In a further embodiment of the invention the formulation has a pH in the range from 9.0 to 9.5. In a further embodiment of the invention the formulation has a pH in the range from 9.5 to 10.

In a further embodiment of the invention the buffer is selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, or mixtures thereof. Each one of these specific buffers constitutes an alternative embodiment of the invention. In a further embodiment of the invention the buffer is glycylglycine, sodium dihydrogen phosphate, disodium hydrogen phosphate, sodium phosphate or mixtures thereof.

It is an object of the present invention to provide a pharmaceutical formulation with an increased solubility of the GLP-2 compound.

In a further embodiment of the invention the GLP-2 compound is present in a concentration from 0.1 mg/ml to 80 mg/ml. In a further embodiment of the invention the GLP-2 compound is present in a concentration from 1 mg/ml to 80 mg/ml. In a further embodiment of the invention the GLP-2 compound is present in a concentration from 0.1 mg/ml to 50 mg/ml. In a further embodiment of the invention the GLP-2 compound is present in a concentration from 1 mg/ml to 50 mg/ml. In a further embodiment of the invention the GLP-2 compound is present in a concentration from 0.1 mg/ml to 20 mg/ml. In a further embodiment of the invention the GLP-2 compound is present in a concentration from 1 mg/ml to 20 mg/ml. In a further embodiment of the invention the GLP-2 compound is present in a concentration from 0.1 mg/ml to 10 mg/ml. In a further embodiment of the invention the GLP-2 compound is present in a concentration from 1 mg/ml to 10 mg/ml. In a further embodiment of the invention the GLP-2 compound is present in a concentration from 0.1-5 mg/ml. In a further embodiment of the invention the GLP-2 compound is present in a concentration from 1-5 mg/ml. In a further embodiment of the invention the GLP-2 compound is present in a concentration from 0.1-0.5 mg/ml. In a further embodiment of the invention the GLP-2 compound is present in a concentration from 0.6-1 mg/ml. Each one of these specific concentration ranges constitutes an alternative embodiment of the invention.

In a further embodiment of the invention the formulation further comprises a pharmaceutically acceptable preservative. In a further embodiment of the invention the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment of the invention. In a preferred embodiment of the invention the preservative is phenol or m-cresol.

In a further embodiment of the invention the preservative is present in a concentration from 0.1 mg/ml to 20 mg/ml. In a further embodiment of the invention the preservative is present in a concentration from 0.1 mg/ml to 5 mg/ml. in a further embodiment of the invention the preservative is present in a concentration from 5 mg/ml to 10 mg/ml. In a further embodiment of the invention the preservative is present in a concentration from 10 mg/ml to 20 mg/ml. Each one of these specific concentration ranges constitutes an alternative embodiment of the invention.

The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a polyhydric alcohol (e.g. propyleneglycol, xylitol, mannitol, sorbitol or glycerol), a monosaccharide (e.g. glucose or maltose), a disccharide (e.g. sucrose), an amino acid (e.g. L-glycine, L-histidine, arginine, lysine, isoleucine, aspartic acid, tryptophan, threonine), polyethyleneglycol (e.g. PEG400), or mixtures thereof. In a further embodiment of the invention the isotonic agent is selected from the group consisting of sodium chloride, glycerol, mannitol, glucose, sucrose, L-glycine, L-histidine, arginine, lysine or mixtures thereof. Each one of these specific isotonic agents constitutes an alternative embodiment of the invention. In one embodiments of the invention the isotonic agent is mannitol. In one embodiments of the invention the isotonic agent is glycerol. In one embodiments of the invention the isotonic agent is sucrose.

In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 16 mg/ml. In a further embodiment of the invention the isotonic agent is present in a concentration from 17 mg/ml to 50 mg/ml. Each one of these specific concentration ranges constitutes an alternative embodiment of the invention.

The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethlenediaminetetraacetic acid (EDTA), citric acid, and aspartic acid, and mixtures thereof. Each one of these specific chelating agents constitutes an alternative embodiment of the invention.

In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml.

The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabiliser selected from the group of high molecular weight polymers or low molecular compounds. In a further embodiment of the invention the stabilizer is selected from polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment of the invention. In a preferred embodiment of the invention the stabiliser is selected from the group consisting of L-histidine, imidazole and arginine.

In a further embodiment of the invention the high molecular weight polymer is present in a concentration from 0.1 mg/ml to 50 mg/ml. In a further embodiment of the invention the high molecular weight polymer is present in a concentration from 0.1 mg/ml to 5 mg/ml. In a further embodiment of the invention the high molecular weight polymer is present in a concentration from 5 mg/ml to 10 mg/ml. In a further embodiment of the invention the high molecular weight polymer is present in a concentration from 10 mg/ml to 20 mg/ml. In a further embodiment of the invention the high molecular weight polymer is present in a concentration from 20 mg/ml to 30 mg/ml. In a further embodiment of the invention the high molecular weight polymer is present in a concentration from 30 mg/ml to 50 mg/ml.

In a further embodiment of the invention the low molecular weight compound is present in a concentration from 0.1 mg/ml to 50 mg/ml. In a further embodiment of the invention the low molecular weight compound is present in a concentration from 0.1 mg/ml to 5 mg/ml. In a further embodiment of the invention the low molecular weight compound is present in a concentration from 5 mg/ml to 10 mg/ml. In a further embodiment of the invention the low molecular weight compound is present in a concentration from 10 mg/ml to 20 mg/ml. In a further embodiment of the invention the low molecular weight compound is present in a concentration from 20 mg/ml to 30 mg/ml. In a further embodiment of the invention the low molecular weight compound is present in a concentration from 30 mg/ml to 50 mg/ml.

The use of a stabilizer in pharmaceutical compositions is well-known to the skilled person. For convenience reference is made to Remington: *The Science and Practice of Pharmacy*, 19$^{th}$ edition, 1995.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N, N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives- (e.g. sodium tauro-dihydrofusidate etc.), long-chain fatty acids and salts thereof C6-C12 (e.g. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, $19^{th}$ edition, 1995.

In one embodiment of the invention the pharmaceutical formulation comprising the GLP-2 derivative is physically stable for more than 12 weeks and for more than 15 months at 5° C. as measured by visual inspection.

In another embodiment of the invention the pharmaceutical formulation comprising the GLP-2 derivative is physically stable for more than 12 weeks at 25° C. as measured by visual inspection.

In a further embodiment of the invention the pharmaceutical formulation comprising the GLP-2 derivative is physically stable for more than 12 weeks at 37° C. as measured by visual inspection.

In a further embodiment of the invention the formulation comprising the GLP-2 derivative has a pH in the range from 7.0 to 10. In a further embodiment of the invention the formulation comprising the GLP-2 derivative has a pH in the range from 7.0 to 9.5. In a further embodiment of the invention the formulation comprising the GLP-2 derivative has a pH in the range from 7.0 to 9.0. In a further embodiment of the invention the formulation comprising the GLP-2 derivative has a pH in the range from 7.0 to 8.5. In a further embodiment of the invention the formulation comprising the GLP-2 derivative has a pH in the range from 7.0 to 8.0. In a further embodiment of the invention the formulation comprising the GLP-2 derivative has a pH in the range from 7.0 to 7.5. In a further embodiment of the invention the formulation comprising the GLP-2 derivative has a pH in the range from 7.5 to 10. In a further embodiment of the invention the formulation comprising the GLP-2 derivative has a pH in the range from 8.0 to 10. In a further embodiment of the invention the formulation comprising the GLP-2 derivative has a pH in the range from 8.5 to 10. In a further embodiment of the invention the formulation comprising the GLP-2 derivative has a pH in the range from 9.0 to 10. In a further embodiment of the invention the formulation comprising the GLP-2 derivative has a pH in the range from 9.5 to 10. In a further embodiment of the invention the formulation comprising the GLP-2 derivative has a pH in the range from 7.5 to 9.5. In a further embodiment of the invention the formulation comprising the GLP-2 derivative has a pH in the range from 7.5 to 9.0. In a further embodiment of the invention the formulation comprising the GLP-2 derivative has a pH in the range from 7.5 to 8.5. In a further embodiment of the invention the formulation comprising the GLP-2 derivative has a pH in the range from 7.5 to 8.0. In a further embodiment of the invention the formulation comprising the GLP-2 derivative has a pH in the range from 8.0 to 9.5. In a further embodiment of the invention the formulation comprising the GLP-2 derivative has a pH in the range from 8.0 to 9.0. In a further embodiment of the invention the formulation comprising the GLP-2 derivative has a pH in the range from 8.0 to 8.5. In a further embodiment of the invention the formulation comprising the GLP-2 derivative has a pH in the range from 8.5 to 9.5. In a further embodiment of the invention the formulation comprising the GLP-2 derivative has a pH in the range from 8.5 to 9.0. In a further embodiment of the invention the formulation comprising the GLP-2 derivative has a pH in the range from 9.0 to 9.5.

It is an object of the present invention to provide a pharmaceutical formulation with an increased solubility of the GLP-2 derivative.

In a further embodiment of the invention the GLP-2 derivative is present in a concentration from 0.1 mg/ml to 80 mg/ml. In a further embodiment of the invention the GLP-2 derivative is present in a concentration from 1 mg/ml to 80 mg/ml. In a further embodiment of the invention the GLP-2 derivative is present in a concentration from 0.1 mg/ml to 50 mg/ml. In a further embodiment of the invention the GLP-2 derivative is present in a concentration from 1 mg/ml to 50 mg/ml. In a further embodiment of the invention the GLP-2 derivative is present in a concentration from 0.1 mg/ml to 20 mg/ml. In a further embodiment of the invention the GLP-2 derivative is present in a concentration from 1 mg/ml to 20 mg/ml. In a further embodiment of the invention the GLP-2 derivative is present in a concentration from 0.1 mg/ml to 10 mg/ml. In a further embodiment of the invention the GLP-2 derivative is present in a concentration from 1 mg/ml to 10 mg/ml. In a further embodiment of the invention the GLP-2 derivative is present in a concentration from 0.1-5 mg/ml. In a further embodiment of the invention the GLP-2 derivative is present in a concentration from 1-5 mg/ml. In a further embodiment of the invention the GLP-2 derivative is present in a concentration from 0.1-0.5 mg/ml. In a further embodiment of the invention the GLP-2 derivative is present in a concentration from 0.6-1 mg/ml. Each one of these specific concentration ranges constitutes an alternative embodiment of the invention.

In the present context the GLP-2 compound and the GLP-2 derivative binds to a GLP-2 receptor, preferably with an affinity constant ($K_D$) or a potency ($EC_{50}$) of below 1 µM, e.g. below 100 nM. The term "GLP-2 compound" encompasses GLP-2 peptides as well as GLP-2 derivatives. Examples of suitable GLP-2 compounds which can be used in the present formulation have been disclosed in e.g. WO 96/29342, WO 97/31943, WO 98/08872, WO 96/32414, WO 97/39031, which are incorporated herein by reference.

Candidate GLP-2 compounds, which may be used according to the present invention may be, for instance, the GLP-2 analogs as described in WO 96/32414, WO 97/39031, WO 98/03547, the GLP-2 derivatives as described in WO 96/29342, WO 97/31943, WO 98/08872, incorporated herein by reference.

In one embodiment of the invention the GLP-2 compound is a GLP-2 derivative comprising a GLP-2 peptide, wherein a lipophilic substituent is attached to one or more amino acid residues at a position relative to the amino acid sequence of SEQ ID NO:1 selected from the list consisting of S5, S7, D8, E9, M10, N11, T12, I13, L14, D15, N16, L17, A18, D21, N24, and Q28. In one embodiment a lipophilic substituent is attached to an amino acid residues at the position S5 relative to the amino acid sequence of SEQ ID NO:1. In one embodiment a lipophilic substituent is attached to an amino acid residues at the position S7 relative to the amino acid sequence of SEQ ID NO:1. In one embodiment a lipophilic substituent is attached to an amino acid residues at the position D8 relative to the amino acid sequence of SEQ ID NO:1. In one embodiment a lipophilic substituent is attached to an amino acid residues at the position E9 relative to the amino acid sequence of SEQ ID NO:1. In one embodiment a lipophilic substituent is attached to an amino acid residues at the position M10 relative to the amino acid sequence of SEQ ID NO:1. In one embodiment a lipophilic substituent is attached to an amino acid residues at the position N11 relative to the amino acid sequence of SEQ ID NO:1. In one embodiment a lipophilic substituent is attached to an amino acid residues at the position T12 relative to the amino acid sequence of SEQ ID NO:1. In one embodiment a lipophilic substituent is attached to an amino acid residues at the position I13 relative to the amino acid sequence of SEQ ID NO:1. In one embodiment a lipophilic substituent is attached to an amino acid residues at the position L14 relative to the amino acid sequence of SEQ ID NO:1. In one embodiment a lipophilic substituent is attached to an amino acid residues at the position D15 relative to the amino acid sequence of SEQ ID NO:1. In one embodiment a lipophilic substituent is attached to an amino acid residues at the position N16 relative to the amino acid sequence of SEQ ID NO:1. In one embodiment a lipophilic substituent is attached to an amino acid residues at the position L17 relative to the amino acid sequence of SEQ ID NO:1. In one embodiment a lipophilic substituent is attached to an amino acid residues at the position A18 relative to the amino acid sequence of SEQ ID NO:1. In one embodiment a lipophilic substituent is attached to an amino acid residues at the position D21 relative to the amino acid sequence of SEQ ID NO:1. In one embodiment a lipophilic substituent is attached to an amino acid residues at the position N24 relative to the amino acid sequence of SEQ ID NO:1. In one embodiment a lipophilic substituent is attached to an amino acid residues at the position Q28 relative to the amino acid sequence of SEQ ID NO:1. It is to be understood that an amino acid residues at the position relative to the amino acid sequence of SEQ ID NO:1 may be any amino acid residue and not only the amino acid residue naturally present at that position. In one embodiment the lipophilic substituent is attached to a lysine.

In a further alternative, the lipophilic substituent may be attached to the GLP-2 peptide by means of a spacer in such a way that a carboxyl group of the spacer forms an amide bond with an amino group of the GLP-2 peptide. A spacer must contain at least two functional groups, one to attach to a functional group of the lipophilic substituent and the other to a functional group of the parent GLP-2 peptide. The term "spacer" is used in the present text to designate a bivalent moiety which contain at least two functional groups, one to attach to a functional group of the lipophilic substituent and the other to a functional group of the GLP-2 compound. Examples of suitable spacers are succinic acid, lysyl, glutamyl, asparagyl, glycyl, beta-alanyl and gamma-aminobutanoyl, or a dipeptide such as Gly-Lys, each of which constitutes an individual embodiment. When the spacer is succinic acid, one carboxyl group thereof may form an amide bond with an amino group of the amino acid residue, and the other carboxyl group thereof may form an amide bond with an amino group of the lipophilic substituent. When the spacer is lysyl, glutamyl, asparagyl, glycyl, beta-alanyl or gamma-aminobutanoyl, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the $\epsilon$-amino group of Lys and the lipophilic substituent. In one preferred embodiment, such a further spacer is succinic acid which forms an amide bond with the $\epsilon$-amino group of Lys and with an amino group present in the lipophilic substituent. In another preferred embodiment such a further spacer is Glu or Asp which forms an amide bond with the $\epsilon$-amino group of Lys and another amide bond with a carboxyl group present in the lipophilic substituent, that is, the lipophilic substituent is a $N^{\epsilon}$acylated lysine residue. In an embodiment, the spacer is an amino acid residue except Cys or Met, or a dipeptide such as Gly-Lys. For purposes of the present invention, the phrase "a dipeptide such as Gly-Lys" means any combination of two amino acids except Cys or Met, typically a dipeptide wherein the C-terminal amino acid residue is Lys, His or Trp, typically Lys, and the N-terminal amino acid residue is Ala, Arg, Asp, Asn, Gly, Glu, Gln, Ile, Leu, Val, Phe, Pro, Ser, Tyr, Thr, Lys, His and Trp. Typically, an amino group of the GLP-2 compound forms an amide bond with a carboxylic group of the amino acid residue or dipeptide spacer, and an amino group of the amino acid residue or dipeptide spacer forms an amide bond with a carboxyl group of the lipophilic substituent.

In a further embodiment of the invention the lipophilic substituent has from 8 to 40 carbon atoms. In a further embodiment of the invention the lipophilic substituent has from 10 to 24 carbon atoms. In a further embodiment of the invention the lipophilic substituent has from 12 to 24 carbon atoms. In a further embodiment of the invention the lipophilic substituent has from 12 to 18 carbon atoms. In a further embodiment of the invention the lipophilic substituent has from 14 to 18 carbon atoms.

In a further embodiment of the invention the spacer is present. In a further embodiment of the invention the spacer is selected from an amino acid. In a further embodiment of the invention, the spacer is an amino acid residue except Cys or Met. In another embodiment, the spacer is a dipeptide such as Gly-Lys. In a further embodiment the spacer is selected from lysyl, glutamyl, asparagyl, glycyl, beta-alanyl and gamma-aminobutanoyl, each of which constitutes an individual embodiment. Typically used spacers are glutamyl, aminobutyroyl, and beta-alanyl (beta-Ala).

In another embodiment, the spacer is an unbranched alkane $\alpha,\omega$-dicarboxylic acid group having from 1 to 7 methylene groups, which spacer forms a bridge between an amino group of the parent peptide and an amino group of the lipophilic substituent. Typically, the spacer is succinic acid.

The lipophilic substituent(s) contain a functional group which can be attached to one of the following functional groups of an amino acid of the parent GLP-2 peptide:
- (a) the amino group attached to the alpha-carbon of the N-terminal amino acid,
- (b) the carboxy group attached to the alpha-carbon of the C-terminal amino acid,
- (c) the epsilon-amino group of any Lys residue,
- (d) the carboxy group of the R group of any Asp and Glu residue,
- (e) the hydroxy group of the R group of any Tyr, Ser and Thr residue,
- (f) the amino group of the R group of any Trp, Asn, Gln, Arg, and His residue, or
- (g) the thiol group of the R group of any Cys residue.

In a further embodiment of the invention, the lipophilic substituent is attached to the carboxy group of the R group of any Asp and Glu residue.

In a further embodiment of the invention, a lipophilic substituent is attached to the carboxy group attached to the alpha-carbon of the C-terminal amino acid.

In a further embodiment of the invention, a lipophilic substituent is attached to the epsilon-amino group of any Lys residue.

Each lipophilic substituent contains a functional group which may be attached to a functional group of an amino acid of the parent GLP-2 peptide. For example, a lipophilic substituent may contain a carboxyl group which can be attached to an amino group of the parent GLP-2 peptide by means of an amide bond.

In a further embodiment of the invention, the lipophilic substituent comprises a partially or completely hydrogenated cyclopentanophenathrene skeleton.

In a further embodiment of the invention, the lipophilic substituent is a straight chain or branched alkyl group.

In a further embodiment of the invention, the lipophilic substituent is an acyl group of a straight-chain or branched fatty acid.

In a further embodiment of the invention the lipophilic substituent is an acyl group having the formula $CH_3(CH_2)_nCO-$, wherein n is an integer from 4 to 38. In a further embodiment n is an integer from 12 to 38. In further embodiments the lipophilic substituent is selected from the following individual embodiments $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$. In a specific embodiment, the lipophilic substituent is tetradecanoyl. In another specific embodiment, the lipophilic substituent is hexadecanoyl.

In another embodiment of the present invention, the lipophilic substituent has a group which is negatively charged such as a carboxylic acid group. For example, the lipophilic substituent may be an acyl group of a straight-chain or branched alkane α,ω-dicarboxylic acid of the formula $HOOC(CH_2)_mCO-$, wherein m is an integer from 4 to 38, preferably an integer from 12 to 38, and most preferably is $HOOC(CH_2)_{14}CO-$, $HOOC(CH_2)_{16}CO-$, $HOOC(CH_2)_{18}CO-$, $HOOC(CH_2)_{20}CO-$ or $HOOC(CH_2)_{22}CO-$.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.0.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.1.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.1.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.1.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.1.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.1.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.0

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.0.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 5 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 5 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), glycylglycine, 16.0 mg/ml glycerol, and 5 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), glycylglycine, 16.0 mg/ml glycerol, and 5 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), glycylglycine, 16.0 mg/ml glycerol, and 5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), glycylglycine, 16.0 mg/ml glycerol, and 7 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), glycylglycine, 16.0 mg/ml glycerol, and 7 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), glycylglycine, 16.0 mg/ml glycerol, and 7 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 38.5 mg/ml mannitol, and either 3 mg/ml m-cresol or 1.5 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 38.5 mg/ml mannitol, and either 3 mg/ml m-cresol or 1.5 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 38.5 mg/ml mannitol, and either 3 mg/ml m-cresol or 1.5 mg/ml phenol, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 38.5 mg/ml mannitol, and either 3 mg/ml m-cresol or 1.5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 8.8.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 8.8.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 8.8.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 8.8.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, and 5 mg/ml phenol, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, and 5 mg/ml phenol, at pH 9.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, and 5 mg/ml phenol, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, and 5 mg/ml phenol, at pH 9.4.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 5 mg/ml phenol, and 1 mg/ml EDTA/1.55 mg/ml L-His, at pH 9.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 8.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 8.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, and 5 mg/ml phenol, at pH 8.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.0.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.1.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.1.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.1.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.1.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.1.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.0

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.0.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.1.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.1.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.1.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.1.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.1.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 5 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 5 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), glycylglycine, 16.0 mg/ml glycerol, and 5 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), glycylglycine, 16.0 mg/ml glycerol, and 5 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), glycylglycine, 16.0 mg/ml glycerol, and 5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), glycylglycine, 16.0 mg/ml glycerol, and 7 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), glycylglycine, 16.0 mg/ml glycerol, and 7 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), glycylglycine, 16.0 mg/ml glycerol, and 7 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 38.5 mg/ml mannitol, and either 3 mg/ml m-cresol or 1.5 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 38.5 mg/ml mannitol, and either 3 mg/ml m-cresol or 1.5 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 38.5 mg/ml mannitol, and either 3 mg/ml m-cresol or 1.5 mg/ml phenol, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 38.5 mg/ml mannitol, and either 3 mg/ml m-cresol or 1.5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 7.8.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 7.8.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 7.8.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 17.0 mg/ml mannitol, and 18 mg/ml benzylalcohol, at pH 7.8.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, and 5 mg/ml phenol, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, and 5 mg/ml phenol, at pH 9.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, and 5 mg/ml phenol, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, and 5 mg/ml phenol, at pH 9.4.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 5 mg/ml phenol, and 1 mg/ml EDTA/1.55 mg/ml L-His, at pH 9.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, and 5 mg/ml phenol, at pH 7.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 5 mg/ml phenol, and 1.55 mg/ml L-His, at pH 7.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.0.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.1.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.1.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.1.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.1.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.1.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.0

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.0.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.1.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.1.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.1.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.1.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.1.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 5 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 5 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), glycylglycine, 16.0 mg/ml glycerol, and 5 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), glycylglycine, 16.0 mg/ml glycerol, and 5 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), glycylglycine, 16.0 mg/ml glycerol, and 5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), glycylglycine, 16.0 mg/ml glycerol, and 7 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), glycylglycine, 16.0 mg/ml glycerol, and 7 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), glycylglycine, 16.0 mg/ml glycerol, and 7 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 38.5 mg/ml mannitol, 10 mg/ml sucrose, and either 3 mg/ml m-cresol or 1.5 mg/ml phenol, at pH 8.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 38.5 mg/ml mannitol, 10 mg/ml sucrose, and either 3 mg/ml m-cresol or 1.5 mg/ml phenol, at pH 8.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 38.5 mg/ml mannitol, 10 mg/ml sucrose, and either 3 mg/ml m-cresol or 1.5 mg/ml phenol, at pH 8.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 38.5 mg/ml mannitol, 10 mg/ml sucrose, and either 3 mg/ml m-cresol or 1.5 mg/ml phenol, at pH 8.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 8.8.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 8.8.

Typically the invention relates to a pharmaceutical formulation consisting of an aqueous solution of 3 mg/ml L17K(3-

(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 8.8.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 8.8.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 10 mg/ml sucrose, and 5 mg/ml phenol, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 10 mg/ml sucrose, and 5 mg/ml phenol, at pH 9.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 10 mg/ml sucrose, and 5 mg/ml phenol, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 10 mg/ml sucrose, and 5 mg/ml phenol, at pH 9.4.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 1 mg/ml EDTA or 1.55 mg/ml L-His, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 10 mg/ml sucrose, 5 mg/ml phenol, and 1 mg/ml EDTA/1.55 mg/ml L-His, at pH 9.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 8.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 8.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 1 mg/ml EDTA or 1.55 mg/ml L-His, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 1 mg/ml EDTA or 1.55 mg/ml L-His, at pH 9.4.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 16.0 mg/ml glycerol, and 7 mg/ml phenol, at pH 8.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 8.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 8.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.0.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.1.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.1.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.1.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.1.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.1.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.0

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.0.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.1.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.1.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.1.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.1.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.1.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 5 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 5 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), glycylglycine, 16.0 mg/ml glycerol, and 5 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), glycylglycine, 16.0 mg/ml glycerol, and 5 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), glycylglycine, 16.0 mg/ml glycerol, and 5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), glycylglycine, 16.0 mg/ml glycerol, and 7 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), glycylglycine, 16.0 mg/ml glycerol, and 7 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), glycylglycine, 16.0 mg/ml glycerol, and 7 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 38.5 mg/ml mannitol, 10 mg/ml sucrose, and either 3 mg/ml m-cresol or 1.5 mg/ml phenol, at pH 7.0.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 38.5 mg/ml mannitol, 10 mg/ml sucrose, and either 3 mg/ml m-cresol or 1.5 mg/ml phenol, at pH 7.0.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 38.5 mg/ml mannitol, 10 mg/ml sucrose, and either 3 mg/ml m-cresol or 1.5 mg/ml phenol, at pH 7.0.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 38.5 mg/ml mannitol, 10 mg/ml sucrose, and either 3 mg/ml m-cresol or 1.5 mg/ml phenol, at pH 7.0.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 7.8.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 7.8.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 7.8.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate/sodium dihydrogen phosphate, 17.0 mg/ml mannitol, 10 mg/ml sucrose, and 18 mg/ml benzylalcohol, at pH 7.8.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 10 mg/ml sucrose, and 5 mg/ml phenol, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 10 mg/ml sucrose, and 5 mg/ml phenol, at pH 9.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 10 mg/ml sucrose, and 5 mg/ml phenol, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 10 mg/ml sucrose, and 5 mg/ml phenol, at pH 9.4.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 1 mg/ml EDTA or 1.55 mg/ml L-His, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 10 mg/ml sucrose, 5 mg/ml phenol, and 1 mg/ml EDTA/1.55 mg/ml L-His, at pH 9.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 1 mg/ml EDTA or 1.55 mg/ml L-His, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 1 mg/ml EDTA or 1.55 mg/ml L-His, at pH 9.4.

Typically the invention relates to a pharmaceutical formulation consisting of an aqueous solution of 1 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 2 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 3 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 5 mg/ml L17K(3-(hexadecanoylamino)propionyl)/K30R-GLP-2(1-33), glycine, 36.9 mg/ml mannitol, 10 mg/ml sucrose, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 16.0 mg/ml glycerol, and 7 mg/ml phenol, at pH 7.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, and 5 mg/ml phenol, at pH 7.4.

Typically the invention relates to a pharmaceutical formulation consisting of an aqueous solution of 1 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.4.

Typically the invention relates to a pharmaceutical formulation consisting of an aqueous solution of 2 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.4.

Typically the invention relates to a pharmaceutical formulation consisting of an aqueous solution of 3 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.4.

Typically the invention relates to a pharmaceutical formulation consisting of an aqueous solution of 5 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.4.

Typically the invention relates to a pharmaceutical formulation consisting of an aqueous solution of 7 mg/ml L17K(3-(hexadecanoylamino)propionyl)/K30R-GLP-2(1-33), disodium hydrogen phosphate, 36.9 mg/ml mannitol, 10 mg/ml sucrose, 5 mg/ml phenol, and 1.55 mg/ml L-His, at pH 7.4.

Typically the invention relates to a pharmaceutical formulation consisting of an aqueous solution, wherein the disodium hydrogen phosphate is present in a concentration of 8 mM.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

Exemplary Aspects of the Invention:

1. A GLP-2 peptide comprising the amino acid sequence of formula I

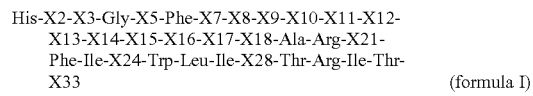
(formula I)

or a fragment thereof (e.g., a fragment of at least about 10 amino acids thereof, at least about 15 amino acids thereof, at least about 20 amino acids thereof, or at least about 25 amino acids thereof, and preferably, a biologically active fragment thereof (e.g., a fragment that exhibits GLP-2 activity) and, more preferably, a therapeutically effective fragment thereof); wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X21 is Asp, or Lys; X24 is Asn, or Lys; X28 is Gln, or Lys; X33 is Asp, Glu, or Lys.

2. The GLP-2 peptide according to embodiment 1, consisting of the amino acid sequence

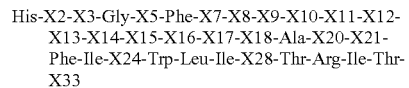

or a fragment thereof; wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X20 is Arg, or Lys; X21 is Asp, or Lys; X24 is Asn, or Lys; X28 is Gln, or Lys; X33 is Asp, Glu, or Lys.

3. The GLP-2 peptide according to embodiments 1 or 2, wherein X2 is Ala.
4. The GLP-2 peptide according to embodiments 1 or 2, wherein X2 is Gly.
5. The GLP-2 peptide according to any of embodiments 1-4, wherein X3 is Asp.
6. The GLP-2 peptide according to any of embodiments 1-4, wherein X3 is Glu.
7. The GLP-2 peptide according to any of embodiments 1-6, wherein X5 is Ser.
8. The GLP-2 peptide according to any of embodiments 1-7, wherein X7 is Ser.
9. The GLP-2 peptide according to any of embodiments 1-8, wherein X8 is Asp.
10. The GLP-2 peptide according to any of embodiments 1-8, wherein X8 is Glu.
11. The GLP-2 peptide according to any of embodiments 1-10, wherein X9 is Asp.
12. The GLP-2 peptide according to any of embodiments 1-10, wherein X9 is Glu.
13. The GLP-2 peptide according to any of embodiments 1-12, wherein X10 is selected from the group consisting of Met, Leu, Ile, and Nor-Leucine.
14. The GLP-2 peptide according to any of embodiments 1-13, wherein X11 is Asn.
15. The GLP-2 peptide according to any of embodiments 1-14, wherein X12 is Thr.

16. The GLP-2 peptide according to any of embodiments 1-15, wherein X13 is Ile.
17. The GLP-2 peptide according to any of embodiments 1-16, wherein X14 is Leu.
18. The GLP-2 peptide according to any of embodiments 1-17, wherein X15 is Asp.
19. The GLP-2 peptide according to any of embodiments 1-18, wherein X16 is Asn.
20. The GLP-2 peptide according to any of embodiments 1-19, wherein X17 is Leu.
21. The GLP-2 peptide according to any of embodiments 1-20, wherein X18 is Ala.
22. The GLP-2 peptide according to any of embodiments 1-21, wherein X21 is Asp.
23. The GLP-2 peptide according to any of embodiments 1-22, wherein X24 is Asn.
24. The GLP-2 peptide according to any of embodiments 1-23, wherein X28 is Gln.
25. The GLP-2 peptide according to any of embodiments 1-24, wherein X33 is Asp.
26. The GLP-2 peptide according to any of embodiments 1-24, wherein X33 is Glu.
27. The GLP-2 peptide according to any of embodiments 1-26, wherein at least one amino acid independently selected from the list consisting of X5, X7, X8, X9, X10, X11, X12, X13, X14, X15, X16, X17, X18, X20, X21, X24, X28, and X33 is a Lys.
28. The GLP-2 peptide according to any of embodiments 1-27, wherein a total of up to 5 amino acid residues have been exchanged with any α-amino acid residue, such as 4 amino acid residues, 3 amino acid residues, 2 amino acid residues, or 1 amino acid residue.
29. The GLP-2 peptide according to embodiment 1, wherein the peptide is selected from the list consisting of
K30R-GLP-2(1-33);
S5K-GLP-2(1-33);
S7K-GLP-2(1-33);
D8K-GLP-2(1-33);
E9K-GLP-2(1-33);
M10K-GLP-2(1-33);
N11K-GLP-2(1-33);
T12K-GLP-2(1-33);
I13K-GLP-2(1-33);
L14K-GLP-2(1-33);
D15K-GLP-2(1-33);
N16K-GLP-2(1-33);
L17K-GLP-2(1-33);
A18K-GLP-2(1-33);
D21K-GLP-2(1-33);
N24K-GLP-2(1-33);
Q28K-GLP-2(1-33);
S5K/K30R-GLP-2(1-33);
S7K/K30R-GLP-2(1-33);
D8K/K30R-GLP-2(1-33);
E9K/K30R-GLP-2(1-33);
M10K/K30R-GLP-2(1-33);
N11K/K30R-GLP-2(1-33);
T12K/K30R-GLP-2(1-33);
I13K/K30R-GLP-2(1-33);
L14K/K30R-GLP-2(1-33);
D15K/K30R-GLP-2(1-33);
N16K/K30R-GLP-2(1-33);
L17K/K30R-GLP-2(1-33);
A18K/K30R-GLP-2(1-33);
D21K/K30R-GLP-2(1-33);
N24K/K30R-GLP-2(1-33);
Q28K/K30R-GLP-2(1-33);
K30R/D33K-GLP-2(1-33);
D3E/K30R/D33E-GLP-2(1-33);
D3E/S5K/K30R/D33E-GLP-2(1-33);
D3E/S7K/K30R/D33E-GLP-2(1-33);
D3E/D8K/K30R/D33E-GLP-2(1-33);
D3E/E9K/K30R/D33E-GLP-2(1-33);
D3E/M10K/K30R/D33E-GLP-2(1-33);
D3E/N11K/K30R/D33E-GLP-2(1-33);
D3E/T12K/K30R/D33E-GLP-2(1-33);
D3E/I13K/K30R/D33E-GLP-2(1-33);
D3E/L14K/K30R/D33E-GLP-2(1-33);
D3E/D15K/K30R/D33E-GLP-2(1-33);
D3E/N16K/K30R/D33E-GLP-2(1-33);
D3E/L17K/K30R/D33E-GLP-2(1-33);
D3E/A18K/K30R/D33E-GLP-2(1-33);
D3E/D21K/K30R/D33E-GLP-2(1-33);
D3E/N24K/K30R/D33E-GLP-2(1-33); and
D3E/Q28K/K30R/D33E-GLP-2(1-33).
30. A polynucleotide construct encoding a GLP-2 peptide according to any of embodiments 1-29.
31. A host cell comprising the polynucleotide construct according to embodiment 30.
32. The host cell according to embodiment 31, which is a eukaryotic cell.
33. The host cell according to embodiment 32, wherein the cell is a yeast cell.
34. A GLP-2 derivative comprising a GLP-2 peptide, wherein a lipophilic substituent is attached to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28 with the proviso that said lipophilic substituent is not attached at the N-terminal amino acid residue or the C-terminal amino acid residue of said GLP-2 peptide.
35. The GLP-2 derivative according to embodiment 34, wherein the GLP-2 peptide is according to formula II His-X2-X3-Gly-X5-Phe-X7-X8-X9-X10-X11-X12-X13-X14-X15-X16-X17-X18-Ala-X20-X21-Phe-Ile-X24-Trp-Leu-Ile-X28-Thr-X30-Ile-Thr-X33    (formula II)

or a fragment thereof; wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X20 is Arg, or Lys; X21 is Asp, or Lys; X24 is Asn, or Lys; X28 is Gln, or Lys; X30 is Arg, or Lys; X33 is Asp, Glu, or Lys (formula II).
36. The GLP-2 derivative according to embodiments 34 or 35, wherein the GLP-2 peptide is according to any of embodiments 1-29.
37. The GLP-2 derivative according to any of embodiments 34-36, wherein only one lipophilic substituent is attached to said GLP-2 peptide.
38. The GLP-2 derivative according to any of embodiments 34-37, wherein said lipophilic substituent comprises from 4 to 40 carbon atoms.
39. The GLP-2 derivative according to embodiment 38, wherein said lipophilic substituent comprises from 8 to 25 carbon atoms.
40. The GLP-2 derivative according to embodiment 38, wherein said lipophilic substituent comprises from 12 to 20 carbon atoms.

41. The GLP-2 derivative according to any of embodiments 34-40, wherein said lipophilic substituent is attached to an amino acid residue in such a way that a carboxyl group of the lipophilic substituent forms an amide bond with an amino group of the amino acid residue.
42. The GLP-2 derivative according to embodiment 41, wherein said amino acid residue is a Lys residue.
43. The GLP-2 derivative according to any of embodiments 34-40, wherein said lipophilic substituent is attached to an amino acid residue in such a way that an amino group of the lipophilic substituent forms an amide bond with a carboxyl group of the amino acid residue.
44. The GLP-2 derivative according to any of embodiments 34-43, wherein said lipophilic substituent is attached to said GLP-2 peptide by means of a spacer.
45. The GLP-2 derivative according to embodiment 44, wherein said spacer is an unbranched alkane α,ω-dicarboxylic acid group having from 1 to 7 methylene groups, such as two methylene groups which spacer forms a bridge between an amino group of the GLP-2 peptide and an amino group of said lipophilic substituent.
46. The GLP-2 derivative according to embodiment 44, wherein said spacer is an amino acid residue except a Cys residue, or a dipeptide.
47. The GLP-2 derivative according to embodiment 46, wherein said spacer is selected from the list consisting of β-alanine, gamma-aminobutyric acid (GABA), γ-glutamic acid, Lys, Asp, Glu, a dipeptide containing Asp, a dipeptide containing Glu, or a dipeptide containing Lys.
48. A GLP-2 derivative according to embodiments 46 or 47, wherein a carboxyl group of the parent GLP-2 peptide forms an amide bond with an amino group of said spacer, and the carboxyl group of the amino acid or dipeptide spacer forms an amide bond with an amino group of the lipophilic substituent.
49. A GLP-2 derivative according to embodiments 46 or 47, wherein an amino group of the parent GLP-2 peptide forms an amide bond with a carboxylic group of said spacer, and an amino group of said spacer forms amide bond with a carboxyl group of the lipophilic substituent.
50. A GLP-2 derivative according to any of embodiments 34-49, wherein the lipophilic substituent comprises a partially or completely hydrogenated cyclopentanophenathrene skeleton.
51. A GLP-2 derivative according to any of embodiments 34-50, wherein the lipophilic substituent is an straight-chain or branched alkyl group.
52. A GLP-2 derivative according to any of embodiments 34-50, wherein the lipophilic substituent is the acyl group of a straight-chain or branched fatty acid.
53. A GLP-2 derivative according to embodiment 52, wherein the acyl group is selected from the group comprising $CH_3(CH_2)_nCO-$, wherein n is 4 to 38, such as $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.
54. A GLP-2 derivative according to any of embodiments 34-49, wherein the lipophilic substituent is an acyl group of a straight-chain or branched alkane a,w-dicarboxylic acid.
55. A GLP-2 derivative according to embodiment 59, wherein the acyl group is selected from the group comprising $HOOC(CH_2)_mCO-$, wherein m is 4 to 38, such as $HOOC(CH_2)_{14}CO-$, $HOOC(CH_2)_{16}CO-$, $HOOC(CH_2)_{18}CO-$, $HOOC(CH_2)_{20}CO-$ and $HOOC(CH_2)_{22}CO-$.
56. A GLP-2 derivative according to any of embodiments 34-49, wherein the lipophilic substituent is a group of the formula $CH_3(CH_2)_p((CH_2)_qCOOH)CHNH-CO(CH_2)_2CO-$, wherein p and q are integers and p+q is an integer of from 8 to 40, such as from 12 to 35.
57. A GLP-2 derivative according to any of embodiments 34-49, wherein the lipophlic substituent is a group of the formula $CH_3(CH_2)_rCO-NHCH(COOH)(CH_2)_2CO-$, wherein r is an integer of from 10 to 24.
58. A GLP-2 derivative according to any of embodiments 34-49, wherein the lipophilic substituent is a group of the formula $CH_3(CH_2)_sCO-NHCH((CH_2)_2COOH)CO-$, wherein s is an integer of from 8 to 24.
59. A GLP-2 derivative according to any of embodiments 34-49, wherein the lipophilic substituent is a group of the formula $COOH(CH_2)_tCO-$ wherein t is an integer of from 8 to 24.
60. A GLP-2 derivative according to any of embodiments 34-49, wherein the lipophilic substituent is a group of the formula $-NHCH(COOH)(CH_2)_4NH-CO(CH_2)_uCH_3$, wherein u is an integer of from 8 to 18.
61. A GLP-2 derivative according to any of embodiments 34-49, wherein the lipophilic substituent is a group of the formula $-NHCH(COOH)(CH_2)_4NH-COCH((CH_2)_2COOH)NH-CO(CH_2)_wCH_3$, wherein w is an integer of from 10 to 16.
62. A GLP-2 derivative according to any of embodiments 34-49, wherein the lipophilic substituent is a group of the formula $-NHCH(COOH)(CH_2)_4NH-CO(CH_2)_2CH(COOH)NH-CO(CH_2)_xCH_3$, wherein x is an integer of from 10 to 16.
63. A GLP-2 derivative according to any of embodiments 34-49, wherein the lipophilic substituent is a group of the formula $-NHCH(COOH)(CH_2)_4NH-CO(CH_2)_2CH(COOH)NHCO(CH_2)_yCH_3$, wherein y is zero or an integer of from 1 to 22.
64. A GLP-2 derivative according to any of embodiments 34-63, which has two lipophilic substituents.
65. A GLP-2 derivative according to any of embodiments 34-64, which is selected from the group consisting of
S5K(3-(hexadecanoylamino)propionyl)-GLP-2(1-33);
S7K(3-(hexadecanoylamino)propionyl)-GLP-2(1-33);
D8K(3-(hexadecanoylamino)propionyl)-GLP-2(1-33);
E9K(3-(hexadecanoylamino)propionyl)-GLP-2(1-33);
M10K(3-(hexadecanoylamino)propionyl)-GLP-2(1-33);
N11K(3-(hexadecanoylamino)propionyl)-GLP-2(1-33);
T12K(3-(hexadecanoylamino)propionyl)-GLP-2(1-33);
I13K(3-(hexadecanoylamino)propionyl)-GLP-2(1-33);
L14K(3-(hexadecanoylamino)propionyl)-GLP-2(1-33);
D15K(3-(hexadecanoylamino)propionyl)-GLP-2(1-33);
N16K(3-(hexadecanoylamino)propionyl)-GLP-2(1-33);
L17K(3-(octanoylamino)propionyl)-GLP-2(1-33);
L17K(3-(nonanoylamino)propionyl)-GLP-2(1-33);
L17K(3-(decanoylamino)propionyl)-GLP-2(1-33);
L17K(3-(undecanoylamino)propionyl)-GLP-2(1-33);
L17K(3-(dodecanoylamino)propionyl)-GLP-2(1-33);
L17K(3-(tridecanoylamino)propionyl)-GLP-2(1-33);
L17K(3-(tetradecanoylamino)propionyl)-GLP-2(1-33);
L17K(3-(pentadecanoylamino)propionyl)-GLP-2(1-33);
L17K(3-(hexadecanoylamino)propionyl)-GLP-2(1-33);
L17K(3-(heptadecanoylamino)propionyl)-GLP-2(1-33);
L17K(3-(octadecanoylamino)propionyl)-GLP-2(1-33);
L17K(3-(nonadecanoylamino)propionyl)-GLP-2(1-33);
L17K(3-(eicosanoylamino)propionyl)-GLP-2(1-33);
L17K((S)-4-carboxy-4-(octanoylamino)butanoyl)-GLP-2 (1-33);
L17K((S)-4-carboxy-4-(nonanoylamino)butanoyl)-GLP-2 (1-33);
L17K((S)-4-carboxy-4-(decanoylamino)butanoyl)-GLP-2 (1-33);

L17K((S)-4-carboxy-4-(undecanoylamino)butanoyl)-GLP-2(1-33);
L17K((S)-4-carboxy-4-(dodecanoylamino)butanoyl)-GLP-2(1-33);
L17K((S)-4-carboxy-4-(tridecanoylamino)butanoyl)-GLP-2(1-33);
L17K((S)-4-carboxy-4-(tetradecanoylamino)butanoyl)-GLP-2(1-33);
L17K((S)-4-carboxy-4-(pentadecanoylamino)butanoyl)-GLP-2(1-33);
L17K((S)-4-carboxy-4-(hexadecanoylamino)butanoyl)-GLP-2(1-33);
L17K((S)-4-carboxy-4-(heptadecanoylamino)butanoyl)-GLP-2(1-33);
L17K((S)-4-carboxy-4-(octadecanoylamino)butanoyl)-GLP-2(1-33);
L17K((S)-4-carboxy-4-(nonadecanoylamino)butanoyl)-GLP-2(1-33);
L17K((S)-4-carboxy-4-(eicosanoylamino)butanoyl)-GLP-2(1-33);
L17K(4-(octanoylamino)butanoyl)-GLP-2(1-33);
L17K(4-(nonanoylamino)butanoyl)-GLP-2(1-33);
L17K(4-(decanoylamino)butanoyl)-GLP-2(1-33);
L17K(4-(undecanoylamino)butanoyl)-GLP-2(1-33);
L17K(4-(dodecanoylamino)butanoyl)-GLP-2(1-33);
L17K(4-(tridecanoylamino)butanoyl)-GLP-2(1-33);
L17K(4-(tetradecanoylamino)butanoyl)-GLP-2(1-33);
L17K(4-(pentadecanoylamino)butanoyl)-GLP-2(1-33);
L17K(4-(hexadecanoylamino)butanoyl)-GLP-2(1-33);
L17K(4-(heptadecanoylamino)butanoyl)-GLP-2(1-33);
L17K(4-(octadecanoylamino)butanoyl)-GLP-2(1-33);
L17K(4-(nonadecanoylamino)butanoyl)-GLP-2(1-33);
L17K(4-(eicosanoylamino)butanoyl)-GLP-2(1-33);
A18K(3-(hexadecanoylamino)propionyl)-GLP-2(1-33);
D21K(3-(hexadecanoylamino)propionyl)-GLP-2(1-33);
N24K(3-(hexadecanoylamino)propionyl)-GLP-2(1-33);
Q28K(3-(hexadecanoylamino)propionyl)-GLP-2(1-33);
S5K(3-(hexadecanoylamino)propionyl)/K30R-GLP-2(1-33);
S7K(3-(hexadecanoylamino)propionyl)/K30R-GLP-2(1-33);
D8K(3-(hexadecanoylamino)propionyl)/K30R-GLP-2(1-33);
E9K(3-(hexadecanoylamino)propionyl)/K30R-GLP-2(11-33);
M10K(3-(hexadecanoylamino)propionyl)/K30R-GLP-2(1-33);
N11K(3-(hexadecanoylamino)propionyl)/K30R-GLP-2(1-33);
T12K(3-(hexadecanoylamino)propionyl)/K30R-GLP-2(1-33);
I13K(3-(hexadecanoylamino)propionyl)/K30R-GLP-2(1-33);
L14K(3-(hexadecanoylamino)propionyl)/K30R-GLP-2(1-33);
D15K(3-(hexadecanoylamino)propionyl)/K30R-GLP-2(1-33);
N16K(3-(hexadecanoylamino)propionyl)/K30R-GLP-2(1-33);
L17K(3-(octanoylamino)propionyl)/K30R-GLP-2(1-33);
L17K(3-(nonanoylamino)propionyl)/K30R-GLP-2(1-33);
L17K(3-(decanoylamino)propionyl)/K30R-GLP-2(1-33);
L17K(3-(undecanoylamino)propionyl)/K30R-GLP-2(1-33);
L17K(3-(dodecanoylamino)propionyl)/K30R-GLP-2(1-33);
L17K(3-(tridecanoylamino)propionyl)/K30R-GLP-2(1-33);
L17K(3-(tetradecanoylamino)propionyl)/K30R-GLP-2(1-33);
L17K(3-(pentadecanoylamino)propionyl)/K30R-GLP-2(1-33);
L17K(3-(hexadecanoylamino)propionyl)/K30R-GLP-2(1-33);
L17K(3-(heptadecanoylamino)propionyl)/K30R-GLP-2(1-33);
L17K(3-(octadecanoylamino)propionyl)/K30R-GLP-2(1-33);
L17K(3-(nonadecanoylamino)propionyl)/K30R-GLP-2(1-33);
L17K(3-(eicosanoylamino)propionyl)/K30R-GLP-2(1-33);
L17K((S)-4-carboxy-4-(octanoylamino)butanoyl)/K30R-GLP-2(1-33);
L17K((S)-4-carboxy-4-(nonanoylamino)butanoyl)/K30R-GLP-2(1-33);
L17K((S)-4-carboxy-4-(decanoylamino)butanoyl)/K30R-GLP-2(1-33);
L17K((S)-4-carboxy-4-(undecanoylamino)butanoyl)/K30R-GLP-2(1-33);
L17K((S)-4-carboxy-4-(dodecanoylamino)butanoyl)/K30R-GLP-2(1-33);
L17K((S)-4-carboxy-4-(tridecanoylamino)butanoyl)/K30R-GLP-2(1-33);
L17K((S)-4-carboxy-4-(tetradecanoylamino)butanoyl)/K30R-GLP-2(1-33);
L17K((S)-4-carboxy-4-(pentadecanoylamino)butanoyl)/K30R-GLP-2(1-33);
L17K((S)-4-carboxy-4-(hexadecanoylamino)butanoyl)/K30R-GLP-2(1-33);
L17K((S)-4-carboxy-4-(heptadecanoylamino)butanoyl)/K30R-GLP-2(1-33);
L17K((S)-4-carboxy-4-(octadecanoylamino)butanoyl)/K30R-GLP-2(1-33);
L17K((S)-4-carboxy-4-(nonadecanoylamino)butanoyl)/K30R-GLP-2(1-33);
L17K((S)-4-carboxy-4-(eicosanoylamino)butanoyl)/K30R-GLP-2(1-33);
L17K(4-(octanoylamino)butanoyl)/K30R-GLP-2(1-33);
L17K(4-(nonanoylamino)butanoyl)/K30R-GLP-2(1-33);
L17K(4-(decanoylamino)butanoyl)/K30R-GLP-2(1-33);
L17K(4-(undecanoylamino)butanoyl)/K30R-GLP-2(1-33);
L17K(4-(dodecanoylamino)butanoyl)/K30R-GLP-2(1-33);
L17K(4-(tridecanoylamino)butanoyl)/K30R-GLP-2(1-33);
L17K(4-(tetradecanoylamino)butanoyl)/K30R-GLP-2(1-33);
L17K(4-(pentadecanoylamino)butanoyl)/K30R-GLP-2(1-33);
L17K(4-(hexadecanoylamino)butanoyl)/K30R-GLP-2(1-33);
L17K(4-(heptadecanoylamino)butanoyl)/K30R-GLP-2(1-33);
L17K(4-(octadecanoylamino)butanoyl)/K30R-GLP-2(1-33);
L17K(4-(nonadecanoylamino)butanoyl)/K30R-GLP-2(1-33);
L17K(4-(eicosanoylamino)butanoyl)/K30R-GLP-2(1-33);
A18K(3-(hexadecanoylamino)propionyl)/K30R-GLP-2(1-33);
D21K(3-(hexadecanoylamino)propionyl)/K30R-GLP-2(1-33);
N24K(3-(hexadecanoylamino)propionyl)/K30R-GLP-2(1-33);
Q28K(3-(hexadecanoylamino)propionyl)/K30R-GLP-2(1-33);
D3E/S5K(3-(hexadecanoylamino)propionyl)/K30R/D33E-GLP-2(1-33);

D3E/S7K(3-(hexadecanoylamino)propionyl)/K30R/D33E-GLP-2(1-33);
D3E/D8K(3-(hexadecanoylamino)propionyl)/K30R/D33E-GLP-2(1-33);
D3E/E9K(3-(hexadecanoylamino)propionyl)/K30R/D33E-GLP-2(1-33);
D3E/M10K(3-(hexadecanoylamino)propionyl)/K30R/D33E-GLP-2(1-33);
D3E/N11K(3-(hexadecanoylamino)propionyl)/K30R/D33E-GLP-2(1-33);
D3E/T12K(3-(hexadecanoylamino)propionyl)/K30R/D33E-GLP-2(1-33);
D3E/I13K(3-(hexadecanoylamino)propionyl)/K30R/D33E-GLP-2(1-33);
D3E/L14K(3-(hexadecanoylamino)propionyl)/K30R/D33E-GLP-2(1-33);
D3E/D15K(3-(hexadecanoylamino)propionyl)/K30R/D33E-GLP-2(1-33);
D3E/N16K(3-(hexadecanoylamino)propionyl)/K30R/D33E-GLP-2(1-33);
D3E/L17K(3-(octanoylamino)propionyl)/K30R/D33E-GLP-2(1-33);
D3E/L17K(3-(nonanoylamino)propionyl)/K30R/D33E-GLP-2(1-33);
D3E/L17K(3-(decanoylamino)propionyl)/K30R/D33E-GLP-2(1-33);
D3E/L17K(3-(undecanoylamino)propionyl)/K30R/D33E-GLP-2(1-33);
D3E/L17K(3-(dodecanoylamino)propionyl)/K30R/D33E-GLP-2(1-33);
D3E/L17K(3-(tridecanoylamino)propionyl)/K30R/D33E-GLP-2(1-33);
D3E/L17K(3-(tetradecanoylamino)propionyl)/K30R/D33E-GLP-2(1-33);
D3E/L17K(3-(pentadecanoylamino)propionyl)/K30R/D33E-GLP-2(1-33);
D3E/L17K(3-(hexadecanoylamino)propionyl)/K30R/D33E-GLP-2(1-33);
D3E/L17K(3-(heptadecanoylamino)propionyl)/K30R/D33E-GLP-2(1-33);
D3E/L17K(3-(octadecanoylamino)propionyl)/K30R/D33E-GLP-2(1-33);
D3E/L17K(3-(nonadecanoylamino)propionyl)/K30R/D33E-GLP-2(1-33);
D3E/L17K(3-(eicosanoylamino)propionyl)/K30R/D33E-GLP-2(1-33);
D3E/L17K((S)-4-carboxy-4-(octanoylamino)butanoyl)/K30R/D33E-GLP-2(1-33);
D3E/L17K((S)-4-carboxy-4-(nonanoylamino)butanoyl)/K30R/D33E-GLP-2(1-33);
D3E/L17K((S)-4-carboxy-4-(decanoylamino)butanoyl)/K30R/D33E-GLP-2(1-33);
D3E/L17K((S)-4-carboxy-4-(undecanoylamino)butanoyl)/K30R/D33E-GLP-2(1-33);
D3E/L17K((S)-4-carboxy-4-(dodecanoylamino)butanoyl)/K30R/D33E-GLP-2(1-33);
D3E/L17K((S)-4-carboxy-4-(tridecanoylamino)butanoyl)/K30R/D33E-GLP-2(1-33);
D3E/L17K((S)-4-carboxy-4-(tetradecanoylamino)butanoyl)/K30R/D33E-GLP-2(1-33);
D3E/L17K((S)-4-carboxy-4-(pentadecanoylamino)butanoyl)/K30R/D33E-GLP-2(1-33);
D3E/L17K((S)-4-carboxy-4-(hexadecanoylamino)butanoyl)/K30R/D33E-GLP-2(1-33);
D3E/L17K((S)-4-carboxy-4-(heptadecanoylamino)butanoyl)/K30R/D33E-GLP-2(11-33);
D3E/L17K((S)-4-carboxy-4-(octadecanoylamino)butanoyl)/K30R/D33E-GLP-2(1-33);
D3E/L17K((S)-4-carboxy-4-(nonadecanoylamino)butanoyl)/K30R/D33E-GLP-2(1-33);
D3E/L17K((S)-4-carboxy-4-(eicosanoylamino)butanoyl)/K30R/D33E-GLP-2(1-33);
D3E/L17K(4-(octanoylamino)butanoyl)/K30R/D33E-GLP-2(1-33);
D3E/L17K(4-(nonanoylamino)butanoyl)/K30R/D33E-GLP-2(1-33);
D3E/L17K(4-(decanoylamino)butanoyl)/K30R/D33E-GLP-2(1-33);
D3E/L17K(4-(undecanoylamino)butanoyl)/K30R/D33E-GLP-2(1-33);
D3E/L17K(4-(dodecanoylamino)butanoyl)/K30R/D33E-GLP-2(1-33);
D3E/L17K(4-(tridecanoylamino)butanoyl)/K30R/D33E-GLP-2(1-33);
D3E/L17K(4-(tetradecanoylamino)butanoyl)/K30R/D33E-GLP-2(1-33);
D3E/L17K(4-(pentadecanoylamino)butanoyl)/K30R/D33E-GLP-2(1-33);
D3E/L17K(4-(hexadecanoylamino)butanoyl)/K30R/D33E-GLP-2(1-33);
D3E/L17K(4-(heptadecanoylamino)butanoyl)/K30R/D33E-GLP-2(1-33);
D3E/L17K(4-(octadecanoylamino)butanoyl)/K30R/D33E-GLP-2(1-33);
D3E/L17K(4-(nonadecanoylamino)butanoyl)/K30R/D33E-GLP-2(1-33);
D3E/L17K(4-(eicosanoylamino)butanoyl)/K30R/D33E-GLP-2(1-33);
D3E/A18K(3-(hexadecanoylamino)propionyl)/K30R/D33E-GLP-2(1-33);
D3E/D21 K(3-(hexadecanoylamino)propionyl)/K30R/D33E-GLP-2(1-33);
D3E/N24K(3-(hexadecanoylamino)propionyl)/K30R/D33E-GLP-2(1-33); and D3E/Q28K(3-(hexadecanoylamino)propionyl)/K30R/D33E-GLP-2(1-33).

66. A pharmaceutical composition comprising a GLP-2 derivative comprising a GLP-2 peptide, wherein a lipophilic substituent is attached to one or more amino acid residues at a position relative to the amino acid sequence of SEQ ID NO:1 selected from the list consisting of S5, S7, D8, E9, M10, N11, T12, I13, L14, D15, N16, L17, A18, D21, N24, and Q28 with the proviso that said lipophilic substituent is not attached at the N-terminal amino acid residue or the C-terminal amino acid residue of said GLP-2 peptide.

67. A pharmaceutical composition comprising a GLP-2 derivative as defined in any of embodiments 34-65, and, optionally, a pharmaceutically acceptable carrier.

68. Use of a GLP-2 derivative as defined in any of embodiments 34-65 for the preparation of a medicament.

69. Use of a GLP-2 derivative as defined in any of embodiments 34-65 for the preparation of a medicament with protracted effect.

70. Use of a GLP-2 derivative as defined in any of embodiments 34-65 for the preparation of a medicament for the treatment of intestinal failure or other condition leading to malabsorption of nutrients in the intestine.

71. Use of a GLP-2 derivative as defined in any of embodiments 34-65 for the preparation of a medicament for the treatment of small bowel syndrome, Inflammatory bowel syndrome, Crohns disease, colitis including collagen colitis, radiation colitis, ulcerative colitis chronic radiation enteritis, non-tropical (gluten intolerance) and tropical sprue, Coeliac disease (gluten sensitive enteropathy), damaged tissue after vascular obstruction or trauma, diarrhea e.g. tourist diarrhea and post-infective diarrhea, chronic bowel dysfunction, dehydration, bacteremia, sepsis, anorexia nervosa, damaged tissue after chemotherapy e.g. chemotherapy-induced intestinal mucositis, premature infants incl. intestinal failure in premature infants, preborn infants incl. intestinal failure in preborn infants, scleroderma, gastritis including atrophic gastritis, postantrectomy atrophic gastritis and helicobacter pylori gastritis, pancreatitis, general septic shock ulcers, enteritis, cul-de-sac, lymphatic obstruction, vascular disease and graft-versus-host, healing after surgical procedures, post radiation atrophy and chemotherapy, weight loss in Parkinson's Disease, intestinal adaptation after surgical procedure, parenteral nutrition-induced mucosal atrophy, e.g. total parenteral nutrition (TPN)-induced mucosal atrophy, and bone-related disorders including osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, or glucocorticoid-induced osteoporosis.

72. A method for the treatment of intestinal failure or other condition leading to malabsorption of nutrients in the intestine, the method comprising administering a therapeutically or prophylactically effective amount of a GLP-2 derivative as defined in any of embodiments 34-65; to a subject in need thereof.

73. A method for the treatment of small bowel syndrome, Inflammatory bowel syndrome, Crohns disease, colitis including collagen colitis, radiation colitis, ulcerative colitis chronic radiation enteritis, non-tropical (gluten intolerance) and tropical sprue, Coeliac disease (gluten sensitive enteropathy), damaged tissue after vascular obstruction or trauma, diarrhea e.g. tourist diarrhea and post-infective diarrhea, chronic bowel dysfunction, dehydration, bacteremia, sepsis, anorexia nervosa, damaged tissue after chemotherapy e.g. chemotherapy-induced intestinal mucositis, premature infants incl. intestinal failure in premature infants, preborn infants incl. intestinal failure in preborn infants, scleroderma, gastritis including atrophic gastritis, postantrectomy atrophic gastritis and helicobacter pylori gastritis, pancreatitis, general septic shock ulcers, enteritis, cul-de-sac, lymphatic obstruction, vascular disease and graft-versus-host, healing after surgical procedures, post radiation atrophy and chemotherapy, weight loss in Parkinson's Disease, intestinal adaptation after surgical procedure, parenteral nutrition-induced mucosal atrophy, e.g. total parenteral nutrition (TPN)-induced mucosal atrophy, and bone-related disorders including osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, Bechet's disease, osteomalacia, hyperostosis, osteopetrosis, metastatic bone disease, immobilization-induced osteopenia, or glucocorticoid-induced osteoporosis, the method comprising administering a therapeutically or prophylactically effective amount of a GLP-2 derivative as defined in any of embodiments 34-65; to a subject in need thereof.

74. A method for producing the GLP-2 peptide defined in any of embodiments 1-29, the method comprising cultivating a host cell as defined in any one of embodiments 31-33 in an appropriate growth medium under conditions allowing expression of the polynucleotide construct and recovering the resulting peptide from the culture medium.

Further Embodiments

1b. A pharmaceutical formulation comprising a GLP-2 compound, and a buffer, wherein said GLP-2 compound is present in a concentration from 0.1 mg/ml to 100 mg/ml, and wherein said formulation has a pH from 8.0 to 10, or a freeze-dried formulation thereof.

2b. The formulation according to embodiment 1b, further comprising water.

3b. A pharmaceutical formulation comprising an aqueous solution of a GLP-2 compound, and a buffer, wherein said GLP-2 compound is present in a concentration from 0.1 mg/ml to 100 mg/ml, and wherein said formulation has a pH from 8.0 to 10.

4b. The formulation according to any one of embodiments 1b-3b, wherein said GLP-2 compound is present in a concentration from 1 mg/ml to 100 mg/ml.

5b. The formulation according to any one of embodiments 1b-4b, wherein said formulation has a pH from 8.5 to 10.

6b. The formulation according to any one of embodiments 1b-5b, wherein said formulation has a pH from 9.0 to 10.

7b. The formulation according to any one of embodiments 1b-6b, wherein the GLP-2 compound is present in a concentration from 0.1 mg/ml to 80 mg/ml, 0.1 mg/ml to 50 mg/ml, 0.1 mg/ml to 20 mg/ml, 0.1 mg/ml to 10 mg/ml, typically from 0.1-5 mg/ml.

8b. The formulation according to any one of embodiments 1b-7b, wherein the GLP-2 compound is present in a concentration from 1 mg/ml to 80 mg/ml, 1 mg/ml to 50 mg/ml, 1 mg/ml to 20 mg/ml, 1 mg/ml to 10 mg/ml, typically from 1-5 mg/ml.

9b. The formulation according to any one of embodiments 1b-8b, further comprising a preservative.

10b. The formulation according to embodiment 9b, wherein said preservative is present in a concentration from 0.1 mg/ml to 20 mg/ml.

11b. The formulation according to any one of embodiments 1b-10b, further comprising an isotonic agent.

12b. The formulation according to embodiment 11b, wherein said isotonic agent is present in a concentration from 1 mg/ml to 50 mg/ml.

13b. The formulation according to any one of embodiments 1b-12b, further comprising a chelating agent.

14b. The formulation according to embodiment 13b, wherein said chelating agent is present in a concentration from 0.1 mg/ml to 5 mg/ml.

15b. The formulation according to any one of embodiments 1b-14b, further comprising a stabiliser.

16b. The formulation according to embodiment 15b, wherein said stabiliser is selected from the group consisting of L-histidine, imidazole and arginine.

17b. The formulation according to embodiment 16b, wherein said stabiliser is a high molecular weight polymer and/or a low molecular weight compound and is present in a concentration from 0.1 mg/ml to 50 mg/ml.

18b. The formulation according to any one of embodiments 1b-17b, further comprising a surfactant.

19b. The formulation according to any one of embodiments 1b-18b, wherein said GLP-2 compound is selected from list consisting of GLP-2(1-33), A2G-GLP-2(1-33), and analogs thereof.

20b. The formulation according to any one of embodiments 1b-18b, wherein said GLP-2 compound is a GLP-2 derivative.

21b. The formulation according to embodiment 20b, wherein said GLP-2 derivative is a GLP-2 peptide, wherein an amino acid residue of the parent peptide has a lipophilic substituent attached, optionally via a spacer.

22b. The formulation according to embodiment 21b, wherein said GLP-2 derivative is a GLP-2 peptide, wherein a lipophilic substituent is attached to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28.

23b. The formulation according to embodiment 22b, wherein the GLP-2 peptide is according to formula II His-X2-X3-Gly-X5-Phe-X7-X8-X9-X10-X11-X12-X13-X14-X15-X16-X17-X18-Ala-X20-X21-Phe-Ile-X24-Trp-Leu-Ile-X28-Thr-X30-Ile-Thr-X33   (formula II)

or a fragment thereof; wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X20 is Arg, or Lys; X21 is Asp, or Lys; X24 is Asn, or Lys; X28 is Gln, or Lys; X30 is Arg, or Lys; X33 is Asp, Glu, or Lys (formula II).

24b. The formulation according to any of embodiments 22b or 23b, wherein the GLP-2 peptide comprises the amino acid sequence of formula I His-X2-X3-Gly-X5-Phe-X7-X8-X9-X10-X11-X12-X13-X14-X15-X16-X17-X18-Ala-Arg-X21-Phe-Ile-X24-Trp-Leu-Ile-X28-Thr-Arg-Ile-Thr-X33   (formula I)

or a fragment thereof; wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X21 is Asp, or Lys; X24 is Asn, or Lys; X28 is Gln, or Lys; X33 is Asp, Glu, or Lys.

25b. The formulation according to any one of embodiments 22b-24b, wherein the GLP-2 peptide consists of the amino acid sequence His-X2-X3-Gly-X5-Phe-X7-X8-X9-X10-X11-X12-X13-X14-X15-X16-X17-X18-Ala-X20-X21-Phe-Ile-X24-Trp-Leu-Ile-X28-Thr-Arg-Ile-Thr-X33 or a fragment thereof; wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X20 is Arg, or Lys; X21 is Asp, or Lys; X24 is Asn, or Lys; X28 is Gln, or Lys; X33 is Asp, Glu, or Lys.

26b. The formulation according to any one of embodiments 23b-25b, wherein X2 is Ala.

27b. The formulation according to any one of embodiments 23b-25b, wherein X2 is Gly.

28b. The formulation according to any one of embodiments 23b-27b, wherein X3 is Asp.

29b. The formulation according to any one of embodiments 23b-27b, wherein X3 is Glu.

30b. The formulation according to any one of embodiments 23b-29b, wherein X5 is Ser.

31b. The formulation according to any one of embodiments 23b-30b, wherein X7 is Ser.

32b. The formulation according to any one of embodiments 23b-31b, wherein X8 is Asp.

33b. The formulation according to any one of embodiments 23b-31b, wherein X8 is Glu.

34b. The formulation according to any one of embodiments 23-33, wherein X9 is Asp.

35b. The formulation according to any one of embodiments 23b-33b, wherein X9 is Glu.

36b. The formulation according to any one of embodiments 23b-35b, wherein X10 is selected from the group consisting of Met, Leu, Ile, and Nor-Leucine.

37b. The formulation according to any one of embodiments 23b-36b, wherein X11 is Asn.

38b. The formulation according to any one of embodiments 23b-37b, wherein X12 is Thr.

39b. The formulation according to any one of embodiments 23b-38b, wherein X13 is Ile.

40b. The formulation according to any one of embodiments 23b-39b, wherein X14 is Leu.

41b. The formulation according to any one of embodiments 23b-40b, wherein X15 is Asp.

42b. The formulation according to any one of embodiments 23b-41b, wherein X16 is Asn.

43b. The formulation according to any one of embodiments 23b-42b, wherein X17 is Leu.

44b. The formulation according to any one of embodiments 23b-43b, wherein X18 is Ala.

45b. The formulation according to any one of embodiments 23b-44b, wherein X21 is Asp.

46b. The formulation according to any one of embodiments 23b-45b, wherein X24 is Asn.

47b. The formulation according to any one of embodiments 23b-46b, wherein X28 is Gln.

48b. The formulation according to any one of embodiments 23b-47b, wherein X33 is Asp.

49b. The formulation according to any one of embodiments 23b-47b, wherein X33 is Glu.

50b. The formulation according to any one of embodiments 23b-25b, wherein at least one amino acid independently selected from the list consisting of X5, X7, X8, X9, X10, X11, X12, X13, X14, X15, X16, X17, X18, X20, X21, X24, X28, and X33 is a Lys.

51b. The formulation according to any one of embodiments 21b-50b, wherein a total of up to 5 amino acid residues have been exchanged with any α-amino acid residue, such as 4 amino acid recidues, 3 amino acid residues, 2 amino acid residues, or 1 amino acid residue.

52b. The formulation according to any one of embodiments 21b-25b, wherein the GLP-2 peptide is selected from the list consisting of
K30R-GLP-2(1-33);
S5K-GLP-2(1-33);

S7K-GLP-2(1-33);
D8K-GLP-2(1-33);
E9K-GLP-2(1-33);
M10K-GLP-2(1-33);
N11K-GLP-2(1-33);
T12K-GLP-2(1-33);
I13K-GLP-2(1-33);
L14K-GLP-2(1-33);
D15K-GLP-2(1-33);
N16K-GLP-2(1-33);
L17K-GLP-2(1-33);
A18K-GLP-2(1-33);
D21K-GLP-2(1-33);
N24K-GLP-2(1-33);
Q28K-GLP-2(1-33);
S5K/K30R-GLP-2(1-33);
S7K/K30R-GLP-2(1-33);
D8K/K30R-GLP-2(1-33);
E9K/K30R-GLP-2(1-33);
M10K/K30R-GLP-2(1-33);
N11K/K30R-GLP-2(1-33);
T12K/K30R-GLP-2(1-33);
I13K/K30R-GLP-2(1-33);
L14K/K30R-GLP-2(1-33);
D15K/K30R-GLP-2(1-33);
N16K/K30R-GLP-2(1-33);
L17K/K30R-GLP-2(1-33);
A18K/K30R-GLP-2(1-33);
D21K/K30R-GLP-2(1-33);
N24K/K30R-GLP-2(1-33);
Q28K/K30R-GLP-2(1-33);
K30R/D33K-GLP-2(1-33);
D3E/K30R/D33E-GLP-2(1-33);
D3E/S5K/K30R/D33E-GLP-2(1-33);
D3E/S7K/K30R/D33E-GLP-2(1-33);
D3E/D8K/K30R/D33E-GLP-2(1-33);
D3E/E9K/K30R/D33E-GLP-2(1-33);
D3E/M10K/K30R/D33E-GLP-2(1-33);
D3E/N11K/K30R/D33E-GLP-2(1-33);
D3E/T12K/K30R/D33E-GLP-2(1-33);
D3E/I13K/K30R/D33E-GLP-2(1-33);
D3E/L14K/K30R/D33E-GLP-2(1-33);
D3E/D15K/K30R/D33E-GLP-2(1-33);
D3E/N16K/K30R/D33E-GLP-2(1-33);
D3E/L17K/K30R/D33E-GLP-2(1-33);
D3E/A18K/K30R/D33E-GLP-2(1-33);
D3E/D21K/K30R/D33E-GLP-2(1-33);
D3E/N24K/K30R/D33E-GLP-2(1-33); and
D3E/Q28K/K30R/D33E-GLP-2(1-33).

53b. The formulation according to any one of embodiments 21b-52b, wherein only one lipophilic substituent is attached to said GLP-2 peptide.

54b. The formulation according to any one of embodiments 21b-53b, wherein said lipophilic substituent comprises from 4 to 40 carbon atoms.

55b. The formulation according to embodiment 54b, wherein said lipophilic substituent comprises from 8 to 25 carbon atoms.

56b. The formulation according to embodiment 55b, wherein said lipophilic substituent comprises from 12 to 20 carbon atoms.

57b. The formulation according to any of embodiments 21b-56b, wherein said lipophilic substituent is attached to an amino acid residue in such a way that a carboxyl group of the lipophilic substituent forms an amide bond with an amino group of the amino acid residue.

58b. The formulation according to embodiment 57b, wherein said amino acid residue is a Lys residue.

59b. The formulation according to any of embodiments 21b-58b, wherein said lipophilic substituent is attached to an amino acid residue in such a way that an amino group of the lipophilic substituent forms an amide bond with a carboxyl group of the amino acid residue.

60b. The formulation according to any of embodiments 21b-59b, wherein said lipophilic substituent is attached to said GLP-2 peptide by means of a spacer.

61b. The formulation according to embodiment 60b, wherein said spacer is an unbranched alkane α,ω-dicarboxylic acid group having from 1 to 7 methylene groups, such as two methylene groups which spacer forms a bridge between an amino group of the GLP-2 peptide and an amino group of said lipophilic substituent.

62b. The formulation according to embodiment 60b, wherein said spacer is an amino acid residue except a Cys residue, or a dipeptide.

63b. The formulation according to embodiment 62b, wherein said spacer is selected from the list consisting of β-alanine, gamma-aminobutyric acid (GABA), γ-glutamic acid, Lys, Asp, Glu, a dipeptide containing Asp, a dipeptide containing Glu, or a dipeptide containing Lys.

64b. The formulation according to embodiments 62b or 63b, wherein a carboxyl group of the parent GLP-2 peptide forms an amide bond with an amino group of said spacer, and the carboxyl group of the amino acid or dipeptide spacer forms an amide bond with an amino group of the lipophilic substituent.

65b. The formulation according to embodiments 62b or 63b, wherein an amino group of the parent GLP-2 peptide forms an amide bond with a carboxylic group of said spacer, and an amino group of said spacer forms an amide bond with a carboxyl group of the lipophilic substituent.

66b. The formulation according to any of embodiments 21b-65b, wherein the lipophilic substituent comprises a partially or completely hydrogenated cyclopentanophenathrene skeleton.

67b. The formulation according to any of embodiments 21b-66b, wherein the lipophilic substituent is an straight-chain or branched alkyl group.

68b. The formulation according to any of embodiments 21b-66b, wherein the lipophilic substituent is the acyl group of a straight-chain or branched fatty acid.

69b. The formulation according to embodiment 68b, wherein the acyl group is selected from the group comprising CH3(CH2)nCO—, wherein n is 4 to 38, such as CH3(CH2)6CO—, CH3(CH2)8CO—, CH3(CH2)10CO—, CH3(CH2)12CO—, CH3(CH2)14CO—, CH3(CH2)16CO—, CH3(CH2)18CO—, CH3(CH2)20CO— and CH3(CH2)22CO—.

70b. The formulation according to any of embodiments 21b-65b, wherein the lipophilic substituent is an acyl group of a straight-chain or branched alkane α,ω-dicarboxylic acid.

71b. The formulation according to embodiment 68b, wherein the acyl group is selected from the group comprising HOOC(CH2)mCO—, wherein m is 4 to 38, such as HOOC(CH2)14CO—, HOOC(CH2)16CO—, HOOC(CH2)18CO—, HOOC(CH2)20CO— and HOOC(CH2)22CO—.

72b. The formulation according to any of embodiments 21b-65b, wherein the lipophilic substituent is a group of the formula CH3(CH2)p((CH2)qCOOH)CHNH—CO(CH2)2CO—, wherein p and q are integers and p+q is an integer of from 8 to 40, such as from 12 to 35.

73b. The formulation according to any of embodiments 21b-65b, wherein the lipophlic substituent is a group of the formula CH3(CH2)rCO—NHCH(COOH)(CH2)2CO—, wherein r is an integer of from 10 to 24.

74b. The formulation according to any of embodiments 21b-65b, wherein the lipophilic substituent is a group of the formula CH3(CH2)sCO—NHCH((CH2)$_2$COOH)CO—, wherein s is an integer of from 8 to 24.

75b. The formulation according to any of embodiments 21b-65b, wherein the lipophilic substituent is a group of the formula COOH(CH2)tCO— wherein t is an integer of from 8 to 24.

76b. The formulation according to any of embodiments 21b-65b, wherein the lipophilic substituent is a group of the formula NHCH(COOH)(CH2)4NH—CO(CH2)uCH3, wherein u is an integer of from 8 to 18.

77b. The formulation according to any of embodiments 21b-65b, wherein the lipophilic substituent is a group of the formula NHCH(COOH)(CH2)4NH—COCH((CH2)2COOH)NH—CO(CH2)wCH3, wherein w is an integer of from 10 to 16.

78b. The formulation according to any of embodiments 21b-65b, wherein the lipophilic substituent is a group of the formula NHCH(COOH)(CH2)4NH—CO(CH2)2CH(COOH)NH—CO(CH2)xCH3, wherein x is an integer of from 10 to 16.

79b. The formulation according to any of embodiments 21b-65b, wherein the lipophilic substituent is a group of the formula NHCH(COOH)(CH2)4NH—CO(CH2)2CH(COOH)NHCO(CH2)yCH3, wherein y is zero or an integer of from 1 to 22.

80b. The formulation according to any of embodiments 21b-79b, which has two lipophilic substituents.

81 b. The formulation according to embodiment 20b, wherein the GLP-2 derivative is selected from the group consisting of S5K(3-(hexadecanoylamino)propionyl)-GLP-2(1-33);
S7K(3-(hexadecanoylamino)propionyl)-GLP-2(1-33);
D8K(3-(hexadecanoylamino)propionyl)-GLP-2(1-33);
E9K(3-(hexadecanoylamino)propionyl)-GLP-2(1-33);
M10K(3-(hexadecanoylamino)propionyl)-GLP-2(1-33);
N11K(3-(hexadecanoylamino)propionyl)-GLP-2(1-33);
T12K(3-(hexadecanoylamino)propionyl)-GLP-2(1-33);
I13K(3-(hexadecanoylamino)propionyl)-GLP-2(1-33);
L14K(3-(hexadecanoylamino)propionyl)-GLP-2(1-33);
D15K(3-(hexadecanoylamino)propionyl)-GLP-2(1-33);
N16K(3-(hexadecanoylamino)propionyl)-GLP-2(1-33);
L17K(3-(octanoylamino)propionyl)-GLP-2(1-33);
L17K(3-(nonanoylamino)propionyl)-GLP-2(1-33);
L17K(3-(decanoylamino)propionyl)-GLP-2(1-33);
L17K(3-(undecanoylamino)propionyl)-GLP-2(1-33);
L17K(3-(dodecanoylamino)propionyl)-GLP-2(1-33);
L17K(3-(tridecanoylamino)propionyl)-GLP-2(1-33);
L17K(3-(tetradecanoylamino)propionyl)-GLP-2(1-33);
L17K(3-(pentadecanoylamino)propionyl)-GLP-2(1-33);
L17K(3-(hexadecanoylamino)propionyl)-GLP-2(1-33);
L17K(3-(heptadecanoylamino)propionyl)-GLP-2(1-33);
L17K(3-(octadecanoylamino)propionyl)-GLP-2(1-33);
L17K(3-(nonadecanoylamino)propionyl)-GLP-2(1-33);
L17K(3-(eicosanoylamino)propionyl)-GLP-2(1-33);
L17K((S)-4-carboxy-4-(octanoylamino)butanoyl)-GLP-2(1-33);
L17K((S)-4-carboxy-4-(nonanoylamino)butanoyl)-GLP-2(1-33);
L17K((S)-4-carboxy-4-(decanoylamino)butanoyl)-GLP-2(1-33);
L17K((S)-4-carboxy-4-(undecanoylamino)butanoyl)-GLP-2(1-33);
L17K((S)-4-carboxy-4-(dodecanoylamino)butanoyl)-GLP-2(1-33);
L17K((S)-4-carboxy-4-(tridecanoylamino)butanoyl)-GLP-2(1-33);
L17K((S)-4-carboxy-4-(tetradecanoylamino)butanoyl)-GLP-2(1-33);
L17K((S)-4-carboxy-4-(pentadecanoylamino)butanoyl)-GLP-2(1-33);
L17K((S)-4-carboxy-4-(hexadecanoylamino)butanoyl)-GLP-2(1-33);
L17K((S)-4-carboxy-4-(heptadecanoylamino)butanoyl)-GLP-2(1-33);
L17K((S)-4-carboxy-4-(octadecanoylamino)butanoyl)-GLP-2(1-33);
L17K((S)-4-carboxy-4-(nonadecanoylamino)butanoyl)-GLP-2(1-33);
L17K((S)-4-carboxy-4-(eicosanoylamino)butanoyl)-GLP-2(1-33);
L17K(4-(octanoylamino)butanoyl)-GLP-2(1-33);
L17K(4-(nonanoylamino)butanoyl)-GLP-2(1-33);
L17K(4-(decanoylamino)butanoyl)-GLP-2(1-33);
L17K(4-(undecanoylamino)butanoyl)-GLP-2(1-33);
L17K(4-(dodecanoylamino)butanoyl)-GLP-2(1-33);
L17K(4-(tridecanoylamino)butanoyl)-GLP-2(1-33);
L17K(4-(tetradecanoylamino)butanoyl)-GLP-2(1-33);
L17K(4-(pentadecanoylamino)butanoyl)-GLP-2(1-33);
L17K(4-(hexadecanoylamino)butanoyl)-GLP-2(1-33);
L17K(4-(heptadecanoylamino)butanoyl)-GLP-2(1-33);
L17K(4-(octadecanoylamino)butanoyl)-GLP-2(1-33);
L17K(4-(nonadecanoylamino)butanoyl)-GLP-2(1-33);
L17K(4-(eicosanoylamino)butanoyl)-GLP-2(1-33);
A18K(3-(hexadecanoylamino)propionyl)-GLP-2(1-33);
D21K(3-(hexadecanoylamino)propionyl)-GLP-2(1-33);
N24K(3-(hexadecanoylamino)propionyl)-GLP-2(1-33);
Q28K(3-(hexadecanoylamino)propionyl)-GLP-2(1-33);
S5K(3-(hexadecanoylamino)propionyl)/K30R-GLP-2(1-33);
S7K(3-(hexadecanoylamino)propionyl)/K30R-GLP-2(1-33);
D8K(3-(hexadecanoylamino)propionyl)/K30R-GLP-2(1-33);
E9K(3-(hexadecanoylamino)propionyl)/K30R-GLP-2(11-33);
M10K(3-(hexadecanoylamino)propionyl)/K30R-GLP-2(1-33);
N11K(3-(hexadecanoylamino)propionyl)/K30R-GLP-2(1-33);
T12K(3-(hexadecanoylamino)propionyl)/K30R-GLP-2(1-33);
I13K(3-(hexadecanoylamino)propionyl)/K30R-GLP-2(1-33);
L14K(3-(hexadecanoylamino)propionyl)/K30R-GLP-2(1-33);
D15K(3-(hexadecanoylamino)propionyl)/K30R-GLP-2(1-33);
N16K(3-(hexadecanoylamino)propionyl)/K30R-GLP-2(1-33);
L17K(3-(octanoylamino)propionyl)/K30R-GLP-2(1-33);
L17K(3-(nonanoylamino)propionyl)/K30R-GLP-2(1-33);
L17K(3-(decanoylamino)propionyl)/K30R-GLP-2(1-33);
L17K(3-(undecanoylamino)propionyl)/K30R-GLP-2(1-33);
L17K(3-(dodecanoylamino)propionyl)/K30R-GLP-2(1-33);
L17K(3-(tridecanoylamino)propionyl)/K30R-GLP-2(1-33);
L17K(3-(tetradecanoylamino)propionyl)/K30R-GLP-2(1-33);

L17K(3-(pentadecanoylamino)propionyl)/K30R-GLP-2(1-33);
L17K(3-(hexadecanoylamino)propionyl)/K30R-GLP-2(1-33);
L17K(3-(heptadecanoylamino)propionyl)/K30R-GLP-2(1-33);
L17K(3-(octadecanoylamino)propionyl)/K30R-GLP-2(1-33);
L17K(3-(nonadecanoylamino)propionyl)/K30R-GLP-2(1-33);
L17K(3-(eicosanoylamino)propionyl)/K30R-GLP-2(1-33);
L17K((S)-4-carboxy-4-(octanoylamino)butanoyl)/K30R-GLP-2(1-33);
L17K((S)-4-carboxy-4-(nonanoylamino)butanoyl)/K30R-GLP-2(1-33);
L17K((S)-4-carboxy-4-(decanoylamino)butanoyl)/K30R-GLP-2(1-33);
L17K((S)-4-carboxy-4-(undecanoylamino)butanoyl)/K30R-GLP-2(1-33);
L17K((S)-4-carboxy-4-(dodecanoylamino)butanoyl)/K30R-GLP-2(1-33);
L17K((S)-4-carboxy-4-(tridecanoylamino)butanoyl)/K30R-GLP-2(1-33);
L17K((S)-4-carboxy-4-(tetradecanoylamino)butanoyl)/K30R-GLP-2(1-33);
L17K((S)-4-carboxy-4-(pentadecanoylamino)butanoyl)/K30R-GLP-2(1-33);
L17K((S)-4-carboxy-4-(hexadecanoylamino)butanoyl)/K30R-GLP-2(1-33);
L17K((S)-4-carboxy-4-(heptadecanoylamino)butanoyl)/K30R-GLP-2(1-33);
L17K((S)-4-carboxy-4-(octadecanoylamino)butanoyl)/K30R-GLP-2(1-33);
L17K((S)-4-carboxy-4-(nonadecanoylamino)butanoyl)/K30R-GLP-2(1-33);
L17K((S)-4-carboxy-4-(eicosanoylamino)butanoyl)/K30R-GLP-2(1-33);
L17K(4-(octanoylamino)butanoyl)/K30R-GLP-2(1-33);
L17K(4-(nonanoylamino)butanoyl)/K30R-GLP-2(1-33);
L17K(4-(decanoylamino)butanoyl)/K30R-GLP-2(1-33);
L17K(4-(undecanoylamino)butanoyl)/K30R-GLP-2(1-33);
L17K(4-(dodecanoylamino)butanoyl)/K30R-GLP-2(1-33);
L17K(4-(tridecanoylamino)butanoyl)/K30R-GLP-2(1-33);
L17K(4-(tetradecanoylamino)butanoyl)/K30R-GLP-2(1-33);
L17K(4-(pentadecanoylamino)butanoyl)/K30R-GLP-2(1-33);
L17K(4-(hexadecanoylamino)butanoyl)/K30R-GLP-2(1-33);
L17K(4-(heptadecanoylamino)butanoyl)/K30R-GLP-2(1-33);
L17K(4-(octadecanoylamino)butanoyl)/K30R-GLP-2(1-33);
L17K(4-(nonadecanoylamino)butanoyl)/K30R-GLP-2(1-33);
L17K(4-(eicosanoylamino)butanoyl)/K30R-GLP-2(1-33);
A18K(3-(hexadecanoylamino)propionyl)/K30R-GLP-2(1-33);
D21K(3-(hexadecanoylamino)propionyl)/K30R-GLP-2(1-33);
N24K(3-(hexadecanoylamino)propionyl)/K30R-GLP-2(1-33);
Q28K(3-(hexadecanoylamino)propionyl)/K30R-GLP-2(1-33);
D3E/S5K(3-(hexadecanoylamino)propionyl)/K30R/D33E-GLP-2(1-33);
D3E/S7K(3-(hexadecanoylamino)propionyl)/K30R/D33E-GLP-2(1-33);
D3E/D8K(3-(hexadecanoylamino)propionyl)/K30R/D33E-GLP-2(1-33);
D3E/E9K(3-(hexadecanoylamino)propionyl)/K30R/D33E-GLP-2(1-33);
D3E/M10K(3-(hexadecanoylamino)propionyl)/K30R/D33E-GLP-2(1-33);
D3E/N11K(3-(hexadecanoylamino)propionyl)/K30R/D33E-GLP-2(1-33);
D3E/T12K(3-(hexadecanoylamino)propionyl)/K30R/D33E-GLP-2(1-33);
D3E/I13K(3-(hexadecanoylamino)propionyl)/K30R/D33E-GLP-2(1-33);
D3E/L14K(3-(hexadecanoylamino)propionyl)/K30R/D33E-GLP-2(1-33);
D3E/D15K(3-(hexadecanoylamino)propionyl)/K30R/D33E-GLP-2(1-33);
D3E/N16K(3-(hexadecanoylamino)propionyl)/K30R/D33E-GLP-2(1-33);
D3E/L17K(3-(octanoylamino)propionyl)/K30R/D33E-GLP-2(1-33);
D3E/L17K(3-(nonanoylamino)propionyl)/K30R/D33E-GLP-2(1-33);
D3E/L17K(3-(decanoylamino)propionyl)/K30R/D33E-GLP-2(1-33);
D3E/L17K(3-(undecanoylamino)propionyl)/K30R/D33E-GLP-2(1-33);
D3E/L17K(3-(dodecanoylamino)propionyl)/K30R/D33E-GLP-2(1-33);
D3E/L17K(3-(tridecanoylamino)propionyl)/K30R/D33E-GLP-2(1-33);
D3E/L17K(3-(tetradecanoylamino)propionyl)/K30R/D33E-GLP-2(1-33);
D3E/L17K(3-(pentadecanoylamino)propionyl)/K30R/D33E-GLP-2(1-33);
D3E/L17K(3-(hexadecanoylamino)propionyl)/K30R/D33E-GLP-2(1-33);
D3E/L17K(3-(heptadecanoylamino)propionyl)/K30R/D33E-GLP-2(1-33);
D3E/L17K(3-(octadecanoylamino)propionyl)/K30R/D33E-GLP-2(1-33);
D3E/L17K(3-(nonadecanoylamino)propionyl)/K30R/D33E-GLP-2(1-33);
D3E/L17K(3-(eicosanoylamino)propionyl)/K30R/D33E-GLP-2(1-33);
D3E/L17K((S)-4-carboxy-4-(octanoylamino)butanoyl)/K30R/D33E-GLP-2(1-33);
D3E/L17K((S)-4-carboxy-4-(nonanoylamino)butanoyl)/K30R/D33E-GLP-2(1-33);
D3E/L17K((S)-4-carboxy-4-(decanoylamino)butanoyl)/K30R/D33E-GLP-2(1-33);
D3E/L17K((S)-4-carboxy-4-(undecanoylamino)butanoyl)/K30R/D33E-GLP-2(1-33);
D3E/L17K((S)-4-carboxy-4-(dodecanoylamino)butanoyl)/K30R/D33E-GLP-2(1-33);
D3E/L17K((S)-4-carboxy-4-(tridecanoylamino)butanoyl)/K30R/D33E-GLP-2(1-33);
D3E/L17K((S)-4-carboxy-4-(tetradecanoylamino)butanoyl)/K30R/D33E-GLP-2(1-33);
D3E/L17K((S)-4-carboxy-4-(pentadecanoylamino)butanoyl)/K30R/D33E-GLP-2(1-33);
D3E/L17K((S)-4-carboxy-4-(hexadecanoylamino)butanoyl)/K30R/D33E-GLP-2(1-33);
D3E/L17K((S)-4-carboxy-4-(heptadecanoylamino)butanoyl)/K30R/D33E-GLP-2(1-33);

D3E/L17K((S)-4-carboxy-4-(octadecanoylamino)butanoyl)/K30R/D33E-GLP-2(11-33);
D3E/L17K((S)-4-carboxy-4-(nonadecanoylamino)butanoyl)/K30R/D33E-GLP-2(1-33);
D3E/L17K((S)-4-carboxy-4-(eicosanoylamino)butanoyl)/K30R/D33E-GLP-2(1-33);
D3E/L17K(4-(octanoylamino)butanoyl)/K30R/D33E-GLP-2(1-33);
D3E/L17K(4-(nonanoylamino)butanoyl)/K30R/D33E-GLP-2(1-33);
D3E/L17K(4-(decanoylamino)butanoyl)/K30R/D33E-GLP-2(1-33);
D3E/L17K(4-(undecanoylamino)butanoyl)/K30R/D33E-GLP-2(1-33);
D3E/L17K(4-(dodecanoylamino)butanoyl)/K30R/D33E-GLP-2(1-33);
D3E/L17K(4-(tridecanoylamino)butanoyl)/K30R/D33E-GLP-2(1-33);
D3E/L17K(4-(tetradecanoylamino)butanoyl)/K30R/D33E-GLP-2(1-33);
D3E/L17K(4-(pentadecanoylamino)butanoyl)/K30R/D33E-GLP-2(1-33);
D3E/L17K(4-(hexadecanoylamino)butanoyl)/K30R/D33E-GLP-2(1-33);
D3E/L17K(4-(heptadecanoylamino)butanoyl)/K30R/D33E-GLP-2(1-33);
D3E/L17K(4-(octadecanoylamino)butanoyl)/K30R/D33E-GLP-2(1-33);
D3E/L17K(4-(nonadecanoylamino)butanoyl)/K30R/D33E-GLP-2(1-33);
D3E/L17K(4-(eicosanoylamino)butanoyl)/K30R/D33E-GLP-2(1-33);
D3E/A18K(3-(hexadecanoylamino)propionyl)/K30R/D33E-GLP-2(1-33);
D3E/D21 K(3-(hexadecanoylamino)propionyl)/K30R/D33E-GLP-2(1-33);
D3E/N24K(3-(hexadecanoylamino)propionyl)/K30R/D33E-GLP-2(1-33); and
D3E/Q28K(3-(hexadecanoylamino)propionyl)/K30R/D33E-GLP-2(1-33).

82b. A method of preparing a physically stable pharmaceutical formulation of a GLP-2 compound comprising preparing a formulation containing the GLP-2 compound, and a buffer, wherein said GLP-2 compound is present in a concentration from 0.1 mg/ml to 100 mg/ml, and wherein said formulation has a pH from 8.0 to 10.

83b. The method according to embodiment 82b, wherein said pharmaceutical formulation is as defined in any of embodiments 1b-81b.

84b. A composition comprising a GLP-2 compound, and a buffer, wherein said GLP-2 compound is present in a concentration from 0.1 mg/ml to 100 mg/ml, and wherein said composition has a pH from 8.0 to 10, or a freeze-dried formulation thereof.

85b. The composition according to embodiment 84b, further comprising water.

86b. A composition comprising an aqueous solution of a GLP-2 compound, and a buffer, wherein said GLP-2 compound is present in a concentration from 0.1 mg/ml to 100 mg/ml, and wherein said composition has a pH from 8.0 to 10.

Further Embodiments:

1c. A pharmaceutical formulation comprising a GLP-2 derivative, and a buffer, or a freeze-dried formulation thereof, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said formulation has a pH from 7.0 to 10.

2c. The formulation according to embodiment 1c, further comprising water.

3c. A pharmaceutical formulation comprising an aqueous solution of a GLP-2 derivative, and a buffer, wherein said GLP-2 derivative is present in a concentration from 0.1 mg/ml to 100 mg/ml, and wherein said formulation has a pH from 7.0 to 10.

4c. The formulation according to any one of embodiments 1c-3c, wherein said GLP-2 derivative is present in a concentration from 1 mg/ml to 100 mg/ml.

5c. The formulation according to any one of embodiments 1c-4c, wherein said formulation has a pH from 7.0 to 9.0.

6c. The formulation according to any one of embodiments 1c-5c, wherein said formulation has a pH from 7.0 to 8.0.

7c. The formulation according to any one of embodiments 1c-6c, wherein the GLP-2 derivative is present in a concentration from 0.1 mg/ml to 80 mg/ml, 0.1 mg/ml to 50 mg/ml, 0.1 mg/ml to 20 mg/ml, 0.1 mg/ml to 10 mg/ml, typically from 0.1-5 mg/ml.

8c. The formulation according to any one of embodiments 1c-7c, wherein the GLP-2 derivative is present in a concentration from 1 mg/ml to 80 mg/ml, 1 mg/ml to 50 mg/ml, 1 mg/ml to 20 mg/ml, 1 mg/ml to 10 mg/ml, typically from 1-5 mg/ml.

9c. The formulation according to any one of embodiments 1c-8c, further comprising a preservative.

10c. The formulation according to embodiment 9c, wherein said preservative is present in a concentration from 0.1 mg/ml to 20 mg/ml.

11c. The formulation according to any one of embodiments 1c-10c, further comprising an isotonic agent.

12c. The formulation according to embodiment 11c, wherein said isotonic agent is present in a concentration from 1 mg/ml to 50 mg/ml.

13c. The formulation according to any one of embodiments 1c-12c, further comprising a chelating agent.

14c. The formulation according to embodiment 13c, wherein said chelating agent is present in a concentration from 0.1 mg/ml to 5 mg/ml.

15c. The formulation according to any one of embodiments 1c-14c, further comprising a stabiliser.

16c. The formulation according to embodiment 15c, wherein said stabiliser is selected from the group consisting of L-histidine, imidazole and arginine.

17c. The formulation according to embodiment 16c, wherein said stabiliser is a high molecular weight polymer and/or a low molecular weight compound and is present in a concentration from 0.1 mg/ml to 50 mg/ml.

18c. The formulation according to any one of embodiments 1c-17c, further comprising a surfactant.

19c. The formulation according to any one of embodiments 1c-18c, wherein the GLP-2 peptide is according to formula II His-X2-X3-Gly-X5-Phe-X7-X8-X9-X10-X11-X12-X13-X14-X15-X16-X17-X18-Ala-X20-X21-Phe-Ile-X24-Trp-Leu-Ile-X28-Thr-X30-Ile-Thr-X33 (formula II)

or a fragment thereof; wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X20 is Arg, or Lys; X21 is Asp, or Lys; X24 is Asn, or Lys; X28 is Gln, or Lys; X30 is Arg, or Lys; X33 is Asp, Glu, or Lys (formula II).

20c. The formulation according to any one of embodiments 1c-19c, wherein the GLP-2 peptide comprises the amino acid sequence of formula I His-X2-X3-Gly-X5-Phe-X7-X8-X9-X10-X11-X12-X13-X14-X15-X16-X17-X18-Ala-Arg-X21-Phe-Ile-X24-Trp-Leu-Ile-X28-Thr-Arg-Ile-Thr-X33  (formula I)

or a fragment thereof; wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X21 is Asp, or Lys; X24 is Asn, or Lys; X28 is Gln, or Lys; X33 is Asp, Glu, or Lys.

21c. The formulation according to any one of embodiments 1c-20c, wherein the GLP-2 peptide consists of the amino acid sequence His-X2-X3-Gly-X5-Phe-X7-X8-X9-X10-X11-X12-X13-X14-X15-X16-X17-X18-Ala-X20-X21-Phe-Ile-X24-Trp-Leu-Ile-X28-Thr-Arg-Ile-Thr-X33 or a fragment thereof; wherein X2 is Ala, Val or Gly; X3 is Asp, or Glu; X5 is Ser, or Lys; X7 is Ser, or Lys; X8 is Asp, Glu, or Lys; X9 is Asp, Glu, or Lys; X10 is Met, Lys, Leu, Ile, or Nor-Leucine; X11 is Asn, or Lys; X12 is Thr, or Lys; X13 is Ile, or Lys; X14 is Leu, or Lys; X15 is Asp, or Lys; X16 is Asn, or Lys; X17 is Leu, or Lys; X18 is Ala, or Lys; X20 is Arg, or Lys; X21 is Asp, or Lys; X24 is Asn, or Lys; X28 is Gln, or Lys; X33 is Asp, Glu, or Lys.

22c. The formulation according to any one of embodiments 19c-21c, wherein X2 is Ala.

23c. The formulation according to any one of embodiments 19c-21c, wherein X2 is Gly.

24c. The formulation according to any one of embodiments 19c-23c, wherein X3 is Asp.

25c. The formulation according to any one of embodiments 19c-23c, wherein X3 is Glu.

26c. The formulation according to any one of embodiments 19c-25c, wherein X5 is Ser.

27c. The formulation according to any one of embodiments 19c-26c, wherein X7 is Ser.

28c. The formulation according to any one of embodiments 19c-27c, wherein X8 is Asp.

29c. The formulation according to any one of embodiments 19c-27c, wherein X8 is Glu.

30c. The formulation according to any one of embodiments 19c-29c, wherein X9 is Asp.

31c. The formulation according to any one of embodiments 19c-29c, wherein X9 is Glu.

32c. The formulation according to any one of embodiments 19c-31c, wherein X10 is selected from the group consisting of Met, Leu, Ile, and Nor-Leucine.

33c. The formulation according to any one of embodiments 19c-32c, wherein X11 is Asn.

34c. The formulation according to any one of embodiments 19c-33c, wherein X12 is Thr.

35c. The formulation according to any one of embodiments 19c-34c, wherein X13 is Ile.

36c. The formulation according to any one of embodiments 19c-35c, wherein X14 is Leu.

37c. The formulation according to any one of embodiments 19c-36c, wherein X15 is Asp.

38c. The formulation according to any one of embodiments 19c-37c, wherein X16 is Asn.

39c. The formulation according to any one of embodiments 19c-38c, wherein X17 is Leu.

40c. The formulation according to any one of embodiments 19-39, wherein X18 is Ala.

41c. The formulation according to any one of embodiments 19c-40c, wherein X21 is Asp.

42c. The formulation according to any one of embodiments 19c-41c, wherein X24 is Asn.

43c. The formulation according to any one of embodiments 19c-42c, wherein X28 is Gln.

44c. The formulation according to any one of embodiments 19c-43c, wherein X33 is Asp.

45c. The formulation according to any one of embodiments 19c-44c, wherein X33 is Glu.

46c. The formulation according to any one of embodiments 19c-45c, wherein at least one amino acid independently selected from the list consisting of X5, X7, X8, X9, X10, X11, X12, X13, X14, X15, X16, X17, X18, X20, X21, X24, X28, and X33 is a Lys.

47c. The formulation according to any one of embodiments 1c-46c, wherein a total of up to 5 amino acid residues have been exchanged with any α-amino acid residue, such as 4 amino acid recidues, 3 amino acid residues, 2 amino acid residues, or 1 amino acid residue.

48c. The formulation according to any one of embodiments 1c-47c, wherein the GLP-2 peptide is selected from the list consisting of
K30R-GLP-2(1-33);
S5K-GLP-2(1-33);
S7K-GLP-2(1-33);
D8K-GLP-2(1-33);
E9K-GLP-2(1-33);
M10K-GLP-2(1-33);
N12K-GLP-2(1-33);
T12K-GLP-2(1-33);
I3K-GLP-2(1-33);
L14K-GLP-2(1-33);
D15K-GLP-2(1-33);
N16K-GLP-2(1-33);
L17K-GLP-2(1-33);
A18K-GLP-2(1-33);
D21K-GLP-2(1-33);
N24K-GLP-2(1-33);
Q28K-GLP-2(1-33);
S5K/K30R-GLP-2(1-33);
S7K/K30R-GLP-2(1-33);
D8K/K30R-GLP-2(1-33);
E9K/K30R-GLP-2(1-33);
M10K/K30R-GLP-2(1-33);
M11K/K30R-GLP-2(1-33);
T12K/K30R-GLP-2(1-33);
I13K/K30R-GLP-2(1-33);
L14K/K30R-GLP-2(1-33);
D15K/K30R-GLP-2(1-33);
N16K/K30R-GLP-2(1-33);
L17K/K30R-GLP-2(1-33);
A18K/K30R-GLP-2(1-33);
D21K/K30R-GLP-2(1-33);
N24K/K30R-GLP-2(1-33);
Q28k/K30R-GLP-2(1-33);
K30R/D33K-GLP-2(1-33);

D3E/K30R/D33E-GLP-2(1-33);
D3E/S5K/K30R/D33E-GLP-2(1-33);
D3E/S7K/K30R/D33E-GLP-2(1-33);
D3E/D8K/K30R/D33E-GLP-2(1-33);
D3E/E9K/K30R/D33E-GLP-2(1-33);
D3E/M10K/K30R/D33E-GLP-2(1-33);
D3E/N11K/K30R/D33E-GLP-2(1-33);
D3E/T12K/K30R/D33E-GLP-2(1-33);
D3E/I13K/K30R/D33E-GLP-2(1-33);
D3E/L14K/K30R/D33E-GLP-2(1-33);
D3E/D15K/K30R/D33E-GLP-2(1-33);
D3E/N16K/K30R/D33E-GLP-2(1-33);
D3E/L17K/K30R/D33E-GLP-2(1-33);
D3E/A18K/K30R/D33E-GLP-2(1-33);
D3E/D21K/K30R/D33E-GLP-2(1-33);
D3E/N24K/K30R/D33E-GLP-2(1-33); and
D3E/Q28K/K30R/D33E-GLP-2(1-33).

49c. The formulation according to any one of embodiments 1c-48c, wherein only one lipophilic substituent is attached to said GLP-2 peptide.

50c. The formulation according to any one of embodiments 1c-49c, wherein said lipophilic substituent comprises from 4 to 40 carbon atoms.

51c. The formulation according to embodiment 50c, wherein said lipophilic substituent comprises from 8 to 25 carbon atoms.

52c. The formulation according to embodiment 51c, wherein said lipophilic substituent comprises from 12 to 20 carbon atoms.

53c. The formulation according to any of embodiments 1c-52c, wherein said lipophilic substituent is attached to an amino acid residue in such a way that a carboxyl group of the lipophilic substituent forms an amide bond with an amino group of the amino acid residue.

54c. The formulation according to embodiment 53c, wherein said amino acid residue is a Lys residue.

55c. The formulation according to any of embodiments 1c-54c, wherein said lipophilic substituent is attached to an amino acid residue in such a way that an amino group of the lipophilic substituent forms an amide bond with a carboxyl group of the amino acid residue.

56c. The formulation according to any of embodiments 1c-55c, wherein said lipophilic substituent is attached to said GLP-2 peptide by means of a spacer.

57c. The formulation according to embodiment 56c, wherein said spacer is an unbranched alkane $\alpha,\omega$-dicarboxylic acid group having from 1 to 7 methylene groups, such as two methylene groups which spacer forms a bridge between an amino group of the GLP-2 peptide and an amino group of said lipophilic substituent.

58c. The formulation according to embodiment 56c, wherein said spacer is an amino acid residue except a Cys residue, or a dipeptide.

59c. The formulation according to embodiment 58c, wherein said spacer is selected from the list consisting of β-alanine, gamma-aminobutyric acid (GABA), γ-glutamic acid, Lys, Asp, Glu, a dipeptide containing Asp, a dipeptide containing Glu, or a dipeptide containing Lys.

60c. The formulation according to embodiments 58c or 59c, wherein a carboxyl group of the parent GLP-2 peptide forms an amide bond with an amino group of said spacer, and the carboxyl group of the amino acid or dipeptide spacer forms an amide bond with an amino group of the lipophilic substituent.

61c. The formulation according to embodiments 58c or 59c, wherein an amino group of the parent GLP-2 peptide forms an amide bond with a carboxylic group of said spacer, and an amino group of said spacer forms an amide bond with a carboxyl group of the lipophilic substituent.

62c. The formulation according to any of embodiments 1c-61c, wherein the lipophilic substituent comprises a partially or completely hydrogenated cyclopentanophenathrene skeleton.

63c. The formulation according to any of embodiments 1c-62c, wherein the lipophilic substituent is an straight-chain or branched alkyl group.

64c. The formulation according to any of embodiments 1c-62c, wherein the lipophilic substituent is the acyl group of a straight-chain or branched fatty acid.

65c. The formulation according to embodiment 64c, wherein the acyl group is selected from the group comprising CH3(CH2)nCO—, wherein n is 4 to 38, such as CH3(CH2)6CO—, CH3(CH2)8CO—, CH3(CH2)10CO—, CH3(CH2)12CO—, CH3(CH2)14CO—, CH3(CH2)16CO—, CH3(CH2)18CO—, CH3(CH2)20CO— and CH3(CH2)22CO—.

66c. The formulation according to any of embodiments 1c-61c, wherein the lipophilic substituent is an acyl group of a straight-chain or branched alkane $\alpha,\omega$-dicarboxylic acid.

67c. The formulation according to embodiment 66c, wherein the acyl group is selected from the group comprising HOOC(CH2)mCO—, wherein m is 4 to 38, such as HOOC(CH2)14CO—, HOOC(CH2)16CO—, HOOC(CH2)18CO—, HOOC(CH2)20CO— and HOOC(CH2)22CO—.

68c. The formulation according to any of embodiments 1c-61c, wherein the lipophilic substituent is a group of the formula CH3(CH2)p((CH2)qCOOH)CHNH—CO(CH2)2CO—, wherein p and q are integers and p+q is an integer of from 8 to 40, such as from 12 to 35.

69c. The formulation according to any of embodiments 1c-61c, wherein the lipophlic substituent is a group of the formula CH3(CH2)rCO—NHCH(COOH)(CH2)2CO—, wherein r is an integer of from 10 to 24.

70c. The formulation according to any of embodiments 1c-61c, wherein the lipophilic substituent is a group of the formula CH3(CH2)sCO—NHCH((CH2)2COOH)CO—, wherein s is an integer of from 8 to 24.

71c. The formulation according to any of embodiments 1c-61c, wherein the lipophilic substituent is a group of the formula COOH(CH2)tCO— wherein t is an integer of from 8 to 24.

72c. The formulation according to any of embodiments 1c-61c, wherein the lipophilic substituent is a group of the formula NHCH(COOH)(CH2)4NH—CO(CH2)uCH3, wherein u is an integer of from 8 to 18.

73c. The formulation according to any of embodiments 1c-61c, wherein the lipophilic substituent is a group of the formula NHCH(COOH)(CH2)4NH—COCH((CH2)2COOH)NH—CO(CH2)wCH3, wherein w is an integer of from 10 to 16.

74c. The formulation according to any of embodiments 1c-61c, wherein the lipophilic substituent is a group of the formula NHCH(COOH)(CH2)4NH—CO(CH2)2CH(COOH)NH—CO(CH2)xCH3, wherein x is an integer of from 10 to 16.

75c. The formulation according to any of embodiments 1c-61c, wherein the lipophilic substituent is a group of the formula NHCH(COOH)(CH2)4NH—CO(CH2)2CH(COOH)NHCO(CH2)yCH3, wherein y is zero or an integer of from 1 to 22.

76c. The formulation according to any of embodiments 1c-75c, which has two lipophilic substituents.

77c. The formulation according to any of embodiments 1c-18c, wherein the GLP-2 derivative is selected from the group consisting of
S5K(3-(hexadecanoylamino)propionyl)-GLP-2(1-33);
S7K(3-(hexadecanoylamino)propionyl)-GLP-2(1-33);
D8K(3-(hexadecanoylamino)propionyl)-GLP-2(1-33);
E9K(3-(hexadecanoylamino)propionyl)-GLP-2(1-33);
M10K(3-(hexadecanoylamino)propionyl)-GLP-2(1-33);
N11K(3-(hexadecanoylamino)propionyl)-GLP-2(1-33);
T12K(3-(hexadecanoylamino)propionyl)-GLP-2(1-33);
I13K(3-(hexadecanoylamino)propionyl)-GLP-2(1-33);
L14K(3-(hexadecanoylamino)propionyl)-GLP-2(1-33);
D15K(3-(hexadecanoylamino)propionyl)-GLP-2(1-33);
N16K(3-(hexadecanoylamino)propionyl)-GLP-2(1-33);
L17K(3-(octanoylamino)propionyl)-GLP-2(1-33);
L17K(3-(nonanoylamino)propionyl)-GLP-2(1-33);
L17K(3-(decanoylamino)propionyl)-GLP-2(1-33);
L17K(3-(undecanoylamino)propionyl)-GLP-2(1-33);
L17K(3-(dodecanoylamino)propionyl)-GLP-2(1-33);
L17K(3-(tridecanoylamino)propionyl)-GLP-2(1-33);
L17K(3-(tetradecanoylamino)propionyl)-GLP-2(1-33);
L17K(3-(pentadecanoylamino)propionyl)-GLP-2(1-33);
L17K(3-(hexadecanoylamino)propionyl)-GLP-2(1-33);
L17K(3-(heptadecanoylamino)propionyl)-GLP-2(1-33);
L17K(3-(octadecanoylamino)propionyl)-GLP-2(1-33);
L17K(3-(nonadecanoylamino)propionyl)-GLP-2(1-33);
L17K(3-(eicosanoylamino)propionyl)-GLP-2(1-33);
L17K((S)-4-carboxy-4-(octanoylamino)butanoyl)-GLP-2(1-33);
L17K((S)-4-carboxy-4-(nonanoylamino)butanoyl)-GLP-2(1-33);
L17K((S)-4-carboxy-4-(decanoylamino)butanoyl)-GLP-2(1-33);
L17K((S)-4-carboxy-4-(undecanoylamino)butanoyl)-GLP-2(1-33);
L17K((S)-4-carboxy-4-(dodecanoylamino)butanoyl)-GLP-2(1-33);
L17K((S)-4-carboxy-4-(tridecanoylamino)butanoyl)-GLP-2(1-33);
L17K((S)-4-carboxy-4-(tetradecanoylamino)butanoyl)-GLP-2(1-33);
L17K((S)-4-carboxy-4-(pentadecanoylamino)butanoyl)-GLP-2(1-33);
L17K((S)-4-carboxy-4-(hexadecanoylamino)butanoyl)-GLP-2(1-33);
L17K((S)-4-carboxy-4-(heptadecanoylamino)butanoyl)-GLP-2(1-33);
L17K((S)-4-carboxy-4-(octadecanoylamino)butanoyl)-GLP-2(1-33);
L17K((S)-4-carboxy-4-(nonadecanoylamino)butanoyl)-GLP-2(1-33);
L17K((S)-4-carboxy-4-(eicosanoylamino)butanoyl)-GLP-2(1-33);
L17K(4-(octanoylamino)butanoyl)-GLP-2(1-33);
L17K(4-(nonanoylamino)butanoyl)-GLP-2(1-33);
L17K(4-(decanoylamino)butanoyl)-GLP-2(1-33);
L17K(4-(undecanoylamino)butanoyl)-GLP-2(1-33);
L17K(4-(dodecanoylamino)butanoyl)-GLP-2(1-33);
L17K(4-(tridecanoylamino)butanoyl)-GLP-2(1-33);
L17K(4-(tetradecanoylamino)butanoyl)-GLP-2(1-33);
L17K(4-(pentadecanoylamino)butanoyl)-GLP-2(1-33);
L17K(4-(hexadecanoylamino)butanoyl)-GLP-2(1-33);
L17K(4-(heptadecanoylamino)butanoyl)-GLP-2(1-33);
L17K(4-(octadecanoylamino)butanoyl)-GLP-2(1-33);
L17K(4-(nonadecanoylamino)butanoyl)-GLP-2(1-33);
L17K(4-(eicosanoylamino)butanoyl)-GLP-2(1-33);
A18K(3-(hexadecanoylamino)propionyl)-GLP-2(1-33);
D21K(3-(hexadecanoylamino)propionyl)-GLP-2(1-33);
N24K(3-(hexadecanoylamino)propionyl)-GLP-2(1-33);
Q28K(3-(hexadecanoylamino)propionyl)-GLP-2(1-33);
S5K(3-(hexadecanoylamino)propionyl)/K30R-GLP-2(1-33);
S7K(3-(hexadecanoylamino)propionyl)/K30R-GLP-2(1-33);
D8K(3-(hexadecanoylamino)propionyl)/K30R-GLP-2(11-33);
E9K(3-(hexadecanoylamino)propionyl)/K30R-GLP-2(1-33);
M10K(3-(hexadecanoylamino)propionyl)/K30R-GLP-2(1-33);
N11K(3-(hexadecanoylamino)propionyl)/K30R-GLP-2(1-33);
T12K(3-(hexadecanoylamino)propionyl)/K30R-GLP-2(1-33);
I13K(3-(hexadecanoylamino)propionyl)/K30R-GLP-2(1-33);
L14K(3-(hexadecanoylamino)propionyl)/K30R-GLP-2(1-33);
D15K(3-(hexadecanoylamino)propionyl)/K30R-GLP-2(1-33);
N16K(3-(hexadecanoylamino)propionyl)/K30R-GLP-2(1-33);
L17K(3-(octanoylamino)propionyl)/K30R-GLP-2(1-33);
L17K(3-(nonanoylamino)propionyl)/K30R-GLP-2(1-33);
L17K(3-(decanoylamino)propionyl)/K30R-GLP-2(1-33);
L17K(3-(undecanoylamino)propionyl)/K30R-GLP-2(1-33);
L17K(3-(dodecanoylamino)propionyl)/K30R-GLP-2(1-33);
L17K(3-(tridecanoylamino)propionyl)/K30R-GLP-2(1-33);
L17K(3-(tetradecanoylamino)propionyl)/K30R-GLP-2(1-33);
L17K(3-(pentadecanoylamino)propionyl)/K30R-GLP-2(1-33);
L17K(3-(hexadecanoylamino)propionyl)/K30R-GLP-2(1-33);
L17K(3-(heptadecanoylamino)propionyl)/K30R-GLP-2(1-33);
L17K(3-(octadecanoylamino)propionyl)/K30R-GLP-2(1-33);
L17K(3-(nonadecanoylamino)propionyl)/K30R-GLP-2(1-33);
L17K(3-(eicosanoylamino)propionyl)/K30R-GLP-2(1-33);
L17K((S)-4-carboxy-4-(octanoylamino)butanoyl)/K30R-GLP-2(1-33);
L17K((S)-4-carboxy-4-(nonanoylamino)butanoyl)/K30R-GLP-2(1-33);
L17K((S)-4-carboxy-4-(decanoylamino)butanoyl)/K30R-GLP-2(1-33);
L17K((S)-4-carboxy-4-(undecanoylamino)butanoyl)/K30R-GLP-2(1-33);
L17K((S)-4-carboxy-4-(dodecanoylamino)butanoyl)/K30R-GLP-2(1-33);
L17K((S)-4-carboxy-4-(tridecanoylamino)butanoyl)/K30R-GLP-2(1-33);
L17K((S)-4-carboxy-4-(tetradecanoylamino)butanoyl)/K30R-GLP-2(1-33);
L17K((S)-4-carboxy-4-(pentadecanoylamino)butanoyl)/K30R-GLP-2(1-33);
L17K((S)-4-carboxy-4-(hexadecanoylamino)butanoyl)/K30R-GLP-2(1-33);
L17K((S)-4-carboxy-4-(heptadecanoylamino)butanoyl)/K30R-GLP-2(1-33);
L17K((S)-4-carboxy-4-(octadecanoylamino)butanoyl)/K30R-GLP-2(1-33);

L17K((S)-4-carboxy-4-(nonadecanoylamino)butanoyl)/ K30R-GLP-2(1-33);
L17K((S)-4-carboxy-4-(eicosanoylamino)butanoyl)/K30R-GLP-2(1-33);
L17K(4-(octanoylamino)butanoyl)/K30R-GLP-2(1-33);
L17K(4-(nonanoylamino)butanoyl)/K30R-GLP-2(1-33);
L17K(4-(decanoylamino)butanoyl)/K30R-GLP-2(1-33);
L17K(4-(undecanoylamino)butanoyl)/K30R-GLP-2(1-33);
L17K(4-(dodecanoylamino)butanoyl)/K30R-GLP-2(1-33);
L17K(4-(tridecanoylamino)butanoyl)/K30R-GLP-2(1-33);
L17K(4-(tetradecanoylamino)butanoyl)/K30R-GLP-2(1-33);
L17K(4-(pentadecanoylamino)butanoyl)/K30R-GLP-2(1-33);
L17K(4-(hexadecanoylamino)butanoyl)/K30R-GLP-2(1-33);
L17K(4-(heptadecanoylamino)butanoyl)/K30R-GLP-2(1-33);
L17K(4-(octadecanoylamino)butanoyl)/K30R-GLP-2(1-33);
L17K(4-(nonadecanoylamino)butanoyl)/K30R-GLP-2(1-33);
L17K(4-(eicosanoylamino)butanoyl)/K30R-GLP-2(1-33);
A18K(3-(hexadecanoylamino)propionyl)/K30R-GLP-2(1-33);
D21K(3-(hexadecanoylamino)propionyl)/K30R-GLP-2(1-33);
N24K(3-(hexadecanoylamino)propionyl)/K30R-GLP-2(1-33);
Q28K(3-(hexadecanoylamino)propionyl)/K30R-GLP-2(11-33);
D3E/S5K(3-(hexadecanoylamino)propionyl)/K30R/D33E-GLP-2(1-33);
D3E/S7K(3-(hexadecanoylamino)propionyl)/K30R/D33E-GLP-2(1-33);
D3E/D8K(3-(hexadecanoylamino)propionyl)/K30R/D33E-GLP-2(1-33);
D3E/E9K(3-(hexadecanoylamino)propionyl)/K30R/D33E-GLP-2(1-33);
D3E/M10K(3-(hexadecanoylamino)propionyl)/K30R/D33E-GLP-2(1-33);
D3E/N11K(3-(hexadecanoylamino)propionyl)/K30R/D33E-GLP-2(1-33);
D3E/T12K(3-(hexadecanoylamino)propionyl)/K30R/D33E-GLP-2(1-33);
D3E/I13K(3-(hexadecanoylamino)propionyl)/K30R/D33E-GLP-2(1-33);
D3E/L14K(3-(hexadecanoylamino)propionyl)/K30R/D33E-GLP-2(1-33);
D3E/D15K(3-(hexadecanoylamino)propionyl)/K30R/D33E-GLP-2(1-33);
D3E/N16K(3-(hexadecanoylamino)propionyl)/K30R/D33E-GLP-2(1-33);
D3E/L17K(3-(octanoylamino)propionyl)/K30R/D33E-GLP-2(1-33);
D3E/L17K(3-(nonanoylamino)propionyl)/K30R/D33E-GLP-2(1-33);
D3E/L17K(3-(decanoylamino)propionyl)/K30R/D33E-GLP-2(1-33);
D3E/L17K(3-(undecanoylamino)propionyl)/K30R/D33E-GLP-2(1-33);
D3E/L17K(3-(dodecanoylamino)propionyl)/K30R/D33E-GLP-2(1-33);
D3E/L17K(3-(tridecanoylamino)propionyl)/K30R/D33E-GLP-2(1-33);
D3E/L17K(3-(tetradecanoylamino)propionyl)/K30R/D33E-GLP-2(1-33);
D3E/L17K(3-(pentadecanoylamino)propionyl)/K30R/D33E-GLP-2(1-33);
D3E/L17K(3-(hexadecanoylamino)propionyl)/K30R/D33E-GLP-2(1-33);
D3E/L17K(3-(heptadecanoylamino)propionyl)/K30R/D33E-GLP-2(1-33);
D3E/L17K(3-(octadecanoylamino)propionyl)/K30R/D33E-GLP-2(1-33);
D3E/L17K(3-(nonadecanoylamino)propionyl)/K30R/D33E-GLP-2(1-33);
D3E/L17K(3-(eicosanoylamino)propionyl)/K30R/D33E-GLP-2(1-33);
D3E/L17K((S)-4-carboxy-4-(octanoylamino)butanoyl)/K30R/D33E-GLP-2(1-33);
D3E/L17K((S)-4-carboxy-4-(nonanoylamino)butanoyl)/K30R/D33E-GLP-2(1-33);
D3E/L17K((S)-4-carboxy-4-(decanoylamino)butanoyl)/K30R/D33E-GLP-2(1-33);
D3E/L17K((S)-4-carboxy-4-(undecanoylamino)butanoyl)/K30R/D33E-GLP-2(1-33);
D3E/L17K((S)-4-carboxy-4-(dodecanoylamino)butanoyl)/K30R/D33E-GLP-2(1-33);
D3E/L17K((S)-4-carboxy-4-(tridecanoylamino)butanoyl)/K30R/D33E-GLP-2(1-33);
D3E/L17K((S)-4-carboxy-4-(tetradecanoylamino)butanoyl)/K30R/D33E-GLP-2(1-33);
D3E/L17K((S)-4-carboxy-4-(pentadecanoylamino)butanoyl)/K30R/D33E-GLP-2(1-33);
D3E/L17K((S)-4-carboxy-4-(hexadecanoylamino)butanoyl)/K30R/D33E-GLP-2(1-33);
D3E/L17K((S)-4-carboxy-4-(heptadecanoylamino)butanoyl)/K30R/D33E-GLP-2(1-33);
D3E/L17K((S)-4-carboxy-4-(octadecanoylamino)butanoyl)/K30R/D33E-GLP-2(1-33);
D3E/L17K((S)-4-carboxy-4-(nonadecanoylamino)butanoyl)/K30R/D33E-GLP-2(1-33);
D3E/L17K((S)-4-carboxy-4-(eicosanoylamino)butanoyl)/K30R/D33E-GLP-2(1-33);
D3E/L17K(4-(octanoylamino)butanoyl)/K30R/D33E-GLP-2(1-33);
D3E/L17K(4-(nonanoylamino)butanoyl)/K30R/D33E-GLP-2(1-33);
D3E/L17K(4-(decanoylamino)butanoyl)/K30R/D33E-GLP-2(1-33);
D3E/L17K(4-(undecanoylamino)butanoyl)/K30R/D33E-GLP-2(1-33);
D3E/L17K(4-(dodecanoylamino)butanoyl)/K30R/D33E-GLP-2(1-33);
D3E/L17K(4-(tridecanoylamino)butanoyl)/K30R/D33E-GLP-2(1-33);
D3E/L17K(4-(tetradecanoylamino)butanoyl)/K30R/D33E-GLP-2(1-33);
D3E/L17K(4-(pentadecanoylamino)butanoyl)/K30R/D33E-GLP-2(1-33);
D3E/L17K(4-(hexadecanoylamino)butanoyl)/K30R/D33E-GLP-2(1-33);
D3E/L17K(4-(heptadecanoylamino)butanoyl)/K30R/D33E-GLP-2(1-33);
D3E/L17K(4-(octadecanoylamino)butanoyl)/K30R/D33E-GLP-2(1-33);
D3E/L17K(4-(nonadecanoylamino)butanoyl)/K30R/D33E-GLP-2(1-33);
D3E/L17K(4-(eicosanoylamino)butanoyl)/K30R/D33E-GLP-2(1-33);
D3E/A18K(3-(hexadecanoylamino)propionyl)/K30R/D33E-GLP-2(1-33);

D3E/D21 K(3-(hexadecanoylamino)propionyl)/K30R/D33E-GLP-2(1-33);

D3E/N24K(3-(hexadecanoylamino)propionyl)/K30R/D33E-GLP-2(1-33); and

D3E/Q28K(3-(hexadecanoylamino)propionyl)/K30R/D33E-GLP-2(1-33).

78c. A method of preparing a physically stable pharmaceutical formulation of a GLP-2 derivative, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, said method comprising preparing a formulation containing the GLP-2 derivative, and a buffer, wherein said GLP-2 derivative is present in a concentration from 0.1 mg/ml to 100 mg/ml, and wherein said formulation has a pH from 7.0 to 10.

79c. The method according to embodiment 82c, wherein said pharmaceutical formulation is as defined in any of embodiments 1c-77c.

80c. A composition comprising a GLP-2 derivative, and a buffer, or a freeze-dried formulation thereof, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said composition has a pH from 7.0 to 10.

81c. The composition according to embodiment 80c, further comprising water.

82c. A composition comprising an aqueous solution of a GLP-2 derivative, and a buffer, wherein said GLP-2 derivative is a GLP-2 peptide, wherein a lipophilic substituent is attached, optionally via a spacer, to one or more amino acid residues at a position relative to the amino acid sequence of SEQ ID NO:1 independently selected from the list consisting of S5, S7, D8, E9, M10, N11, T12, I13, L14, D15, N16, L17, A18, D21, N24, and Q28, wherein said GLP-2 derivative is present in a concentration from 0.1 mg/ml to 100 mg/ml, and wherein said composition has a pH from 7.0 to 10.

In the present context the three-letter or one-letter indications of the amino acids have been used in their conventional meaning as indicated in table 1. Unless indicated explicitly, the amino acids mentioned herein are L-amino acids. Further, the left and right ends of an amino acid sequence of a peptide are, respectively, the N- and C-termini unless otherwise specified.

TABLE 1

| Abbreviations for amino acids: | | |
|---|---|---|
| Amino acid | Tree-letter code | One-letter code |
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

The present invention is further illustrated by the following examples which, however, are not to be construed as limiting the scope of protection. The features disclosed in the foregoing description and in the following examples may, both separately and in any combination thereof, be material for realising the invention in diverse forms thereof.

BRIEF DESCRIPTION OF THE DRAWINGS

FIG. 3 Sequence alignment of the highly conserved GLP-2 peptide. Amino acid residues in bold represent those that differ from the human GLP-2 sequence.

FIG. 4 Quantification of GLP-2R RNA distribution in various rat tissue.

FIG. 6 Examples with chemical structure of the use of different spacers according to the invention with the lipophilic substituent being a hexadecanoyl.

FIG. 9. Bioassay in mice. Dose-Response study of GLP-2 derivatives. Residuals of relative small intestinal weight data.

FIG. 12. SEQ ID NO. 1, SEQ ID NO. 2, and SEQ ID NO. 3.

EXAMPLES

Figure 1:
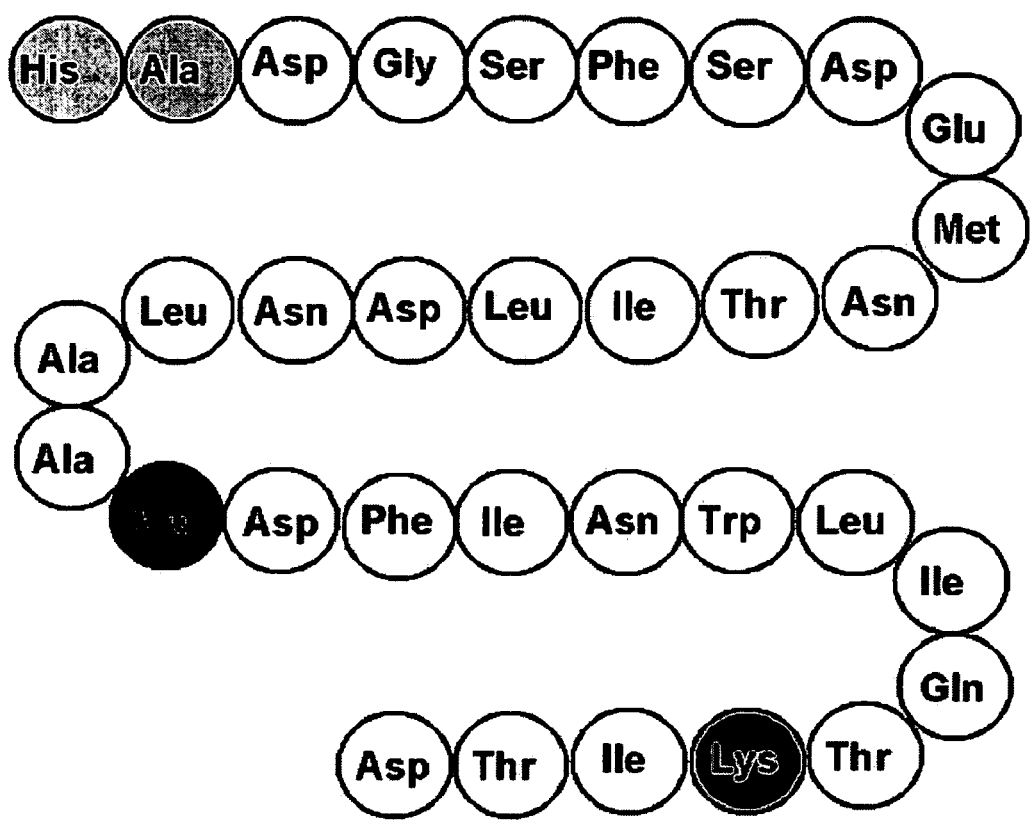
FIG. 1 The amino acid sequence of the 33 residues human GLP-2. The N-terminal His-Ala indicates the sequence cleaved of aminopeptidase dipeptidyl peptidase IV during metabolism of GLP-2. The Arg20 and Lys30 residues are the two basic amino acid residues in GLP-2.
Figure 2:
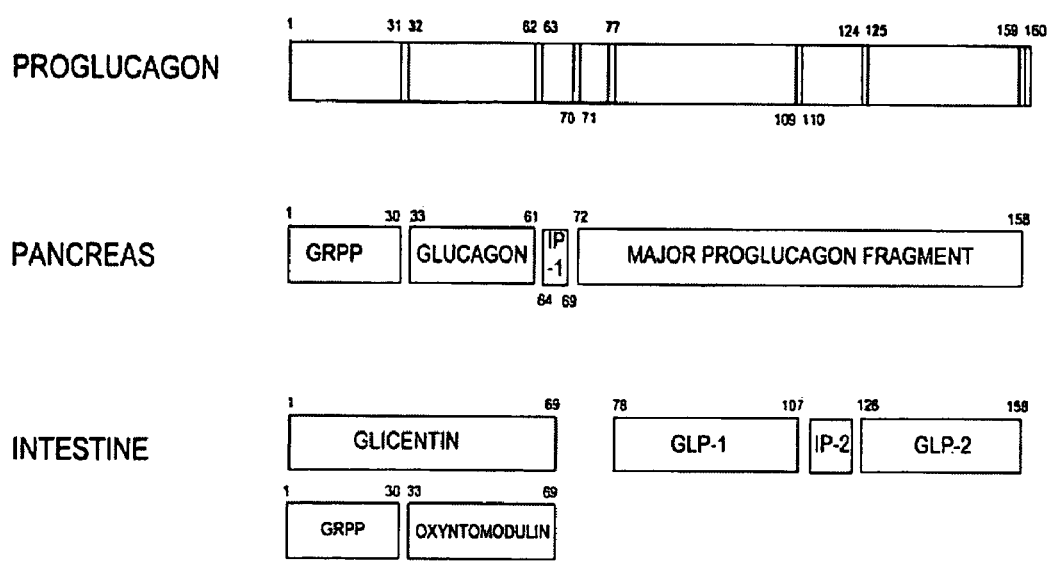
FIG. 2 Tissue-specific processing of proglugacon in pancreas and intestine.
Figure 5:
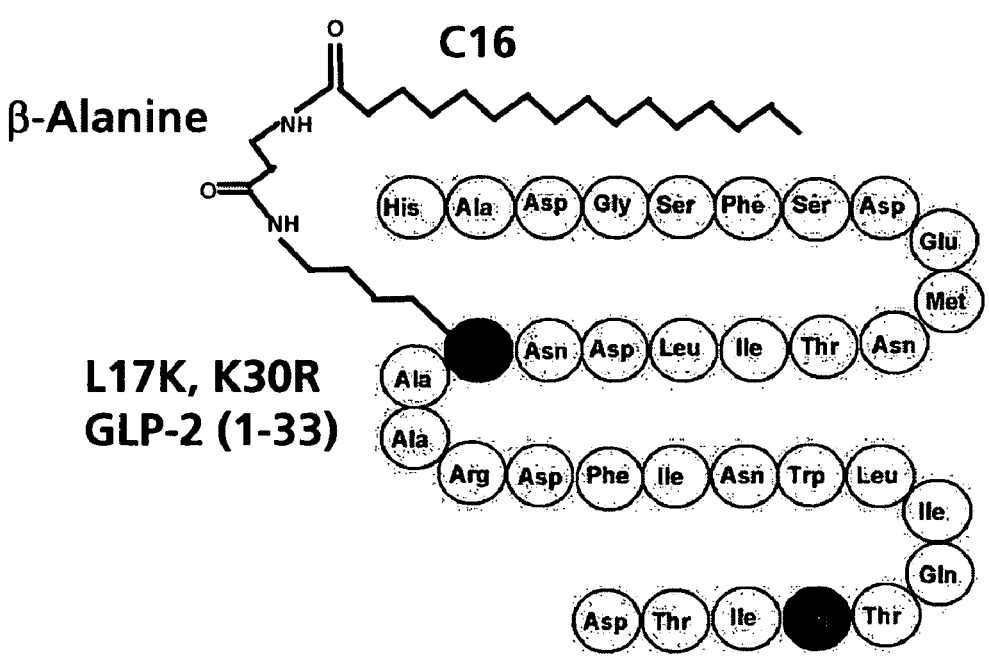
FIG. 5 L17K/K30R-GLP-2 (1-33) acylated with β-alanine C16.

The following abbreviations are used:

| | |
|---|---|
| DDE: | 1-(4,4-dimethyl-2,6-dioxocyclohex-1-ylidene)ethyl. |
| DIC: | N,N'-diisopropylcarbodiimide. |
| DIEA: | diisopropylethylamine. |
| HBTU: | 2-(1H-Benzotriazole-1-yl)-1,1,3,3-tetramethyluronium hexafluoro phosphate. |

-continued

| HOAt: | N-hydroxy-9-azabenzotriazole. |
| TNBS: | 2,4,6 trinitro benzenesulfonic acid. |
| DMF: | N,N-Dimethylformamide. |
| DCC: | N,N-Dicyclohexylcarbodiimide. |
| NMP: | N-Methyl-2-pyrrolidone. |
| EDPA: | N-Ethyl-N,N-diisopropylamine. |
| EGTA: | Ethylene glycol-bis(β-aminoethyl ether)-N,N,N',N'-tetraacetic acid. |
| GTP: | Guanosine 5'-triphosphate. |
| TFA: | Trifluoroacetic acid. |
| THF: | Tetrahydrofuran. |

H-Glu(OH)—OBu$^t$: L-Glutamic acid α-tert-butyl ester.
Cap-ONSu: Octanoic acid 2,5-dioxopyrrolidin-1-yl ester.
Lau-ONSu: Dodecanoic acid 2,5-dioxopyrrolidin-1-yl ester.
Myr-ONSu: Tetradecanoic acid 2,5-dioxopyrrolidin-1-yl ester.
Pal-ONSu: Hexadecanoic acid 2,5-dioxopyrrolidin-1-yl ester.
Ste-ONSu: Octadecanoic acid 2,5-dioxopyrrolidin-1-yl ester.
HPLC: High Performance Liquid Chromatography.
amu: atomic mass units.
Lit-Glu(ONSu)-OBu$^t$: N$^α$-Lithochoyl-L-glutamic acid α-t-butyl ester γ-2,5-dioxopyrrolidin-1-yl ester.
Cap-Glu(ONSu)-OBu$^t$: N$^α$-Octanoyl-L-glutamic acid α-t-butyl ester γ-2,5-dioxopyrrolidin-1-yl ester.
Cac-Glu(ONSu)-OBu$^t$: N$^α$-Decanoyl-L-glutamic acid α-t-butyl ester γ-2,5-dioxopyrrolidin-1-yl ester.
Lau-Glu(ONSu)-OBu$^t$: N$^α$-Dodecanoyl-L-glutamic acid α-t-butyl ester γ-2,5-dioxopyrrolidin-1-yl ester.
Myr-Glu(ONSu)-OBu$^t$: N$^α$-Tetradecanoyl-L-glutamic acid α-t-butyl ester γ-2,5-dioxopyrrolidin-1-yl ester.
Pal-Glu(ONSu)-OBu$^t$: N$^α$-Hexadecanoyl-(L)-glutamic acid α-t-butyl-γ-2,5-dioxopyrrolidin-1-yl diester.
Ste-Glu(ONSu)-OBu$^t$: N$^α$-Octadecanoyl-(L)-glutamic acid α-t-butyl-γ-2,5-dioxopyrrolidin-1-yl diester.
Lau-β-Ala-ONSu: N$^β$-Dodecanoyl-β-alanine 2,5-dioxopyrrolidin-1-yl ester.
Myr-β-Ala-ONSu: N$^β$-Tetradecanoyl-β-alanine 2,5-dioxopyrrolidin-1-yl ester
Pal-β-Ala-ONSu: N$^β$-Hexadecanoyl-α-alanine 2,5-dioxopyrrolidin-1-yl ester.
Lau-GABA-ONSu: N$^γ$-Dodecanoyl-γ-aminobutyric acid 2,5-dioxopyrrolidin-1-yl ester.
Myr-GABA-ONSu: N$^γ$-Tetradecanoyl-γ-aminobutyric acid 2,5-dioxopyrrolidin-1-yl ester.
Pal-GABA-ONSu: N$^γ$-Hexadecanoyl-γ-aminobutyric acid 2,5-dioxopyrrolidin-1-yl ester.
Ste-GABA-ONSu: N$^γ$-Octadecanoyl-γ-aminobutyric acid 2,5-dioxopyrrolidin-1-yl ester.
Pal-Isonip-ONSu: N-Hexadecanoyl-piperidine-4-carboxylic acid 2,5-dioxopyrrolidin-1-yl ester.
Pal-Glu(OBu$^t$)-ONSu: N$^α$-Hexadecanoyl-L-glutamic acid α-2,5-dioxopyrrolidin-1-yl ester γ-t-butyl ester.
HOOC—(CH$_2$)$_6$—COONSu: ω-Carboxyheptanoic acid 2,5-dioxopyrrolidin-1-yl ester.
HOOC—(CH$_2$)$_{10}$—COONSu: ω-Carboxyundecanoic acid 2,5-dioxopyrrolidin-1-yl ester.
HOOC—(CH$_2$)$_{12}$—COONSu: ω-Carboxytridecanoic acid 2,5-dioxopyrrolidin-1-yl ester.
HOOC—(CH$_2$)$_{14}$—COONSu: ω-Carboxypentadecanoic acid 2,5-dioxopyrrolidin-1-yl ester.
HOOC—(CH$_2$)$_{16}$—COONSu: ω-Carboxyheptadecanoic acid 2,5-dioxopyrrolidin-1-yl ester.
HOOC—(CH$_2$)$_{18}$—COONSu: ω-Carboxynonadecanoic acid 2,5-dioxopyrrolidin-1-yl ester.

Example 1

Preparation of Derivatives of GLP-2 Peptide Analogs by Peptide Synthesis.

The acylation is done on the fully protected resin-bound peptide where only the ε-amino group to be acylated has been deprotected. The appropriately protected resin bound peptide is synthesized using Fmoc chemistry, eg.:
↓Boc-[1-33,Lys(Dde)]-Resin
↓2% Hydrazine/DMF treatment to remove the Dde group.
↓Acylation with Fmoc-Glu(γ-OH)-OBu$^t$ via HOAt/DIC/DIEA/NMP.
↓Piperidine treatment to remove the Fmoc group.
↓Acylate with C16 acid via HOAt/DIC/DIEA/NMP.
↓TFA deprotection.
↓HPLC-Purification
↓Lyophilization
↓Analysis by LC-MS and analytical HPLC.

The spacer and fatty acid chain length may then be varied. Keeping the acylation position fixed, three spacers: γ-Glutamic acid, γ-aminobutyric acid, β-Alanine and no spacer, and three fatty acids (C12, C14 and C16) as well as cholic, lithocholic, and pentylbenzoic acids were tested.

Synthesis of Protected Peptidyl Resin:
Protected amino acid derivatives used:
Fmoc-Ala-OH, Fmoc-Arg(Pmc)-OH, Fmoc-Asn(Trt)-OH, Fmoc-Asp(OBut)-OH, Boc-His(Boc)-OH, Fmoc-His(Trt)-OH, Fmoc-Gln(Trt)-OH, Fmoc-Glu(OBut)-OH, Fmoc-Gly-OH, Fmoc-Ile-OH, Fmoc-Leu-OH, Fmoc-Lys(Boc)-OH, Fmoc-Lys(Dde)-OH, Boc-Lys(Fmoc)-OH, Fmoc-Met-OH, Fmoc-Phe-OH, Fmoc-Ser(But)-OH, Fmoc-Thr(But)-OH, Fmoc-Trp(Boc)-OH Synthesis of N$^α$-hexadecanoyl-Glu(ONSu)-OBu$^t$ To a suspension of H-Glu(OH)—OBu$^t$ (4.2 g, 20.6 mmol), DMF (500 ml) and EDPA (2.65 g, 20.6 mmol) was added drop by drop a solution of Pal-ONSu (7.3 g, 20.6 mmol) in DMF (100 ml). The reaction mixture was stirred for 64 h at room temperature and then concentrated in vacuo to a total volume of 20 ml. The residue was partitioned between 10% aqueous citric acid (300 ml) and ethyl acetate (250 ml), and the phases were separated. The organic phase was concentrated in vacuo and the residue dissolved in DMF (50 ml). The resulting solution was added drop by drop to a 10% aqueous solution of citric acid (500 ml) kept at 0° C. The precipitated compound was collected and washed with iced water and dried in a vacuum drying oven. The dried compound was dissolved in DMF (45 ml) and HONSu (2.15 g, 18.7 mmol) was added. To the resulting mixture was added a solution of N,N'-dicyclohexylcarbodiimide (3.5 g, 17 mmol) in dichloromethane (67 ml). The reaction mixture was stirred for 16 h at room temperature, and the precipitated compound was filtered off. The precipitate was recrystallised from n-heptane/2-propanol to give the title compound (6.6 g, 72%).

Example 2

Synthesis of D3E/L17K((S)-4-carboxy-4-(hexadecanoylamino)butanoyl)/K30R/D33E-GLP-2(1-33)

2.a Synthesis of the Protected Peptidyl Resin:
The protected peptidyl resin was synthesized according to the Fmoc strategy on an Applied Biosystems 431A peptide synthesizer in 0.25 mmol scale using the manufacturer supplied FastMoc UV protocols which employ HBTU (2-(1H-Benzotriazol-1-yl-)-1,1,3,3 tetramethyluronium hexafluorophosphate) mediated couplings in NMP (N-methyl pyrrolidone), and UV monitoring of the deprotection of the Fmoc protection group. The starting resin (400 mg) used for the synthesis was (4-((2',4'-dimethoxyphenyl)-(Fmoc-Glu (OBut)-O-p-Benzyloxybenzyl resin (Wang resin) (Novabiochem, Bad Soden, Germany. cat. #: 04-12-2052) with a substitution capacity of 0.53 mmol/g.

The protected aminoacid derivatives used were Fmoc-Ala-OH, Fmoc-Arg(Pmc)-OH, Fmoc-Asn(Trt)-OH, Fmoc-Asp (OBut)-OH, Boc-His(Boc)-OH, Fmoc-Gln(Trt)-OH, Fmoc-Glu(OBut)-OH, Fmoc-Gly-OH, Fmoc-Ile-OH, Fmoc-Leu-OH, Fmoc-Lys(DDE)-OH, Fmoc-Met-OH, Fmoc-Phe-OH, Fmoc-Ser(But)-OH, Fmoc-Thr(But)-OH, Fmoc-Trp(Boc)-OH.

The yield was 870 mg peptidyl resin.

2.b Dde Removal and Acylation

To the protected peptidyl resin resulting from (1.a) (290 mg, 72 pmol) is added NMP (N-Methyl pyrrolidon)(2 ml), and a freshly prepared solution of hydrazine hydrate 2% in NMP (10 ml). The reaction mixture is stirred for 3 min at room temperature, and then filtered (glas filter). More hydrazine solution (22 ml) is added on the filter, the hydrazine is left to react for 15 nm on the filter, and then filtered off by applying vacuum.

The resin is then washed extensively with NMP, dichloromethane and NMP.

To the Dde deprotected resin in NMP ($\approx$5 ml), is added N—$C_{16}$-Glu-$\alpha$-OtBu-$\gamma$-ONSu ($N^{\alpha}$-hexadecanoyl-L-glutamic acid $\alpha$-tert-butyl ester $\gamma$-succinimidyl ester) (4 eq), and DIEA (diisopropylethylamine)(4 eq). The reaction mixture is stirred for 1 h at room temperature. Then more N—$C_{16}$-Glu-$\alpha$-OtBu-$\gamma$-ONSu (4 eq) is added, together with DIEA (4 eq). The reaction mixture is stirred overnight at room temperature. The reaction mixture is filtered and the resin is washed extensively with NMP, dichloromethane, 2-propanol, methanol and diethyl ether.

2.c Cleavage of the Acylated Peptide from the Resin:

The peptide is cleaved from the protected peptidyl resin by stirring with a mixture of TFA (trifluoro acetic acid) (2 ml), triisopropylsilane (50 µl) and water (50 µl) for 60 min at room temperature. The cleavage mixture is filtered and the filtrate is concentrated to approximately 1 ml by a stream of nitrogen. The crude peptide is precipitated from this oil with diethyl ether (49.5 ml), washed 3 times with diethyl ether (3 times 50 ml) and dried to a white powder.

2.d Purification of the Peptide:

The crude peptide is dissolved in water/acetonitrile (65:35) (100 ml) adjusted to pH 7.5 with $NH_4OH$ and purified by semipreparative HPLC on a 25 mm×250 mm column packed with 7µ C-18 silica. The column is eluted with a gradient of 50 to 70% acetonitrile against 0.1% TFA/water at 10 ml/min at a temperature of 40° C. for 47 nm. The peptide containing fractions are collected, diluted with 3 volumes of water and lyophilized.

The final product obtained is characterized by RP-HPLC/ion spray mass spectrometry (LC-MS) (retention time and molecular mass) and by analytical RP-HPLC (retention time and peptide amount). The peptide amount is calculated by comparing the UV detector response with that of a GLP-2 standard where the amount had been determined by amino acid analysis. The RP-HPLC analysis is performed on a Vydac 218TP54 4.6 mm×250 mm 5µ C-18 silica column (The Separations Group, Hesperia) with UV detection at 214 nm. The column is equilibrated with 0.1% $TFA/H_2O$ and eluted by a gradient of 0 to 90% $CH_3CN$ against 0.1% TFA/water for 50 min at 42° C., with a flow of 0.5 ml/mn. The retention time is found to be 35.8 min, and the peptide yield to be 29.3 mg.

The LC-MS analysis is performed using a Symmetry 3.0 mm×150 mm 5 µC-18 silica column (Waters, Milford Mass., USA) which is eluted at 1 ml/min at room temperature. It is equilibrated with 5% $CH_3CN/0.1\% TFA/H_2O$ and eluted by a gradient of 5% $CH_3CN/0.1\% TFA/H_2O$ to 90% $CH_3CN/0.1\% TFA/H_2O$ during 15 min. Besides the UV detection at 214 nm, a fraction of the column eluate is introduced into the ionspray interface of a PE-Sciex API 100 mass spectrometer. The mass range 300-3000 amu is scanned every 2 seconds during the run.

Using these conditions, the retention time of the product as determined from the UV trace is found to be 6.1 min, and the molecular mass is found to be 4204.4 amu, which is in agreement with the expected structure within the experimental error of the method (±1 amu).

Example 3

Synthesis of D3E/K30R/D33E/34K((S)-4-carboxy-4-(hexadecanoylamino)butanoyl)-GLP-2(1-33) (Lys residue added in C-Terminal)

The starting resin used for the synthesis was Fmoc-Lys (Dde)-2Cl-Trityl resin, prepared from Fmoc-Lys(Dde)-OH and 2-Cl-Trityl chloride resin (Novabiochem, Bad Soden, Germany. cat. #: 01-64-0114) after the procedure described by the manufacturer (substitution capacity of 1.13 mmol/g).

The protected peptidyl resin (200 mg, 85 mmol) was synthesized according to the Fmoc strategy as in example (2.a), Dde deprotected and acylated with N—$C_{16}$-Glu-$\alpha$-OtBu-$\gamma$-ONSu ($N^{\alpha}$-hexadecanoyl-L-glutamic acid $\alpha$-tert-butyl ester $\gamma$-succinimidyl ester) as described in (2.b). Cleavage from the resin and purification were done according to (2.c and 2.d).

The retention time obtained under the elution conditions described in (2.d) was 36.7 min, and the peptide yield was 1.3 mg.

By LC-MS analysis of the product, a retention time of 6.6 min was found from the UV trace, and the molecular mass was found to be 4319.4 amu, which is in agreement with the expected structure within the experimental error of the method (±1 amu).

Example 4

Synthesis of D3E/L17K(4-(hexadecanoylamino) butanoyl)/K30R/D33E-GLP-2(1-33)

The protected peptidyl resin (200 mg, 21 µmol) was synthesized according to the Fmoc strategy as in example (2.a), Dde deprotected and acylated with $C_{16}$-GABA-ONSu (N-hexadecanoyl-$\gamma$-amino-butyric acid succinimidyl ester) as described in (2.b) for acylation with N—$C_{16}$-Glu-$\alpha$-OtBu-$\gamma$-ONSu. Cleavage from the resin and purification were done according to (2.c and 2.d).

Cleavage from the resin and purification were done according to example (2.c) and (2.d). The retention time obtained under the elution conditions described in (2.d) was 36.5 min, and the peptide yield was 1.9 mg.

By LC-MS analysis of the product, a retention time of 4.9 min was found from the UV trace, and the molecular mass was found to be 4161.0 amu, which is in agreement with the expected structure within the experimental error of the method (±1 amu).

Example 5

Synthesis of D3E/L17K(3-(hexadecanoylamino)propionyl)K30R/D33E-GLP-2(1-33)

The protected peptidyl resin (200 mg, 21 µmol) was synthesized according to the Fmoc strategy as in example (2.a), Dde deprotected and acylated with $C_{16}$-oyl-β-Ala-ONSu (N-hexadecanoyl-β-alanine-succinimidyl ester) as described in (2.b) for acylation with N—$C_{16}$-Glu-α-OtBu-γ-ONSu. Cleavage from the resin and purification were done according to (2.c and 2.d).

Cleavage from the resin and purification were done according to (2.c and 2.d). The retention time obtained under the elution conditions described in (2.d) was 36.0 min, and the peptide yield was 2.8 mg.

By LC-MS analysis of the product, a retention time of 4.7 min was found from the UV trace, and the molecular mass was found to be 4146.6 amu, which is in agreement with the expected structure within the experimental error of the method (±1 amu).

Example 6

Synthesis of D3E/L17K(hexadecanoyl)/K30R/D33E-GLP-2(1-33)

The protected peptidyl resin (200 mg, 21 µmol) was synthesized according to the Fmoc strategy as in example (2.a), Dde deprotected and acylated with $C_{16}$-oyl-ONSu (hexadecanoic acid succinimidyl ester) as described in (2.b) for acylation with N—$C_{16}$-Glu-α-OtBu-γ-ONSu.

Cleavage from the resin and purification were done according to (2.c and 2.d).

The retention time obtained under the elution conditions described in (2.d) was 36.9 min, and the peptide yield was 2.6 mg.

By LC-MS analysis of the product, a retention time of 5.1 min was found from the UV trace, and the molecular mass was found to be 4076.4 amu, which is in agreement with the expected structure within the experimental error of the method (±1 amu).

Example 7

Synthesis of D3E/L17K(choloyl)/K30R/D33E-GLP-2(1-33)

The protected peptidyl resin (250 mg, 27 µmol) was synthesized as in example (2.a). The Dde protective group is removed as in example (2.b).

To a mixture of cholic acid (817 mg), HOAt (N-hydroxy-9-azabenzotriazole) (135 mg) and DIC (N,N'-diisopropylcarbodiimide) (155 pl) is added a mixture of NMP and dichloromethane (1:1 v/v) (4 ml). The reaction mixture is stirred at ambient temperature for 15 min. The peptidyl resin is then added, together with DIEA (diisopropylethylamine) (170 µl). The reaction mixture is stirred overnight at ambient temperature. The resin is then filtered, washed thoroughly with NMP, and then with dichloromethane, 2-propanol, methanol and diethylether. Cleavage from the resin and purification were done according to (2.c and 2.d).

The retention time obtained under the elution conditions described in (2.d) was 30.0 min, and the peptide yield was 2.2 mg.

By LC-MS analysis of the product, a retention time of 4.2 min was found from the UV trace, and the molecular mass was found to be 4228.2 amu, which is in agreement with the expected structure within the experimental error of the method (±1 amu).

Example 8

Synthesis of 1H((S)-4-carboxy-4-(hexadecanoylamino)butanoyl)/D3E/K30R/D33E-GLP-2(1-33)

8.a Synthesis of the Protected Peptidyl Resin:

The protected peptidyl resin was synthesized according to the Fmoc strategy on an Applied Biosystems 431A peptide synthesizer in 0.25 mmol scale using the manufacturer supplied FastMoc UV protocols which employ HBTU (2-(1H-Benzotriazol-1-yl-)-1,1,3,3 tetramethyluronium hexafluorophosphate) mediated couplings in NMP (N-methyl pyrrolidone), and UV monitoring of the deprotection of the Fmoc protection group. The starting resin (454 mg, 0.25 mmoles) used for the synthesis was (4-((2',4'-dimethoxyphenyl)-(Fmoc-Glu(OBut)-O-p-Benzyloxybenzyl resin (Wang resin) (Novabiochem, Bad Soden, Germany. cat. #: 04-12-2052) with a substitution capacity of 0.55 mmol/g.

The protected aminoacid derivatives used were Fmoc-Ala-OH, Fmoc-Arg(Pmc)-OH, Fmoc-Asn(Trt)-OH, Fmoc-Asp(OBut)-OH, Fmoc-His(Trt)-OH, Fmoc-Gln(Trt)-OH, Fmoc-Glu(OBut)-OH, Fmoc-Gly-OH, Fmoc-Ile-OH, Fmoc-Leu-OH, Fmoc-Met-OH, Fmoc-Phe-OH, Fmoc-Ser(But)-OH, Fmoc-Thr(But)-OH, Fmoc-Trp(Boc)-OH.

The yield was 1707 mg peptidyl resin.

8.b Acylation

To the peptidyl resin (200 mg, 29 µmoles) in NMP (≈5 ml), is added N—$C_{16}$-Glu-α-OtBu-γ-ONSu ($N^{\alpha}$-hexadecanoyl-L-glutamic acid α-tert-butyl ester γ-succinimidyl ester) (4 eq), and DIEA (diisopropylethylamine) (4 eq). The reaction mixture is stirred for 1 h at room temperature. Then more N—$C_{16}$-Glu-α-OtBu-γ-ONSu (4 eq) is added, together with DIEA (4 eq). The reaction mixture is stirred overnight at room temperature. The reaction mixture is filtered and the resin is washed extensively with NMP, dichloromethane, 2-propanol, methanol and diethyl ether.

Cleavage from the resin and purification were done according to (2.c and 2.d). The retention time obtained under the elution conditions described in (2.d) was 37.0 min, and the peptide yield was 6.0 mg.

By LC-MS analysis of the product, a retention time of 6.5 min was found from the UV trace, and the molecular mass was found to be 4189.8 amu, which is in agreement with the expected structure within the experimental error of the method (±1 amu).

Example 9

Synthesis of H1K-$N^{\epsilon}$-((S)-4-carboxy-4-(hexadecanoylamino)butanoyl)/D3E/K30R/D33E-GLP-2(1-33)

9.a Synthesis of the Protected Peptidyl Resin:

The protected peptidyl resin was synthesized according to the Fmoc strategy on an Applied Biosystems 431A peptide synthesizer in 0.25 mmol scale using the manufacturer supplied FastMoc UV protocols which employ HBTU (2-(1H-Benzotriazol-1-yl-)-1,1,3,3 tetramethyluronium hexafluorophosphate) mediated couplings in NMP (N-methyl pyrrolidone), and UV monitoring of the deprotection of the Fmoc protection group. The starting resin (434 mg, 0.24 mmoles) used for the synthesis was (4-((2',4'-dimethoxyphenyl)-(Fmoc-Glu(OBut)-O-p-Benzyloxybenzyl resin (Wang resin) (Novabiochem, Bad Soden, Germany. cat. #: 04-12-2052) with a substitution capacity of 0.55 mmol/g.

The protected aminoacid derivatives used were Fmoc-Ala-OH, Fmoc-Arg(Pmc)-OH, Fmoc-Asn(Trt)-OH, Fmoc-Asp(OBut)-OH, Fmoc-His(Trt)-OH, Fmoc-Gln(Trt)-OH, Fmoc-Glu(OBut)-OH, Fmoc-Gly-OH, Fmoc-Ile-OH, Fmoc-Leu-OH, Boc-Lys(Fmoc)-OH, Fmoc-Met-OH, Fmoc-Phe-OH, Fmoc-Ser(But)-OH, Fmoc-Thr(But)-OH, Fmoc-Trp(Boc)-OH.

The yield was 1551 mg peptidyl resin.

9.b Acylation

To the peptidyl resin (200 mg, 31 µmoles) in NMP (≈5 ml), is added N—$C_{16}$-Glu-α-OtBu-γ-ONSu (N$^\alpha$-hexadecanoyl-L-glutamic acid α-tert-butyl ester γ-succinimidyl ester) (4 eq), and DIEA (diisopropylethylamine)(4 eq). The reaction mixture is stirred for 1 h at room temperature. Then more N—$C_{16}$-Glu-α-OtBu-γ-ONSu (4 eq) is added, together with DIEA (4 eq). The reaction mixture is stirred overnight at room temperature. The reaction mixture is filtered and the resin is washed extensively with NMP, dichloromethane, 2-propanol, methanol and diethyl ether.

Cleavage from the resin and purification were done according to (2.c and 2.d).

The retention time obtained under the elution conditions described in (2.d) was 36.8 min, and the peptide yield was 4.4 mg.

By LC-MS analysis of the product, a retention time of 6.4 min was found from the UV trace, and the molecular mass was found to be 4180.2 amu, which is in agreement with the expected structure within the experimental error of the method (±1 amu).

Example 10

Synthesis of H1K-N$^\alpha$-((S)-4-carboxy-4-(hexadecanoylamino)butanoyl)/D3E/K30R/D33E-GLP-2(1-33)

10.a Synthesis of the Protected Peptidyl Resin:

The protected peptidyl resin was synthesized according to the Fmoc strategy on an Applied Biosystems 431A peptide synthesizer in 0.25 mmol scale using the manufacturer supplied FastMoc UV protocols which employ HBTU (2-(1H-Benzotriazol-1-yl-)-1,1,3,3 tetramethyluronium hexafluorophosphate) mediated couplings in NMP (N-methyl pyrrolidone), and UV monitoring of the deprotection of the Fmoc protection group. The starting resin (455 mg, 0.25 mmoles) used for the synthesis was (4-((2',4'-dimethoxyphenyl)-(Fmoc-Glu(OBut)-O-p-Benzyloxybenzyl resin (Wang resin) (Novabiochem, Bad Soden, Germany. cat. #: 04-12-2052) with a substitution capacity of 0.55 mmol/g.

The protected aminoacid derivatives used were Fmoc-Ala-OH, Fmoc-Arg(Pmc)-OH, Fmoc-Asn(Trt)-OH, Fmoc-Asp(OBut)-OH, Fmoc-His(Trt)-OH, Fmoc-Gln(Trt)-OH, Fmoc-Glu(OBut)-OH, Fmoc-Gly-OH, Fmoc-Ile-OH, Fmoc-Leu-OH, Fmoc-Lys(Dde)-OH, Fmoc-Met-OH, Fmoc-Phe-OH, Fmoc-Ser(But)-OH, Fmoc-Thr(But)-OH, Fmoc-Trp(Boc)-OH.

The yield was 1167 mg peptidyl resin.

10.b Acylation

To the peptidyl resin (200 mg, 43 µmoles) in NMP (≈5 ml), is added N—$C_{16}$-Glu-α-OtBu-γ-ONSu (N$^\alpha$-hexadecanoyl-L-glutamic acid α-tert-butyl ester γ-succinimidyl ester) (4 eq), and DIEA (diisopropylethylamine) (4 eq). The reaction mixture is stirred for 1 h at room temperature. Then more N—$C_{16}$-Glu-α-OtBu-γ-ONSu (4 eq) is added, together with DIEA (4 eq). The reaction mixture is stirred overnight at room temperature. The reaction mixture is filtered and the resin is washed extensively with NMP, dichloromethane, 2-propanol, methanol and diethyl ether.

The Dde protective group is then removed as in (2.b).

Cleavage from the resin and purification were done according to (2.c and 2.d).

The retention time obtained under the elution conditions described in (2.d) was 37.0 min, and the peptide yield was 4.0 mg.

By LC-MS analysis of the product, a retention time of 6.5 min was found from the UV trace, and the molecular mass was found to be 4180.2 amu, which is in agreement with the expected structure within the experimental error of the method (±1 amu).

The characterisation includes retention time in an analytical RP-HPLC system, retention time in an LC-MS system and a molecular weight determination in the LC-MS system. The total amount of peptide synthesised were calculated by comparison of peak areas with those from a GLP-2 standard. The results obtained are summarised in Table 2.

TABLE 2

HPLC and mass spectrometry characterisation of synthesized GLP-2 derivatives. HPLC, rt (mn): retention time in minutes in the analytical RP-HPLC system (see methods). LS-MS, rt (mn): retention time in minutes in the RP-HPLC/ionspray mass spectrometry system (see methods). MW: Molecular weight.

| Example and compound number | Prepared as in ex. | Peptide | Acyl-site | Spacer | Fatty acid | HPLC, rt (mn) | LC-MS, rt (mn) | Found MW | Calc. MW | Amount (mg) |
|---|---|---|---|---|---|---|---|---|---|---|
| 8 |  | [Glu$^3$, Arg$^{30}$, Glu$^{33}$] GLP-2 | α-His1 | γ-Glu | N—C16oyl(Glu) | 37.0 | 6.5 | 4189.8 | 4190.2 | 5.99 |
| 10 |  | [Lys$^1$, Glu$^3$, Arg$^{30}$, Glu$^{33}$] GLP-2 | α-Lys1 | γ-Glu | N—C16oyl(Glu) | 37.0 | 6.5 | 4180.2 | 4181.3 | 4.00 |
| 9 |  | [Lys$^1$, Glu$^3$, Arg$^{30}$, Glu$^{33}$] GLP-2 | ε-Lys1 | γ-Glu | N—C16oyl(Glu) | 36.8 | 6.4 | 4180.2 | 4181.3 | 4.38 |
| 11 | 2 | [Lys$^2$, Glu$^3$, Arg$^{30}$, Glu$^{33}$] GLP-2 | ε-Lys2 | γ-Glu | N—C16oyl(Glu) | 36.3 | 6.6 | 4247.4 | 4247.3 | 4.41 |

TABLE 2-continued

HPLC and mass spectrometry characterisation of synthesized GLP-2
derivatives. HPLC, rt (mn): retention time in minutes in the analytical
RP-HPLC system (see methods). LS-MS, rt (mn): retention time in minutes
in the RP-HPLC/ionspray mass spectrometry system (see methods).
MW: Molecular weight.

| Example and compound number | Prepared as in ex. | Peptide | Acyl-site | Spacer | Fatty acid | HPLC, rt (mn) | LC-MS, rt (mn) | Found MW | Calc. MW | Amount (mg) |
|---|---|---|---|---|---|---|---|---|---|---|
| 12 | 2 | [Lys$^3$, Arg$^{30}$, Glu$^{33}$] GLP-2 | ε-Lys3 | γ-Glu | N—C16oyl(Glu) | 36.2 | 6.2 | 4189.8 | 4189.3 | 4.45 |
| 13 | 2 | [Glu$^3$, Lys$^4$, Arg$^{30}$, Glu$^{33}$] GLP-2 | ε-Lys4 | γ-Glu | N—C16oyl(Glu) | 36.5 | 6.6 | 4261.8 | 4261.4 | 3.24 |
| 14 | 2 | [Glu$^3$, Lys$^5$, Arg$^{30}$, Glu$^{33}$] GLP-2 | ε-Lys5 | γ-Glu | N—C16oyl(Glu) | 36.8 | 6.4 | 4231.8 | 4231.3 | 1.89 |
| 15 | 2 | [Glu$^3$, Lys$^6$, Arg$^{30}$, Glu$^{33}$] GLP-2 | ε-Lys6 | γ-Glu | N—C16oyl(Glu) | 35.3 | 6.3 | 4169.4 | 4171.2 | 4.40 |
| 16 | 2 | [Glu$^3$, Lys$^7$, Arg$^{30}$, Glu$^{33}$] GLP-2 | ε-Lys7 | γ-Glu | N—C16oyl(Glu) | 37.4 | 6.6 | 4231.6 | 4230.9 | 34.15 |
| 17 | 2 | [Glu$^3$, Lys$^8$, Arg$^{30}$, Glu$^{33}$] GLP-2 | ε-Lys8 | γ-Glu | N—C16oyl(Glu) | 36.3 | 6.5 | 4204.2 | 4202.8 | 31.10 |
| 18 | 2 | [Glu$^3$, Lys$^9$, Arg$^{30}$, Glu$^{33}$] GLP-2 | ε-Lys9 | γ-Glu | N—C16oyl(Glu) | 36.8 | 6.5 | 4189.8 | 4189.3 | 5.11 |
| 19 | 2 | [Glu$^3$, Lys$^{10}$, Arg$^{30}$, Glu$^{33}$] GLP-2 | ε-Lys10 | γ-Glu | N—C16oyl(Glu) | 35.4 | 6.3 | 4187.4 | 4187.2 | 10.08 |
| 20 | 2 | [Glu$^3$, Lys$^{11}$, Arg$^{30}$, Glu$^{33}$] GLP-2 | ε-Lys11 | γ-Glu | N—C16oyl(Glu) | 37.2 | 6.6 | 4204.2 | 4203.8 | 35.50 |
| 21 | 2 | [Glu$^3$, Lys$^{12}$, Arg$^{30}$, Glu$^{33}$] GLP-2 | ε-Lys12 | γ-Glu | N—C16oyl(Glu) | 35.9 | 6.8 | 4216.2 | 4217.3 | 43.05 |
| 22 | 2 | [Glu$^3$, Lys$^{13}$, Arg$^{30}$, Glu$^{33}$] GLP-2 | ε-Lys13 | γ-Glu | N—C16oyl(Glu) | 35.6 | 6.3 | 4205.4 | 4205.2 | 1.56 |
| 23 | 2 | [Glu$^3$, Lys$^{14}$, Arg$^{30}$, Glu$^{33}$] GLP-2 | ε-Lys14 | γ-Glu | N—C16oyl(Glu) | 35.0 | 6.4 | 4205.4 | 4205.2 | 5.51 |
| 24 | 2 | [Glu$^3$, Lys$^{15}$, Arg$^{30}$, Glu$^{33}$] GLP-2 | ε-Lys15 | γ-Glu | N—C16oyl(Glu) | 36.1 | 6.4 | 4204.2 | 4203.3 | 6.06 |
| 25 | 2 | [Glu$^3$, Lys$^{16}$, Arg$^{30}$, Glu$^{33}$] GLP-2 | ε-Lys16 | γ-Glu | N—C16oyl(Glu) | 36.0 | 6.4 | 4204.2 | 4204.3 | 2.28 |
| 2 | 2 | [Glu$^3$, Lys$^{17}$, Arg$^{30}$, Glu$^{33}$] GLP-2 | ε-Lys17 | γ-Glu | N—C16oyl(Glu) | 35.8 | 6.1 | 4204.4 | 4204.8 | 29.30 |
| 26 | 2 | [Glu$^3$, Lys$^{18}$, Arg$^{30}$, Glu$^{33}$] GLP-2 | ε-Lys18 | γ-Glu | N—C16oyl(Glu) | 35.7 | 6.3 | 4247.4 | 4247.3 | 6.51 |
| 27 | 2 | [Glu$^3$, Lys$^{19}$, Arg$^{30}$, Glu$^{33}$] GLP-2 | ε-Lys19 | γ-Glu | N—C16oyl(Glu) | 35.3 | 6.2 | 4250.7 | 4247.3 | 4.36 |
| 28 | 2 | [Glu$^3$, Lys$^{20}$, Arg$^{30}$, Glu$^{33}$] GLP-2 | ε-Lys20 | γ-Glu | N—C16oyl(Glu) | 37.5 | 4.9 | 4162.8 | 4162.2 | 2.33 |
| 29 | 2 | [Glu$^3$, Lys$^{21}$, Arg$^{30}$, Glu$^{33}$] GLP-2 | ε-Lys21 | γ-Glu | N—C16oyl(Glu) | 36.3 | 6.3 | 4204.2 | 4203.3 | 8.70 |
| 30 | 2 | [Glu$^3$, Lys$^{22}$, Arg$^{30}$, Glu$^{33}$] GLP-2 | ε-Lys22 | γ-Glu | N—C16oyl(Glu) | 34.6 | 6.6 | 4170.6 | 4171.2 | 4.50 |
| 31 | 2 | [Glu$^3$, Lys$^{23}$, Arg$^{30}$, Glu$^{33}$] GLP-2 | ε-Lys23 | γ-Glu | N—C16oyl(Glu) | 35.0 | 5.9 | 4206.6 | 4205.2 | 0.82 |
| 32 | 2 | [Glu$^3$, Lys$^{24}$, Arg$^{30}$, Glu$^{33}$] GLP-2 | ε-Lys24 | γ-Glu | N—C16oyl(Glu) | 36.3 | 6.5 | 4204.2 | 4204.3 | 5.40 |
| 33 | 2 | [Glu$^3$, Lys$^{25}$, Arg$^{30}$, Glu$^{33}$] GLP-2 | ε-Lys25 | γ-Glu | N—C16oyl(Glu) | 35.7 | 5.2 | 4133.4 | 4132.2 | 2.40 |
| 34 | 2 | [Glu$^3$, Lys$^{26}$, Arg$^{30}$, Glu$^{33}$] GLP-2 | ε-Lys26 | γ-Glu | N—C16oyl(Glu) | 34.7 | 6.0 | 4206.6 | 4205.2 | 21.00 |
| 35 | 2 | [Glu$^3$, Lys$^{27}$, Arg$^{30}$, Glu$^{33}$] GLP-2 | ε-Lys27 | γ-Glu | N—C16oyl(Glu) | 35.8 | 6.1 | 4205.4 | 4205.2 | 6.87 |
| 36 | 2 | [Glu$^3$, Lys$^{28}$, Arg$^{30}$, Glu$^{33}$] GLP-2 | ε-Lys28 | γ-Glu | N—C16oyl(Glu) | 36.7 | 6.3 | 4189.8 | 4190.3 | 17.20 |
| 37 | 2 | [Glu$^3$, Lys$^{29}$, Arg$^{30}$, Glu$^{33}$] GLP-2 | ε-Lys29 | γ-Glu | N—C16oyl(Glu) | 36.4 | 6.5 | 4216.2 | 4217.3 | 4.26 |
| 38 | 2 | [Glu$^3$, Lys$^{30}$, Glu$^{33}$] GLP-2 | ε-Lys30 | γ-Glu | N—C16oyl(Glu) | 38.1 | 5.3 | 4162.8 | 4162.2 | 12.69 |
| 39 | 2 | [Glu$^3$, Arg$^{30}$, Lys$^{31}$, Glu$^{33}$] GLP-2 | ε-Lys31 | γ-Glu | N—C16oyl(Glu) | 36.0 | 6.5 | 4204.2 | 4205.2 | 2.85 |
| 40 | 2 | [Glu$^3$, Arg$^{30}$, Lys$^{32}$, Glu$^{33}$] GLP-2 | ε-Lys32 | γ-Glu | N—C16oyl(Glu) | 36.7 | 6.3 | 4216.2 | 4217.2 | 8.23 |
| 41 | 2 | [Glu$^3$, Arg$^{30}$, Lys$^{33}$] GLP-2 | ε-Lys33 | γ-Glu | N—C16oyl(Glu) | 36.9 | 6.6 | 4188.6 | 4189.3 | 2.08 |
| 3 | 2 | [Glu$^3$, Arg$^{30}$, Glu$^{33}$, Lys$^{34}$] GLP-2 | ε-Lys34 | γ-Glu | N—C16oyl(Glu) | 36.7 | 6.6 | 4319.4 | 4318.4 | 1.30 |
| 42 | 2 | [Glu$^3$, Lys$^{17}$, Arg$^{30}$, Glu$^{33}$] GLP-2 | ε-Lys17 | γ-Glu | N—C14oyl(Glu) | 33.5 | 4.7 | 4177.8 | 4177.8 | 2.05 |
| 43 | 2 | [Glu$^3$, Lys$^{17}$, Arg$^{30}$, Glu$^{33}$] GLP-2 | ε-Lys17 | γ-Glu | N—C12oyl(Glu) | 31.9 | 4.4 | 4149.0 | 4148.8 | 8.17 |

TABLE 2-continued

HPLC and mass spectrometry characterisation of synthesized GLP-2 derivatives. HPLC, rt (mn): retention time in minutes in the analytical RP-HPLC system (see methods). LS-MS, rt (mn): retention time in minutes in the RP-HPLC/ionspray mass spectrometry system (see methods). MW: Molecular weight.

| Example and compound number | Prepared as in ex. | Peptide | Acyl-site | Spacer | Fatty acid | HPLC, rt (mn) | LC-MS, rt (mn) | Found MW | Calc. MW | Amount (mg) |
|---|---|---|---|---|---|---|---|---|---|---|
| 5 | | [Glu$^3$, Lys$^{17}$, Arg$^{30}$, Glu$^{33}$] GLP-2 | ε-Lys17 | β-Ala | N—C16oyl(βAla) | 36.0 | 4.7 | 4146.6 | 4147.6 | 2.80 |
| 44 | 5 | [Glu$^3$, Lys$^{17}$, Arg$^{30}$, Glu$^{33}$] GLP-2 | ε-Lys17 | β-Ala | N—C14oyl(βAla) | 34.0 | 4.3 | 4119.6 | 4119.7 | 1.19 |
| 45 | 5 | [Glu$^3$, Lys$^{17}$, Arg$^{30}$, Glu$^{33}$] GLP-2 | ε-Lys17 | β-Ala | N—C12oyl(βAla) | 32.2 | 4.3 | 4091.4 | 4091.6 | 0.87 |
| 6 | | [Glu$^3$, Lys$^{17}$, Arg$^{30}$, Glu$^{33}$] GLP-2 | ε-Lys17 | none | N—C16oyl | 36.9 | 5.1 | 4076.4 | 4076.1 | 2.63 |
| 46 | 6 | [Glu$^3$, Lys$^{17}$, Arg$^{30}$, Glu$^{33}$] GLP-2 | ε-Lys17 | none | N—C14oyl | 34.7 | 4.7 | 4049.4 | 4047.7 | 1.63 |
| 47 | 6 | [Glu$^3$, Lys$^{17}$, Arg$^{30}$, Glu$^{33}$] GLP-2 | ε-Lys17 | none | N—C12oyl | 32.9 | 4.4 | 4020.4 | 4019.7 | 4.25 |
| 4 | | [Glu$^3$, Lys$^{17}$, Arg$^{30}$, Glu$^{33}$] GLP-2 | ε-Lys17 | GABA | N—C16oyl(GABA) | 36.5 | 4.9 | 4161.0 | 4161.2 | 1.96 |
| 48 | 4 | [Glu$^3$, Lys$^{17}$, Arg$^{30}$, Glu$^{33}$] GLP-2 | ε-Lys17 | GABA | N—C14oyl(GABA) | 34.3 | 4.5 | 4133.4 | 4132.8 | 6.04 |
| 49 | 4 | [Glu$^3$, Lys$^{17}$, Arg$^{30}$, Glu$^{33}$] GLP-2 | ε-Lys17 | GABA | N—C12oyl(GABA) | 32.5 | 4.3 | 4104.6 | 4104.8 | 1.87 |
| 50 | 7 | [Glu$^3$, Lys$^{17}$, Arg$^{30}$, Glu$^{33}$] GLP-2 | ε-Lys17 | none | N-Lithocholoyl | 32.7 | 4.5 | 4196.0 | 4195.8 | 1.41 |
| 7 | | [Glu$^3$, Lys$^{17}$, Arg$^{30}$, Glu$^{33}$] GLP-2 | ε-Lys17 | none | N-Choloyl | 30.0 | 4.2 | 4228.2 | 4227.8 | 2.18 |
| 51 | 4 | [Glu$^3$, Lys$^{17}$, Arg$^{30}$, Glu$^{33}$] GLP-2 | ε-Lys17 | GABA | N-4-pentylbenzoyl(GABA) | 31.1 | 4.2 | 4097.4 | 4096.6 | 7.97 |
| 52 | 4 | [Glu$^3$, Lys$^{14}$, Arg$^{30}$, Glu$^{33}$] GLP-2 | ε-Lys14 | GABA | N—C12oyl(GABA) | 33.1 | 4.4 | 4104.6 | 4104.8 | 1.25 |
| 53 | 5 | [Glu$^3$, Lys$^{14}$, Arg$^{30}$, Glu$^{33}$] GLP-2 | ε-Lys14 | β-Ala | N—C12oyl(βAla) | 31.8 | 4.3 | 4092.0 | 4091.4 | 6.01 |
| 54 | 4 | [Glu$^3$, Lys$^{13}$, Arg$^{30}$, Glu$^{33}$] GLP-2 | ε-Lys13 | GABA | N—C12oyl(βAla) | 32.0 | 4.5 | 4105.8 | 4104.8 | 22.16 |
| 55 | 5 | [Glu$^3$, Lys$^{13}$, Arg$^{30}$, Glu$^{33}$] GLP-2 | ε-Lys13 | β-Ala | N—C12oyl(βAla) | 32.0 | 4.4 | 4090.4 | 4091.4 | 1.32 |
| 56 | 4 | [Glu$^3$, Lys$^{10}$, Arg$^{30}$, Glu$^{33}$] GLP-2 | ε-Lys10 | GABA | N—C12oyl(βAla) | 32.3 | 4.5 | 4087.6 | 4086.8 | 26.18 |
| 57 | 5 | [Glu$^3$, Lys$^{10}$, Arg$^{30}$, Glu$^{33}$] GLP-2 | ε-Lys10 | β-Ala | N—C12oyl(βAla) | 32.0 | 4.5 | 4073.4 | 4073.6 | 30.53 |
| 58 | 5 | [Glu$^3$, Leu$^{10}$, Lys$^{17}$, Arg$^{30}$, Glu$^{33}$] GLP-2 | ε-Lys17 | β-Ala | N—C14oyl(βAla) | 34.5 | 4.7 | 4101.6 | 4101.7 | 19.78 |

Example 2

Building Block Synthesis:

Building Block 1 Eicosanedioic Acid Mono-Tert-Butyl Ester:

To eicosanedioic acid (3 g, 8.76 mmol) was added toluene (25 mL) and N,N dimethylformamide di-tert-butylacetal (2.1 mL, 8.76 mmol). The mixture is heated to 95° C. for 30 minutes, the mixtures is filtered and evaporated to an oil, which is redisolved in dichloromethane and washed with

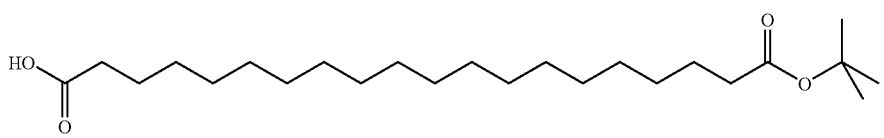

water. The organic phase is dried and evaporated to give 722 mg (21%) of the title compound, which was subsequently used without any further purification.

$^1$H NMR (CDCl$_3$): δ 10.90 (br s, 1H), 2.35 (t, 2H), 20 (t, 2H), 1.60 (m, 4H), 1.45 (s, 9H); 1.40-1.20 (m, 28H)

Synthesis of L17K(3-(ω-caboxypentadecanoy-lamino)propionyl)K30R/D33E-GLP-2(1-33)

59.a Synthesis of the Protected Peptidyl Resin:

The protected peptidyl resin was synthesized according to the Fmoc strategy on an Applied Biosystems 431A peptide synthesizer in 0.25 mmol scale using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP (N-methyl pyrrolidone), and UV monitoring of the deprotection of the Fmoc protection group. The starting resin (400 mg) used for the synthesis was (4-((2',4'-dimethoxyphenyl)-(Fmoc-Glu(OBut)-O-p-Benzyloxybenzyl resin (Wang resin) (Novabiochem, Bad Soden, Germany. cat. #: 04-12-2052) with a substitution capacity of 0.53 mmol/g.

The protected aminoacid derivatives used were Fmoc-Ala-OH, Fmoc-Arg(Pmc)-OH, Fmoc-Asn(Trt)-OH, Fmoc-Asp(OBut)-OH, Boc-His(Boc)-OH, Fmoc-Gln(Trt)-OH, Fmoc-Glu(OBut)-OH, Fmoc-(FmocHmb)Gly-OH, Fmoc-Ile-OH, Fmoc-Leu-OH, Fmoc-Lys(DDE)-OH, Fmoc-Met-OH, Fmoc-Phe-OH, Fmoc-Ser(But)-OH, Fmoc-Thr(But)-OH, Fmoc-Trp(Boc)-OH.

59.b Dde Removal and Acylation

To the protected peptidyl resin resulting from (59.a) (300 mg, 75 μmol) is added a freshly prepared solution of hydrazine hydrate 2% in NMP (12 ml). The reaction mixture is shaken for 3 minuntes at room temperature, and then filtered. More hydrazine solution (20 ml) is added on the reaction mixture is shaken for 15 minutes and then filtered. The resin is then washed extensively with NMP (5×20 mL).

Fmoc-beta-alanine (93 mg, 0.30 mmol), 3-hydroxy-1,2,3-benzotriazin-4(3H)-one (49 mg, 0.30 mmol) and diisopropylethylamine (13 μL, 0.075 mmol) was dissolved in NMP (20 mL) and added to the Dde deprotected resin, N,N'-diisopropylcarbodiimide (46 μL, 0.3 mmol) was added and the mixture was shaken overnight. The resin was filtered and washed with NMP (5×20 mL). The resin was treated with piperidine (20% in NMP, 20 mL) for 10 minutes followed by another treatment of piperidine (20% in NMP, 20 mL) for 10 minutes. The resin was filtered and washed with NMP. (5×20 mL).

Hexadecanedioic acid mono-(2,5-dioxopyrrolidin-1-yl) ester (Ebashi et al. EP511600) (107 mg, 0.3 mmol) was dissolved in NMP (20 mL), added to the resin and shaken overnight at room temperature. The reaction mixture is filtered and the resin is washed extensively with NMP, dichloromethane, 2-propanol, methanol and diethyl ether.

2.c Cleavage of the Acylated Peptide from the Resin:

The peptide is cleaved from the protected peptidyl resin by stirring with a mixture of TFA (trifluoro acetic acid) (20 ml), triisopropylsilane (500 μl) and water (500 μl) for 60 min at room temperature. The cleavage mixture is filtered and the filtrate is concentrated to approximately 2 ml by a stream of nitrogen. The crude peptide is precipitated from this oil with diethyl ether (10 ml), washed 3 times with diethyl ether (3 times 10 ml) and dried to a white powder.

2.d Purification of the Peptide:

The crude peptide is dissolved in water/acetonitrile (65:35) adjusted to pH 7.5 with NH$_4$OH and purified by preparative HPLC (Waters, Prep LC2000) on a 25 mm×250 mm column packed with C-18 silica. The column is eluted with a gradient of 43 to 60% acetonitrile against 0.1% TFA/water at 10 ml/min at room temperature for 40 minutes. The peptide containing fractions are collected, diluted with 3 volumes of water and lyophilized, yield determined by dry weight 21 mg.

The final product obtained is characterized by RP-HPLC/ion spray mass spectrometry (LC-MS) (retention time and molecular mass)

The LC-MS analysis is performed using a Symmetry 3.0 mm×150 mm 5 μl C-18 silica column (Waters, Milford Mass., USA) which is eluted at 1 ml/min at room temperature. It is equilibrated with 5% CH$_3$CN/0.1% TFA/H$_2$O and eluted by a gradient of 5% CH$_3$CN/0.1% TFA/H$_2$O to 90% CH$_3$CN/0.1% TFA/H$_2$O during 10 min. Besides the UV detection at 214 nm, a fraction of the column eluate is introduced into the ionspray interface of a PE-Sciex API 100 mass spectrometer. The mass range 300-2000 amu is scanned every 2 seconds during the run.

Using these conditions, the retention time of the product as determined from the UV trace is found to be 3.84 min, and the molecular masspeaks identified were 1042.1 (m/4) and 1388.6 (m/3) which is in agreement with the expected structure within the experimental error of the method (±1 amu).

Example 60

Synthesis of L17K(3-(ω-caboxynonadecanoylamino) propionyl)K30R/D33E-GLP-2(1-33)

The protected peptidyl resin (100 mg, 25 μmol) was synthesized according to the Fmoc strategy as in example (59.a), Dde deprotected and acylated with Fmoc-beta-alanine followed by removal of the Fmoc group was done as described in 59.b. The acylation with eicosanedioic acid mono-tert-butyl ester was done as follows. Eicosanedioic acid mono-tert-butyl ester (40 mg, 0.1 mmol), 3-hydroxy-1,2,3-benzotriazin-4(3H)-one (16 mg, 0.1 mmol) and diisopropylethylamine (4 μL, 0.025 mmol) was dissolved in NMP (2 mL) and added to the Fmoc deprotected resin, N,N'-diisopropylcarbodiimide (15 μL, 0.1 mmol) was added and the mixture was shaken overnight.

Cleavage from the resin and purification were done according to (59.c and 59.d).

The final product obtained is characterized by RP-HPLC/ion spray mass spectrometry (LC-MS) (retention time and molecular mass) and by analytical RP-HPLC (retention time and peptide amount). The peptide amount is calculated by comparing the UV detector response with that of a GLP-2 standard where the amount had been determined by amino acid analysis. The RP-HPLC analysis is performed on a Vydac 218TP54 4.6 mm×250 mm 5μ C-18 silica column (The Separations Group, Hesperia) with UV detection at 214 nm. The column is equilibrated with 0.1% TFA/H$_2$O and eluted by a gradient of 0 to 90% CH$_3$CN against 0.1% TFA/water for 50 min at 42° C., with a flow of 0.5 ml/mn. The retention time is found to be 35.0 min, and the peptide yield to be 100 μg.

By LC-MS analysis of the product was done at the same conditions as described in 59.d, a retention time of 4.25 min was found from the UV trace, and the molecular masspeaks identified were 1055.1 (m/4) and 1407.6 (m/3) which is in agreement with the expected structure

Example 61

Preparation of GLP-2 Peptide Analogs by Recombinant Technology in Yeast.

The Yeast Expression System

The host strain, which has been used to express GLP-2 precursors is a polyploid strain designated ME1719. ME1719 has phenotypes which lack two aspartyl proteases, i.e., (1) yapsin 1 (previously called YAP3p) which cleaves C-terminal side of mono- or dibasic amino acid residues (Egel-Mitani, M, Flygenring, H. A. & Hansen, M. T., YEAST 6:127-137, 1990) and (2) vacuolar protease A (Pra1p) responsible for activation of other proteases such as protease B, carboxypeptidase Y, aminopeptidase 1, RNase, alkaline phosphatase, acid trehalase and exopolyphosphatase. ME1719 can stably produce small peptides in high yield, which contain mono- or dibasic amino acids. Among other peptides, such as glucagon and GLP-1, GLP-2 is the most advantageous to use this yeast strain (Egel-Mitani, M., Brandt, J. and Vad, K.: Method for the production of polypeptides is described in U.S. Pat. No. 6,110,703, 29 Aug. 2000 and Egel-Mitani, M., Anderson, A. S., Diers, I, Hach, M., Thim, L., Hastrup, S. and Vad, K.: Enzyme and Microbial Technology 26:671-677, 2000). Moreover, the triosephosphate isomerase gene (TPI1) has been disrupted in this strain, which phenotype makes it possible to utilise glucose as a selection marker of yeast transformants, which enable to obtain high biomass, hitherto high yield in continuous fermentation.

In order to express human GLP-2 in yeast, *S. cerevisiae*, in which human amino acid sequence has been obtained from EMBL (VO1515 HSGLUC), yeast codon usage has been introduced to optimize GLP-2 production. In the present example data for four GLP-2 peptide analog expression plasmids are included; 1) A2G-GLP-2(1-33), 2) M10K/K30R-GLP-2(1-33), 3) M10L/L17K/K30R-GLP-2(1-33), 4) L17K/K30R-GLP-2(1-33).

Figure 7:
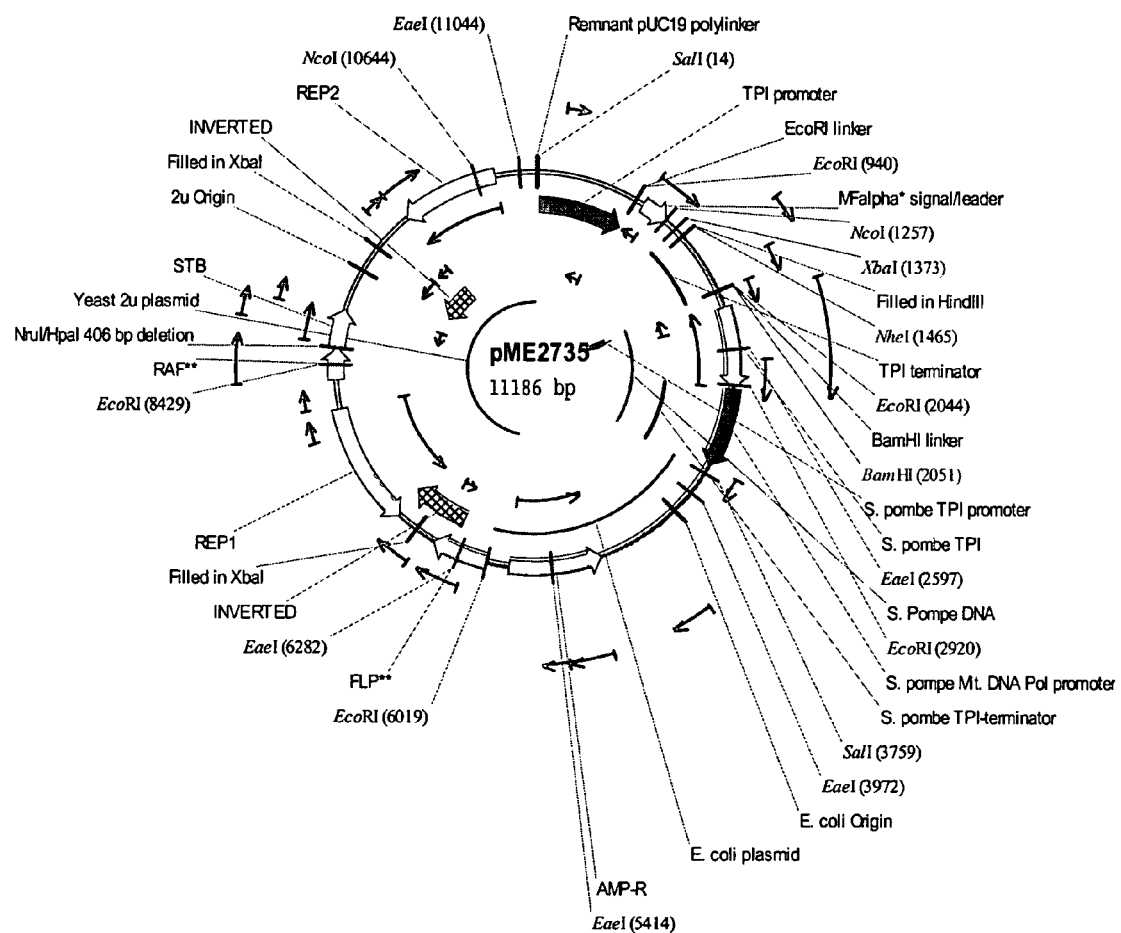
FIG. 7 S. cerevisiae plasmid for the expression and secretion of GLP-2 peptide analogs.

DNA and amino acid mutations were made according to the wild-type human amino acid sequence (HADGSFS-DEMNTILDNLAARDFINWLIQTKITD) with corresponding yeast codon usage. DNA sequence of the GLP-2 peptide analogs was inserted in an expression vector (FIG. 7). As shown in FIG. 7 the GLP-2 expression is driven by TPI promoter and MFα signal-leader sequence followed by the GLP-2 coding sequence inserted between NcoI and XbaI restriction enzyme sites. Procedures for preparing a DNA construct using polymerase chain reaction using specific primers are well known to persons skilled in the art (cf. PCR Protocols, 1990, Academic Press, San Diego, Calif., USA) and may be used for the preparation of any GLP-2 peptide analog according to the invention.

Fermentation and Determination of Yields

For small-scale batch cultures, transformants were inoculated in 5 ml of YPD+$Ca^{2+}$ medium (1% yeast extract, 2% peptone, 5 mM $CaCl_2$) and cultivated with shaking (200 rpm) at 30° C. for 3 days. Culture supernatant were analysed by HPLC after cells had been spun down by centrifugation. The following HLPC method was used:

| | |
|---|---|
| Column: | C4 Jupiter, 300 Å, 5 um, 4.6 × 250 mm |
| Buffer A: | 0.10% TFA |
| Buffer B: | 0.07% TFA in $CH_3CN$ |
| Flow: | 1 ml/min |
| Gradient: | 30-60% B over 15 min. at room temperature. |

The following yields of GLP-2 peptide analogs were obtained in small-scale (5 ml) cultures in the ME1729 host strains:

| Construct | Plasmid | Yeast transformant | Yield |
|---|---|---|---|
| A2G-GLP-2(1-33) | pKV220 | YES2651 | 13.0 mg/L |
| M10K/K30R-GLP-2(1-33) | pME2794 | YES2795 | 32.8 mg/L |
| M10L/L17K/K30R-GLP-2(1-33) | pME2765 | YES2766 | 36.6 mg/L |
| L17K/K30R-GLP-2(1-33) | pME2735 | YES2736 | 33.9 mg/L |

Purification and Characterisation

All GLP-2 peptide analogs according to the present invention may be purified using the following overall purification scheme:

| No | Step | Overall Yield |
|---|---|---|
| 1 | Fermentation liquid ▼ | 100% |
| 2 | Capture Column ▼ | 75% |
| 3 | Precipitation ▼ | 71% |
| 4 | Hydroxyapatite Column ▼ | 60% |
| 5 | Source30Q Column ▼ | 53% |
| 6 | RP-HPLC Column ▼ | 45% |
| 7 | Precipitation | 43% |

The purified peptides were analysed by amino acid sequence analysis and mass spectrometry. N-terminal amino acid sequences were determined by automated Edman degradations using an Applied Biosystem Model 494 Protein Sequencer essentially as described by the manufacturer. By using an optimised system it was possible to determine the partial sequence of as little as 300-500 fmol of peptide.

Mass spectrometric analysis was performed on a Voyager RP MALDI-TOF instrument (Perseptive Biosystems Inc., Framingham, Mass.) equipped with a nitrogen laser (337 nm). The instrument was operated in linear mode with delayed extraction, and the accelerating voltage in the ion source was 25 kV.

Sample preparation was done as follows: 1 µl sample-solution was mixed with 1 µl matrix-solution (alpha-cyano-4-hydroxy-cinnamic acid dissolved in a 5:4:1 (v/v/v) mixture of acetonitrile:water:3%(v/v) TFA) and 1 µl was deposited on the sample plate and allowed to dry. Calibration was performed using external standards and the accuracy of the mass determinations was within 0.1%.

| Peptide | Found MW | Calculated MW |
|---|---|---|
| Native GLP-2 | 3767 | 3766.2 |
| A2G-GLP-2(1-33) | 3751 | 3752.1 |
| M10K/K30R-GLP-2(1-33) | 3793 | 3805.2 |
| M10L/L17K/K30R-GLP-2(1-33) | 3793 | 3791.2 |
| L17K/K30R-GLP-2(1-33) | 3809 | 3809.2 |

Preparation of GLP-2 Derivatives from GLP-2 Peptides Prepared by Recombinant Technology in Yeast.

The following general procedure was used for the acylation of GLP-2 peptides prepared by recombinant technology in yeast:

50 mg of lyophilised peptide was dissolved in 3.2 ml of water at 4° C. The pH was adjusted to 12.2 with 1 M of NaOH. The solution was allowed to stand for 2 min at 10° C. and the pH was adjusted to 9.5 with 1M HAc. 7 ml of 4° C. cold N-Methyl-2-pyrrolidone (NMP) was added and the temperature adjusted to 10° C. The pH was adjusted to 11.5 with triethylamine. The acylation reagent (e.g. Pal-β-Ala-ONSu) was dissolved in NMP to a concentration of 20 mg/ml. A volume of 0.78 ml of this solution was added to the peptide solution and the acylation reaction was allowed to continue for 15 min at 15° C. under stirring. The reaction was stopped by the addition of 0.65 ml of a 100 mg/ml glycine solution and the pH was adjusted to 8.5 with 5M of HAc. The acylated GLP-2 peptide analog was purified by RP-HPLC. Examples of different acylation reagents that may be used according to this example inludes but are not limited to:

Lau-Glu(ONSu)-OBu$^t$: $N^\alpha$-Dodecanoyl-L-glutamic acid α-t-butyl ester γ-2,5-dioxopyrrolidin-1-yl ester.

Pal-Glu(ONSu)-OBu$^t$: $N^\alpha$-Hexadecanoyl-(L)-glutamic acid α-t-butyl-γ-2,5-dioxopyrrolidin-1-yl diester.

Lau-β-Ala-ONSu: $N^\beta$-Dodecanoyl-β-alanine 2,5-dioxopyrrolidin-1-yl ester.

Myr-β-Ala-ONSu: $N^\beta$-Tetradecanoyl-β-alanine 2,5-dioxopyrrolidin-1-yl ester.

Pal-β-Ala-ONSu: $N^\beta$-Hexadecanoyl-β-alanine 2,5-dioxopyrrolidin-1-yl ester.

Lau-GABA-ONSu: $N^\gamma$-Dodecanoyl-γ-aminobutyric acid 2,5-dioxopyrrolidin-1-yl ester.

Myr-GABA-ONSu: $N^\gamma$-Tetradecanoyl-γ-aminobutyric acid 2,5-dioxopyrrolidin-1-yl ester.

Pal-GABA-ONSu: $N^\gamma$-Hexadecanoyl-γ-aminobutyric acid 2,5-dioxopyrrolidin-1-yl ester.

Ste-GABA-ONSu: $N^\gamma$-Octadecanoyl-γ-aminobutyric acid 2,5-dioxopyrrolidin-1-yl ester.

Purification and Characterisation of Acylated GLP-2 Peptide Analogs (GLP-2 Derivatives):

The acylated analogs were purified using the following overall scheme:

|   | Step | Overall yield |
|---|------|---------------|
| 1 | GLP-2 peptide analog peptide | 100% |
| 2 | Acylation | 77% |
| 3 | RP-HPLC Column | 63% |
| 4 | Precipitation | 58% |
| 5 | Solubilization and freeze-drying | 51% |

The acylated analogs were characterised by mass spectrometry analysis as described.

Example 62

Bioassay in Mice. Dose-Response Study of GLP-2 Derivatives.

Table 3. Model parameter estimates following nonlinear regression analysis of dose and small intestinal weights relative to body weight.

Table 4. Model parameter estimates following nonlinear regression analysis of dose and small intestinal weights.

Table 5. Body weight, small intestinal weight and relative small intestinal weight of mice treated with L17K(3-(tetradecanoylamino)propionyl)/K30R-GLP-2(1-33).

Table 6. Body weight, small intestinal weight and relative small intestinal weight of mice treated with L17K(3-(hexadecanoylamino)propionyl)/K30R-GLP-2(1-33).

Table 7. Body weight, small intestinal weight and relative small intestinal weight of mice treated with A2G-GLP-2 (1-33).

Table 8. Body weight, small intestinal weight and relative small intestinal weight of control mice.

GLP-2 derivatives are being developed for the treatment of people with a number of gastrointestinal diseases including small bowel syndrome.

The objective of the present study is to establish the dose-response relationship of the GLP-2 derivative-induced growth of the small intestine in mice using derivatives L17K (3-(tetradecanoylamino)propionyl)/K30R-GLP-2(1-33), L17K(3-(hexadecanoylamino)propionyl)/K30R-GLP-2(1-33), and A2G-GLP-2(1-33) in 7 daily, subcutaneous doses for 10 days.

The following GLP-2 derivatives and analog were tested:
1. L17K(3-(tetradecanoylamino)propionyl)/K30R-GLP-2 (1-33).
2. L17K(3-(hexadecanoylamino)propionyl)/K30R-GLP-2 (1-33).
3. A2G-GLP-2(1-33).

All derivatives were dissolved and diluted in buffer containing:

Disodiumhydrogenphosphate 1.42 mg/ml, Mannitol 36.9 mg/ml, Phenol 5 mg/ml, pH 8.0.

189 female C57b1 mice were used in the study. All animals were divided into four groups:

Group 1: Controls
Group 2: L17K(3-(tetradecanoylamino)propionyl)/K30R-GLP-2(1-33)
Group 3: L17K(3-(hexadecanoylamino)propionyl)/K30R-GLP-2(1-33)
Group 4: A2G-GLP-2(1-33)

Dosing

All animals received a daily subcutaneous injection of 100 pi for 10 days with the following doses:

| | | Dose - μg | | | | | | |
|---|---|---|---|---|---|---|---|---|
| Group | Treatment | A | B | C | D | E | F | G |
| 1 | Control | Saline | | | | | | |
| 2 | L17K(3-(tetradecanoylamino)propionyl)/K30R-GLP-2(1-33) | 22 | 11 | 5.5 | 2.75 | 1.375 | 0.678 | 0.344 |

-continued

| | | Dose - μg | | | | | | |
|---|---|---|---|---|---|---|---|---|
| Group | Treatment | A | B | C | D | E | F | G |
| 3 | L17K(3-(hexadecanoylamino)propionyl)/K30R-GLP-2(1-33) | 35 | 17.5 | 8.75 | 4.375 | 2.188 | 1.094 | 0.547 |
| 4 | A2G-GLP-2(1-33) | 33 | 16.5 | 8.25 | 4.125 | 2.063 | 1.031 | 0.512 |

Samples

At Day 10 the animals were weighted before they were sacrificed. The intestine was carefully removed from each animal and the small intestine dissected, rinsed with saline and weighted.

Data Analysis

Body weight, small intestinal weight and small intestinal weight relative to body weight were reported for all animals and used generating the dose-response relationship. The treatment-induced increase in both absolute and relative small intestinal weight is calculated for each treatment group, since this is considered the pharmacologically relevant efficacy parameter.

A generalised Michaelis-Menten model, with shape factor γ corresponding to the Hillslope in the semilogarithmic dose-response curve and $E_0$ representing the background efficacy level at D=0, was used as dose-response model. $E_{max}$ is the maximal effect observed and $ED_{50}$ is the dose that gives an effect equal to 50% of $E_{max}$. The model was used because of the higher flexibility compared to a four parameter logistic dose-response model (1). The model was fitted to data using nonlinear regression in order to determine estimates for $E_{max}$, $ED_{50}$, γ and $E_0$.

$$E = \frac{E_{max} \cdot D^\gamma}{ED_{50}^\gamma + D^\gamma} + E_0$$

The goodness of fit was evaluated by visual inspection of plots showing observed data points together with fitted curves and residuals plots. Parameter estimates are presented together with CV % and 95% C.I.

In order to account for the variability in the background efficacy level, control data were included in the nonlinear regression analysis as D=0 for all three treatment groups.

The nonlinear regression analyses were performed using WinNonlin Professional, version 3.1, Pharsight. The nonlinear regression was performed using the Gauss-Newton (Levenberg and Hartley) algorithm.

Results

Body weight, small intestinal weight and relative small intestinal weight are shown for all animals from each dose levels and treatment groups in tables 5-8.

The results of the nonlinear regression analysis and curve fitting of the dose-response model to small intestinal weight and relative small intestinal weight data are shown in Tables 3 and 4 and FIGS. 8-11.

Figure 8:
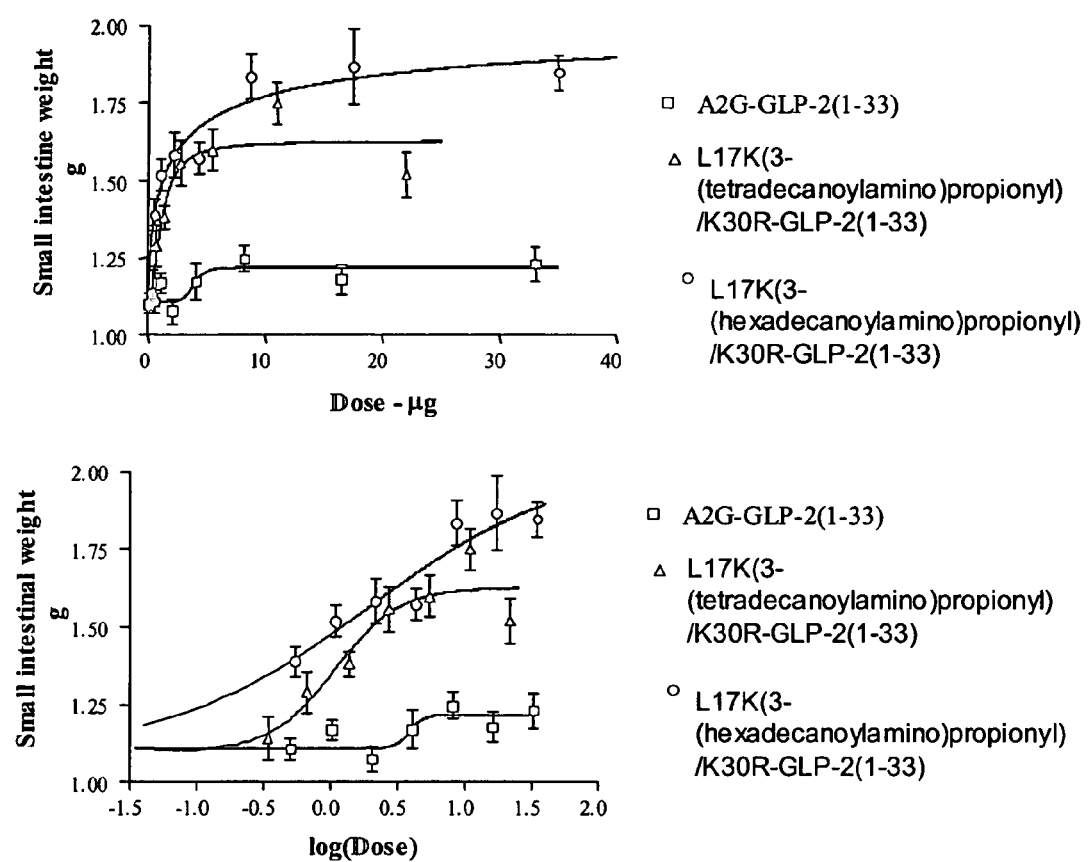
FIG. 8. Bioassay in mice. Dose-Response study of GLP-2 derivatives. Observed data points (Means±SD) and fitted curves of relative small intestinal weight data.
Figure 10:
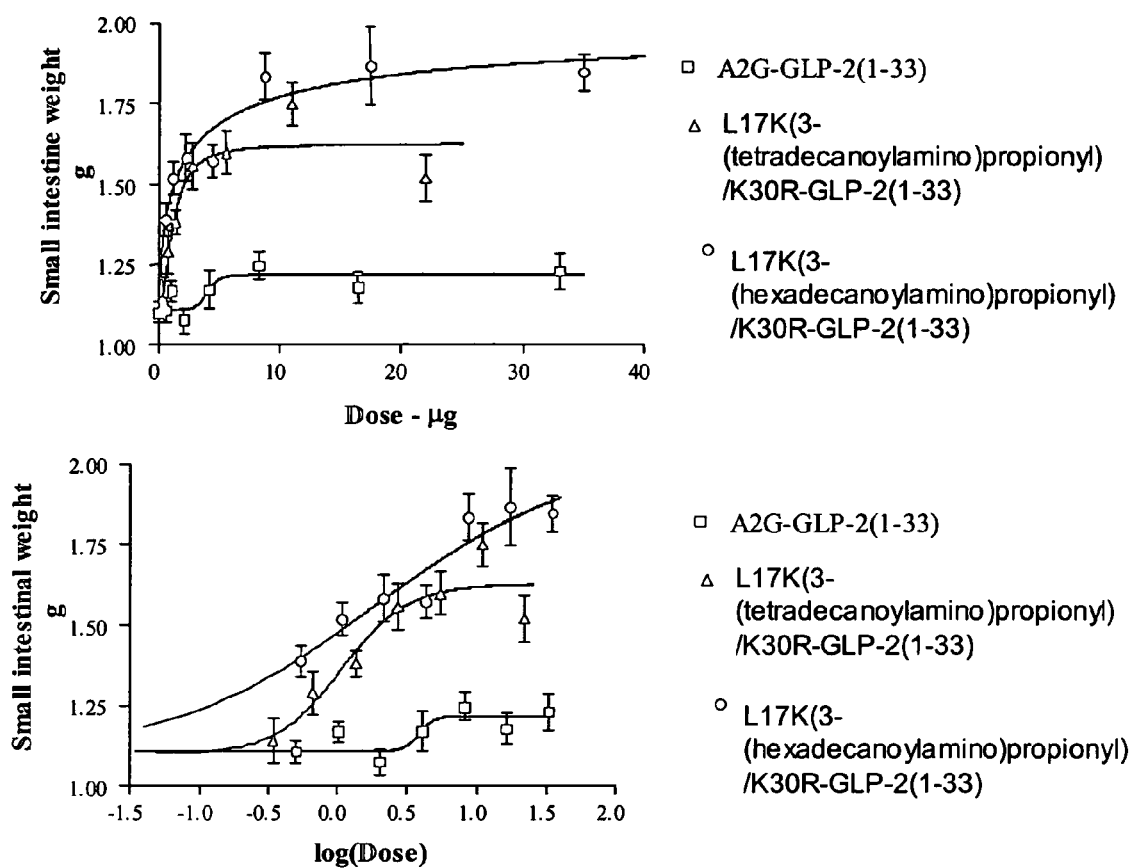
FIG. 10. Bioassay in mice. Dose-Response study of GLP-2 derivatives. Observed data points (Means±SD) and fitted curves of small intestinal weight data.
Figure 11:
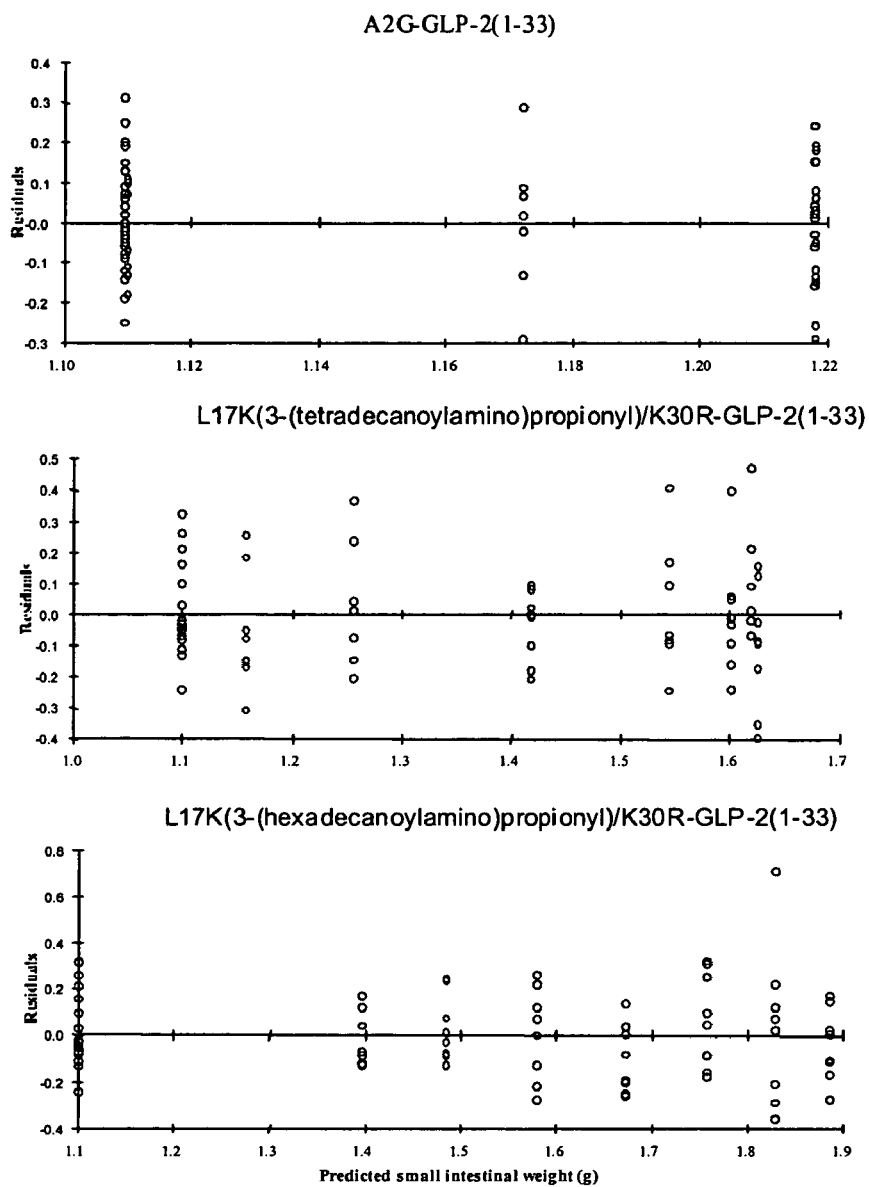
FIG. 11. Bioassay in mice. Dose-Response study of GLP-2 derivatives. Residuals of small intestinal weight data.

The dose-response relationships are visualised in FIGS. 8 and 10. Similar dose-response curves were observed for derivatives L17K(3-(tetradecanoylamino)propionyl)/K30R-GLP-2(1-33) and L17K(3-(hexadecanoylamino)propionyl)/K30R-GLP-2(1-33) when small intestinal weight and relative small intestinal weight were used as efficacy parameters. This indicates that the treatment effect on the body weights does not skew the dose-response relationship for either of the derivatives. For A2G-GLP-2(1-33) however a distinct $E_{max}$-plateau was identified when small intestinal weight was used as efficacy parameter. This was not observed for the relative small intestinal weight, indicating that the treatment could affect the body weight or that the efficacy levels could not be distinguished from background levels.

The curve fits in FIGS. 8 and 10 indicate that the model adequately can describe the dose-response relationship between both small intestinal weight and dose, and relative small intestinal weight and dose for all three compounds tested. No systematic trends appear in neither of the residual plots in FIGS. 9 and 11. Therefore no model misspecification could be observed.

The parameter estimates in Tables 3 and 4 show $E_0$ levels that are estimated with a fairly high precision (CV %<5) when both small intestinal weight and relative small intestinal weight data are examined. Higher $E_{max}$ estimates were obtained for both the L17K(3-(tetradecanoylamino)propionyl)/K30R-GLP-2(1-33) and L17K(3-(hexadecanoylamino)propionyl)/K30R-GLP-2(1-33) compared to A2G-GLP-2(1-33). The increase in $E_{max}$ compared to A2G-GLP-2(1-33) was 33% and 16% when relative small intestinal weight was used as efficacy parameter for L17K(3-(hexadecanoylamino)propionyl)/K30R-GLP-2(1-33) and L17K(3-(tetradecanoylamino)propionyl)/K30R-GLP-2(1-33) respectively and 67% and 34% when small intestinal weight was used.

The treatment-induced increase ($E_{max}$-$E_0$) in both small intestinal weight and relative small intestinal weight were determined as a secondary parameter during the curve fitting procedure. A 1.7 and 2.5 fold higher increase in relative small intestinal weight compared to A2G-GLP-2(1-33) was observed for L17K(3-(tetradecanoylamino)propionyl)/K30R-GLP-2(1-33) and L17K(3-(hexadecanoylamino)propionyl)/K30R-GLP-2(1-33) respectively. The increase when absolute small intestinal weight was measured was 4.9 and 8.6 fold higher respectively.

A relatively low precision in estimation of $ED_{50}$ was observed for A2G-GLP-2(1-33) because of the narrow interval between background level and $E_{max}$ level and, in case of the relative small intestinal weight data set, because no full dose-response curve could be obtained. This was to some extent also true for L17K(3-(hexadecanoylamino)propionyl)/K30R-GLP-2(1-33) since the lowest dose used induced an effect corresponding to 30-40% of $E_{max}$. The lack of information in the initial part of the dose-response curve would reduce the precision in estimating the $ED_{50}$ value. In general though the estimates for $ED_{50}$ obtained for L17K(3-(tetradecanoylamino)propionyl)/K30R-GLP-2(1-33) and L17K(3-(hexadecanoylamino)propionyl)/K30R-GLP-2(1-33) were comparable in size and much smaller than estimates for A2G-GLP-2(1-33). However due to the large variation in $ED_{50}$ a relative potency estimation between the tested derivatives is difficult.

In conclusion L17K(3-(hexadecanoylamino)propionyl)/K30R-GLP-2(1-33) and L17K(3-(tetradecanoylamino)propionyl)/K30R-GLP-2(1-33) induced a 67% and 34% increase in $E_{max}$ compared to A2G-GLP-2(1-33). A 8-fold higher increase in small intestinal weight was induced by L17K(3-(hexadecanoylamino)propionyl)/K30R-GLP-2(1-33) compared to the one induced by A2G-GLP-2(1-33).

TABLE 3

Model parameter estimates following nonlinear regression analysis of dose and small intestinal weights relative to body weight.

| Treatment | A2G-GLP-2(1-33) | L17K(3-(tetradecanoylamino)propionyl)/K30R-GLP-2(1-33) | L17K(3-(hexadecanoylamino)propionyl)/K30R-GLP-2(1-33) |
|---|---|---|---|
| | | Parameter estimates (CV %) | |
| $E_0$ | 0.0425 (2.4) | 0.0426 (3.0) | 0.0424 (2.9) |
| $E_{max}$ | 0.0548 (33.3) | 0.0636 (2.2) | 0.0727 (5.4) |
| $ED_{50}$ (µg) | 15.04 (470) | 1.00 (18.5) | 0.90 (41.3) |
| $E_{max} - E_0$ | 0.0123 (151) | 0.0211 (9.3) | 0.0303 (13.7) |
| $\gamma$ | 0.6625 (109) | 2.0485 (32.2) | 0.7249 (41.2) |
| | | 95% Confidence Intervals | |
| $E_0$ | 0.0405-0.0446 | 0.0400-0.0451 | 0.0399-0.0449 |
| $E_{max}$ | 0.0184-0.0912 | 0.0609-0.0663 | 0.0649-0.0805 |
| $ED_{50}$ | 0-156.17 | 0.63-1.37 | 0.16-1.65 |
| $E_{max} - E_0$ | −0.0278-0.0503 | 0.0234-0.0296 | 0.0256-0.0407 |
| $\gamma$ | −0.7761-2.1012 | 0.7336-3.3633 | 0.1284-1.3214 |

TABLE 4

Model parameter estimates following nonlinear regression analysis of dose and small intestinal weights.

| Treatment | A2G-GLP-2(1-33) | L17K(3-(tetradecanoylamino)propionyl)/K30R-GLP-2(1-33) | L17K(3-(hexadecanoylamino)propionyl)/K30R-GLP-2(1-33) |
|---|---|---|---|
| | | Parameter estimates (CV %) | |
| $E_0$ (g) | 1.1095 (2.0) | 1.0993 (3.5) | 1.1008 (3.8) |
| $E_{max}$ (g) | 1.2180 (2.3) | 1.6270 (2.9) | 2.0310 (13.1) |
| $ED_{50}$ (µg) | 3.98 (70.9) | 1.09 (25.0) | 1.99 (111) |
| $E_{max} - E_0$ (g) | 0.1085 (34.8) | 0.5278 (12.3) | 0.9302 (29.3) |
| $\gamma$ | 8.4169 (1869) | 1.8184 (38.9) | 0.5889 (52.9) |
| | | 95% Confidence Intervals | |
| $E_0$ (g) | 1.0661-1.1529 | 1.0219-1.1768 | 1.0175-1.1842 |
| $E_{max}$ (g) | 1.1613-1.2748 | 1.5345-1.7195 | 1.4999-2.5621 |
| $ED_{50}$ (µg) | 0-9.60 | 0.55-1.64 | 0-6.40 |
| $E_{max} - E_0$ (g) | 0.0345-0.1837 | 0.4021-0.6579 | 0.3967-1.4725 |
| $\gamma$ | −305.2302-322.0639 | 0.4085-3.2282 | −0.0320-1.2099 |

TABLE 5

Body weight, small intestinal weight and relative small intestinal weight of mice treated with L17K(3-(tetradecanoylamino)propionyl)/K30R-GLP-2(1-33).

| Dose level | Dose µg | Body weight g | Small intestinal weight g | Small intestinal weight/body weight |
|---|---|---|---|---|
| A | 22 | 25.88 | 1.45 | 0.0560 |
| | | 27.59 | 1.75 | 0.0634 |
| | | 26.57 | 1.60 | 0.0602 |
| | | 24.31 | 1.54 | 0.0633 |
| | | 24.11 | 1.27 | 0.0527 |
| | | 24.48 | 1.53 | 0.0625 |
| | | 25.25 | 1.78 | 0.0705 |
| | | 23.14 | 1.23 | 0.0532 |
| Mean ± SD | | 25.17 ± 1.45 | 1.5188 ± 0.1996 | 0.0602 ± 0.0060 |
| B | 11 | 24.04 | | |
| | | 27.14 | 1.83 | 0.0674 |
| | | 22.35 | 1.60 | 0.0716 |
| | | 29.45 | 2.09 | 0.0710 |
| | | 28.00 | 1.55 | 0.0554 |
| | | 24.29 | 1.83 | 0.0753 |
| | | 25.54 | 1.63 | 0.0638 |
| | | 26.59 | 1.71 | 0.0643 |
| Mean ± SD | | 25.93 ± 2.32 | 1.7486 ± 0.1857 | 0.0670 ± 0.0066 |
| C | 5.5 | 25.94 | 1.51 | 0.0582 |
| | | 28.15 | 2.00 | 0.0710 |
| | | 22.40 | 1.57 | 0.0701 |
| | | 21.48 | 1.44 | 0.0670 |
| | | 24.72 | 1.36 | 0.0550 |
| | | 26.11 | 1.59 | 0.0609 |
| | | 24.33 | 1.65 | 0.0678 |
| | | 30.32 | 1.66 | 0.0547 |
| Mean ± SD | | 25.43 ± 2.89 | 1.5975 ± 0.1921 | 0.0631 ± 0.0067 |
| D | 2.75 | 25.31 | 1.71 | 0.0676 |
| | | 29.88 | 1.64 | 0.0549 |
| | | 25.64 | 1.95 | 0.0761 |
| | | 22.62 | 1.48 | 0.0654 |
| | | 25.10 | 1.46 | 0.0582 |
| | | 25.34 | 1.46 | 0.0576 |
| | | 22.39 | 1.30 | 0.0581 |
| | | 25.47 | 1.45 | 0.0569 |
| Mean ± SD | | 25.22 ± 2.29 | 1.5563 ± 0.2025 | 0.0618 ± 0.0072 |
| E | 1.375 | 28.11 | 1.51 | 0.0537 |
| | | 25.84 | 1.50 | 0.0580 |
| | | 23.86 | 1.32 | 0.0553 |
| | | 24.06 | 1.42 | 0.0590 |
| | | 23.98 | 1.21 | 0.0505 |
| | | 23.49 | 1.24 | 0.0528 |
| | | 23.04 | 1.44 | 0.0625 |
| | | 24.73 | 1.41 | 0.0570 |
| Mean ± SD | | 24.64 ± 1.64 | 1.3813 ± 0.1131 | 0.0561 ± 0.0038 |
| F | 0.678 | 28.54 | 1.27 | 0.0445 |
| | | 30.18 | 1.49 | 0.0494 |
| | | 25.83 | 1.18 | 0.0457 |
| | | 27.35 | 1.62 | 0.0592 |
| | | 24.24 | 1.11 | 0.0458 |
| | | 26.81 | 1.30 | 0.0485 |
| | | 24.59 | 1.05 | 0.0427 |
| | | 24.19 | 1.30 | 0.0537 |
| Mean ± SD | | 26.47 ± 2.17 | 1.2900 ± 0.1896 | 0.0487 ± 0.0055 |
| G | 0.344 | 23.34 | 1.01 | 0.0433 |
| | | 26.30 | 1.08 | 0.0411 |
| | | 24.58 | 1.34 | 0.0545 |
| | | 25.43 | 1.11 | 0.0436 |
| | | 24.68 | 0.99 | 0.0401 |
| | | 27.69 | 1.41 | 0.0509 |
| | | 25.13 | 1.34 | 0.0533 |
| | | 22.58 | 0.85 | 0.0376 |
| Mean ± SD | | 24.97 ± 1.60 | 1.1413 ± 0.2003 | 0.0456 ± 0.0064 |

TABLE 6

Body weight, small intestinal weight and relative small intestinal weight of mice treated with L17K(3-(hexadecanoylamino)propionyl)/K30R-GLP-2(1-33).

| Dose level | Dose µg | Body weight g | Small intestinal weight g | Small intestinal weight/body weight |
|---|---|---|---|---|
| A | 35 | 29.69 | 1.89 | 0.0637 |
| | | 26.35 | 2.03 | 0.0770 |
| | | 28.34 | 1.91 | 0.0674 |
| | | 25.24 | 1.78 | 0.0705 |
| | | 26.16 | 1.61 | 0.0615 |
| | | 23.80 | 1.72 | 0.0723 |
| | | 27.05 | 2.06 | 0.0762 |
| | | 25.65 | 1.77 | 0.0690 |
| Mean ± SD | | 26.54 ± 1.84 | 1.8463 ± 0.1546 | 0.0697 ± 0.0055 |
| B | 17.5 | 29.80 | 1.90 | 0.0638 |
| | | 26.57 | 1.85 | 0.0696 |
| | | 32.71 | 2.54 | 0.0777 |
| | | 24.96 | 2.05 | 0.0821 |
| | | 24.66 | 1.54 | 0.0624 |
| | | 21.39 | 1.47 | 0.0687 |
| | | 27.99 | 1.95 | 0.0697 |
| | | 26.74 | 1.62 | 0.0606 |
| Mean ± SD | | 26.85 ± 3.44 | 1.8650 ± 0.3423 | 0.0693 ± 0.0075 |
| C | 8.75 | 23.32 | 1.58 | 0.0678 |
| | | 27.39 | 1.85 | 0.0675 |
| | | 26.51 | 2.01 | 0.0758 |
| | | 23.53 | 1.60 | 0.0680 |
| | | 26.31 | 1.67 | 0.0635 |
| | | 27.07 | 2.07 | 0.0765 |
| | | 23.64 | 2.08 | 0.0880 |
| | | 26.72 | 1.80 | 0.0674 |
| Mean ± SD | | 25.56 ± 1.74 | 1.8325 ± 0.2052 | 0.0718 ± 0.0079 |
| D | 4.375 | 25.11 | 1.47 | 0.0585 |
| | | 26.06 | 1.71 | 0.0656 |
| | | 25.00 | 1.68 | 0.0672 |
| | | 25.36 | 1.59 | 0.0627 |
| | | 23.79 | 1.41 | 0.0593 |
| | | 27.40 | 1.81 | 0.0661 |
| | | 26.31 | 1.48 | 0.0563 |
| | | 23.73 | 1.42 | 0.0598 |
| Mean ± SD | | 25.35 ± 1.25 | 1.5713 ± 0.1492 | 0.0619 ± 0.0040 |
| E | 2.188 | 24.71 | 1.36 | 0.0550 |
| | | 21.35 | 1.30 | 0.0609 |
| | | 27.79 | 1.80 | 0.0648 |
| | | 28.66 | 1.84 | 0.0642 |
| | | 25.95 | 1.45 | 0.0559 |
| | | 26.62 | 1.65 | 0.0620 |
| | | 22.40 | 1.58 | 0.0705 |
| | | 27.71 | 1.70 | 0.0613 |
| Mean ± SD | | 25.65 ± 2.64 | 1.5850 ± 0.1996 | 0.0618 ± 0.0050 |
| F | 1.094 | 22.75 | 1.36 | 0.0598 |
| | | 25.35 | 1.46 | 0.0576 |
| | | 22.99 | 1.50 | 0.0652 |
| | | 26.65 | 1.73 | 0.0649 |
| | | 25.54 | 1.41 | 0.0552 |
| | | 24.68 | 1.56 | 0.0632 |
| | | 29.29 | 1.72 | 0.0587 |
| | | 24.51 | 1.40 | 0.0571 |
| Mean ± SD | | 25.22 ± 2.09 | 1.5175 ± 0.1423 | 0.0602 ± 0.0038 |
| G | 0.547 | 24.31 | 1.28 | 0.0527 |
| | | 25.29 | 1.31 | 0.0518 |
| | | 24.00 | 1.44 | 0.0600 |
| | | 26.59 | 1.52 | 0.0572 |
| | | 24.42 | 1.27 | 0.0520 |
| | | 25.95 | 1.33 | 0.0513 |
| | | 23.65 | | |
| | | 29.00 | 1.57 | 0.0541 |
| Mean ± SD | | 25.40 ± 1.77 | 1.3886 ± 0.1313 | 0.0541 ± 0.0033 |

TABLE 7

Body weight, small intestinal weight and relative small intestinal weight of mice treated with A2G-GLP-2(1-33).

| Dose level | Dose µg | Body weight g | Small intestinal weight g | Small intestinal weight/body weight |
|---|---|---|---|---|
| A | 33 | 26.17 | 1.25 | 0.0478 |
|  |  | 27.69 | 1.30 | 0.0469 |
|  |  | 23.33 | 1.40 | 0.0600 |
|  |  | 22.35 | 1.10 | 0.0492 |
|  |  | 28.25 | 1.28 | 0.0453 |
|  |  | 22.85 | 1.17 | 0.0512 |
|  |  | 24.94 | 1.41 | 0.0565 |
|  |  | 21.40 | 0.93 | 0.0435 |
| Mean ± SD |  | 24.62 ± 2.55 | 1.2300 ± 0.1602 | 0.0501 ± 0.0057 |
| B | 16.5 | 21.72 | 0.96 | 0.0442 |
|  |  | 26.13 | 1.17 | 0.0448 |
|  |  | 25.43 | 1.37 | 0.0539 |
|  |  | 24.44 | 1.28 | 0.0524 |
|  |  | 23.80 | 1.07 | 0.0450 |
|  |  | 25.13 | 1.24 | 0.0493 |
|  |  | 23.06 | 1.25 | 0.0542 |
|  |  | 22.76 | 1.08 | 0.0475 |
| Mean ± SD |  | 24.06 ± 1.50 | 1.1775 ± 0.1337 | 0.0489 ± 0.0042 |
| C | 8.25 | 26.62 | 1.26 | 0.0473 |
|  |  | 24.63 | 1.16 | 0.0471 |
|  |  | 24.27 | 1.19 | 0.0490 |
|  |  | 28.30 | 1.37 | 0.0484 |
|  |  | 26.94 | 1.06 | 0.0393 |
|  |  | 25.12 | 1.23 | 0.0490 |
|  |  | 24.89 | 1.46 | 0.0587 |
|  |  | 25.51 | 1.24 | 0.0486 |
| Mean ± SD |  | 25.79 ± 1.38 | 1.2463 ± 0.1235 | 0.0484 ± 0.0052 |
| D | 4.125 | 26.28 | 1.15 | 0.0438 |
|  |  | 26.49 | 1.04 | 0.0393 |
|  |  | 27.19 | 1.46 | 0.0537 |
|  |  | 26.01 | 1.19 | 0.0458 |
|  |  | 28.58 | 1.24 | 0.0434 |
|  |  | 22.74 | 1.15 | 0.0506 |
|  |  | 23.49 | 0.88 | 0.0375 |
|  |  | 28.52 | 1.26 | 0.0442 |
| Mean ± SD |  | 26.16 ± 2.12 | 1.1713 ± 0.1687 | 0.0448 ± 0.0054 |
| E | 2.063 | 21.54 | 0.93 | 0.0432 |
|  |  | 21.97 | 0.98 | 0.0446 |
|  |  | 26.21 | 1.22 | 0.0465 |
|  |  | 25.39 | 1.18 | 0.0465 |
|  |  | 26.80 | 1.04 | 0.0388 |
|  |  | 26.64 | 1.21 | 0.0454 |
|  |  | 23.36 | 1.00 | 0.0428 |
|  |  | 22.25 | 1.04 | 0.0467 |
| Mean ± SD |  | 24.27 ± 2.23 | 1.0750 ± 0.1124 | 0.0443 ± 0.0027 |
| F | 1.031 | 24.10 | 1.09 | 0.0452 |
|  |  | 23.15 | 1.10 | 0.0475 |
|  |  | 26.06 | 1.18 | 0.0453 |
|  |  | 28.91 | 1.31 | 0.0453 |
|  |  | 27.15 | 1.18 | 0.0435 |
|  |  | 25.89 | 1.11 | 0.0429 |
|  |  | 23.41 | 1.30 | 0.0555 |
|  |  | 24.83 | 1.08 | 0.0435 |
| Mean ± SD |  | 25.44 ± 1.97 | 1.1688 ± 0.0923 | 0.0461 ± 0.0041 |
| G | 0.512 | 24.03 | 0.92 | 0.0383 |
|  |  | 23.21 | 1.09 | 0.0470 |
|  |  | 26.10 | 1.09 | 0.0418 |
|  |  | 28.97 | 1.24 | 0.0428 |
|  |  | 27.31 | 1.15 | 0.0421 |
|  |  | 25.90 | 1.18 | 0.0456 |
|  |  | 23.55 | 1.17 | 0.0497 |
|  |  | 24.71 | 1.02 | 0.0413 |
| Mean ± SD |  | 25.47 ± 1.99 | 1.1075 ± 0.1014 | 0.0436 ± 0.0036 |

TABLE 8

Body weight, small intestinal weight and relative small intestinal weight of control mice.

| Dose level | Dose µg | Body weight g | Small intestinal weight g | Small intestinal weight/body weight |
|---|---|---|---|---|
| Control | 0 | 24.39 | 0.99 | 0.0406 |
|  |  | 22.58 | 0.86 | 0.0381 |
|  |  | 22.76 | 1.08 | 0.0475 |
|  |  | 24.93 | 1.03 | 0.0413 |
|  |  | 25.46 | 0.99 | 0.0389 |
|  |  | 27.12 | 1.13 | 0.0417 |
|  |  | 25.34 | 1.42 | 0.0560 |
|  |  | 27.55 | 1.20 | 0.0436 |
|  |  | 27.38 | 1.02 | 0.0373 |
|  |  | 24.96 | 1.02 | 0.0409 |
|  |  | 24.77 | 1.31 | 0.0529 |
|  |  | 25.88 | 1.05 | 0.0406 |
|  |  | 28.86 | 1.08 | 0.0374 |
|  |  | 22.89 | 1.06 | 0.0463 |
|  |  | 24.57 | 1.07 | 0.0435 |
|  |  | 26.67 | 1.08 | 0.0405 |
|  |  | 31.59 | 1.26 | 0.0399 |
|  |  | 32.69 | 1.36 | 0.0416 |
|  |  | 27.28 | 1.03 | 0.0378 |
|  |  | 23.60 | 0.97 | 0.0411 |
| Mean ± SD |  | 26.06 ± 2.70 | 1.1005 ± 0.1411 | 0.0424 ± 0.0050 |

Example 63

Metabolic stability of selected GLP-2 derivatives. The degradation of GLP-2 derivatives in vivo in pigs have been studied and T½ value determined for selected GLP-2 derivatives according to the present invention (T½: Terminal plasma elimination half-life) (Table 9).

All test substances were dissolved in 20 mM phosphate buffer pH 7.4.

Female LYD crossbred pigs weighing 50-75 kg. were used. All test substances were dosed 0.5 nmol/kg. The dosing volume was approx. 1 ml per animal.

Subcutaneous injections were given at the right side of the neck approximately 7 cm from the ear and 9 cm from the middle of the neck. Injections were given with a stopper on the needle, allowing 0.5 cm of the needle to be inserted.

Blood samples were drawn from an ear vein catheter. The catheter was rinsed with heparin 50 IE/ml in physiological saline. During sampling the first ml blood drawn was discarded. Blood samples were kept on ice for no longer than 20 min. before centrifugation (4° C., 4000 rpm, 10 min). After centrifugation plasma was isolated and transferred to Micronic-tubes in duplo. The plasma samples were analysed by ELISA.

TABLE 9

| GLP-2 derivative | GLP-2 peptide | Acyl site | Acyl Substituent | Spacer | T½ in pigs (h) |
|---|---|---|---|---|---|
| | GLP-2(1-33) | None | None | None | 0.25 |
| L17K(3-(dodecanoylamino)propionyl)/K30R-GLP-2(1-33) | L17K/K30R-GLP-2(1-33) | ε-Lys-17 | C-12 | β-alanine | 8.5 |
| L17K(4-(dodecanoylamino)butanoyl)/K30R-GLP-2(1-33) | L17K/K30R-GLP-2(1-33) | ε-Lys-17 | C-12 | GABA | 2.3 |
| L17K(3-(tetradecanoylamino)propionyl)/K30R-GLP-2(1-33) | L17K/K30R-GLP-2(1-33) | ε-Lys-17 | C14 | β-alanine | 3.5 ± 1.8 |
| L17K(4-(tetradecanoylamino)butanoyl)/K30R-GLP-2(1-33) | L17K/K30R-GLP-2(1-33) | ε-Lys-17 | C14 | GABA | 4.5 ± 2.4 |
| L17K(3-(hexadecanoylamino)propionyl)/K30R-GLP-2(1-33) | L17K/K30R-GLP-2(1-33) | ε-Lys-17 | C16 | β-alanine | 4.4 ± 1.1 |
| L17K(4-(hexadecanoylamino)butanoyl)/K30R-GLP-2(1-33) | L17K/K30R-GLP-2(1-33) | ε-Lys-17 | C16 | GABA | 3.8 ± 0.6 |
| D3E/S7K((S)-4-carboxy-4-(hexadecanoylamino)butanoyl)/K30R/D33E-GLP-2(1-33) | D3E/S7K/K30R/D33E-GLP-2(1-33) | ε-Lys-7 | C16 | γ-glutamic acid | 280 |
| D3E/D8K((S)-4-carboxy-4-(hexadecanoylamino)butanoyl)/K30R/D33E-GLP-2(1-33) | D3E/D8K/K30R/D33E-GLP-2(1-33) | ε-Lys-8 | C16 | γ-glutamic acid | 31.9 |
| D3E/N11K((S)-4-carboxy-4-(hexadecanoylamino)butanoyl)/K30R/D33E-GLP-2(1-33) | D3E/N11K/K30R/D33E-GLP-2(1-33) | ε-Lys-11 | C16 | γ-glutamic acid | 53.1 |
| D3E/T12K((S)-4-carboxy-4-(hexadecanoylamino)butanoyl)/K30R/D33E-GLP-2(1-33) | D3E/T12K/K30R/D33E-GLP-2(1-33) | ε-Lys-12 | C16 | γ-glutamic acid | 29.4 |
| D3E/L17K((S)-4-carboxy-4-(hexadecanoylamino)butanoyl)/K30R/D33E-GLP-2(1-33) | D3E/L17K/K30R/D33E-GLP-2(1-33) | ε-Lys-17 | C16 | γ-glutamic acid | 16.2 |

Example 64

Pharmaceutical Formulations.

Buffer and obtionally a preservative, obtionally an isotonic agent, obtionally further additive(s) selected from chelating agent, stabiliser (e.g. imidazole or certain amino acids (charged-basic) such as histidine or arginine) and surfactant are dissolved and pH is adjusted to the specified pH. Hereafter the GLP-2 compound is dissolved under slow stirring. The pH is adjusted to the specified using Sodium Hydroxide and/or Hydrochloric Acid. Finally, the formulation is sterilised by filtration through a 0.22 μm sterile filter.

Physical stability of the formulations is evaluated by means of visual inspection and turbidity after storage of the formulation in top filled glass cartridges for various time periods. The cartridges are stored at 5° C.±3° C. and/or at elevated temperatures (e.g. 25° C. or 37° C.).

Visual inspection of the formulations is performed in a sharp focused light with a dark background. The turbidity of the formulation is characterized by a visual score ranking the degree of turbidity from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight.

The turbidity is also measured in Nephelometric Turbidity Units (NTU) with a nephelometer, which has been calibrated with a Formazin standard. A formulation with a turbidity>10 NTU is regarded as physical unstable.

GLP-2 compound concentrations are based on UV absorbance using $\epsilon_{280}$=5700 M$^{-1}$ cm$^{-1}$. Analytical HPLC. The contents of intact GLP-2 compound in samples is quantitated by reverse phase HPLC using a C4 column and standard TFA/MeCN gradient elution.

The GLP-2 formulation may be avaluated by Equilibrium Solubility; a GLP-2 compound is dissolved at a concentration of 2 mg/mL in the appropriate buffer and the solution is filtered through a 0.45 μm filter. From the stock solution samples are withdrawn, the pH is adjusted to the desired value, and the samples are incubated at 23° C. for 24 hours. After centrifugation (20,000 g in 20 min at 23° C.) of each sample, pH is measured and the solubility estimated from measurement of the absorbance (or HPLC analysis) of the supernatant.

The GLP-2 formulation may also be avaluated by Accelerated stability testing; 2 mg/mL GLP-2 compound samples are prepared in buffers a-d and transferred to 0.2 mL HPLC vials which are sealed leaving "no" air-liquid interphase. Following incubation at defined temperatures in the 4-45° C. range, the content of intact GLP-2 compound as a function of time is determined by HPLC analysis.

The GLP-2 formulation may also be avaluated by Physical stability; The fluorescent dye thioflavine T (ThT) binds to the beta structure constituent of amyloid protein. The resulting increase in fluorescence quantum yield of the bound dye is used to predict the tendency of a GLP-2 compound to fibrillate under a variety of solvent conditions. Briefly, the GLP-2 compound is dissolved under the conditions of interest, a trace of ThT is added, the solutions are placed in 96-well microtiter plates where the fluorescence is read as a function of time using a predefined regimen of temperature and shaking conditions to effect accelerated amyloid formation. The resulting fluorescence vs time data then predicts the relative tendency of the GLP-2 compound to fibrillate under a set of conditions.

The GLP-2 formulation may also be avaluated by Analytical ultracentrifugation; Sedimentation velocity experiments are performed at 23° C. with a Beckman Optima XL-A ultracentrifuge equipped for simultaneous data capture using both absorbance and interference optics.

The GLP-2 formulation may also be avaluated by Circular Dichroism Spectroscopy. Far- and near-UV CD spectra are recorded at room temperature using a Jasco J-715 spectropolarimeter calibrated with (+)-10-camphorsulfonic acid.

Example 65

Pharmaceutical Formulations of GLP-2 Derivatives.

Buffer and obtionally a preservative, obtionally an isotonic agent, obtionally further additive(s) selected from chelating agent, stabiliser (e.g. imidazole or certain amino acids (charged-basic) such as histidine or arginine) and surfactant are dissolved and pH is adjusted to the specified pH. Hereafter the GLP-2 derivative is dissolved under slow stirring. The pH is adjusted to the specified using Sodium Hydroxide and/or Hydrochloric Acid. Finally, the formulation is sterilised by filtration through a 0.22 μm sterile filter.

Physical stability of the formulations is evaluated by means of visual inspection and turbidity after storage of the formulation in top filled glass cartridges for various time periods. The cartridges are stored at 5° C.±3° C. and/or at elevated temperatures (e.g. 25° C. or 37° C.).

Visual inspection of the formulations is performed in a sharp focused light with a dark background. The turbidity of the formulation is characterized by a visual score ranking the degree of turbidity from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight.

The turbidity is also measured in Nephelometric Turbidity Units (NTU) with a nephelometer, which has been calibrated with a Formazin standard. A formulation with a turbidity>10 NTU is regarded as physical unstable.

GLP-2 derivative concentrations are based on UV absorbance using
$\epsilon_{280}$=5700 $M^{-1}$ $cm^{-1}$. Analytical HPLC. The contents of intact GLP-2 derivative in samples is quantitated by reverse phase HPLC using a C4 column and standard TFA/MeCN gradient elution.

The GLP-2 formulation may be avaluated by Equilibrium Solubility; a GLP-2 derivative is dissolved at a concentration of 2 mg/mL in the appropriate buffer and the solution is filtered through a 0.45 μm filter. From the stock solution samples are withdrawn, the pH is adjusted to the desired value, and the samples are incubated at 23° C. for 24 hours. After centrifugation (20,000 g in 20 min at 23° C.) of each sample, pH is measured and the solubility estimated from measurement of the absorbance (or HPLC analysis) of the supernatant.

The GLP-2 formulation may also be avaluated by Accelerated stability testing; 2 mg/mL GLP-2 derivative samples are prepared in buffers a-d and transferred to 0.2 mL HPLC vials which are sealed leaving "no" air-liquid interphase. Following incubation at defined temperatures in the 4-45° C. range, the content of intact GLP-2 derivative as a function of time is determined by HPLC analysis.

The GLP-2 formulation may also be avaluated by Physical stability; The fluorescent dye thioflavine T (ThT) binds to the beta structure constituent of amyloid protein. The resulting increase in fluorescence quantum yield of the bound dye is used to predict the tendency of a GLP-2 derivative to fibrillate under a variety of solvent conditions. Briefly, the GLP-2 derivative is dissolved under the conditions of interest, a trace of ThT is added, the solutions are placed in 96-well microtiter plates where the fluorescence is read as a function of time using a predefined regimen of temperature and shaking conditions to effect accelerated amyloid formation. The resulting fluorescence vs time data then predicts the relative tendency of the GLP-2 derivative to fibrillate under a set of conditions.

The GLP-2 formulation may also be avaluated by Analytical ultracentrifugation;

Sedimentation velocity experiments are performed at 23° C. with a Beckman Optima XL-A ultracentrifuge equipped for simultaneous data capture using both absorbance and interference optics.

The GLP-2 formulation may also be avaluated by Circular Dichroism Spectroscopy. Far- and near-UV CD spectra are recorded at room temperature using a Jasco J-715 spectropolarimeter calibrated with (+)-10-camphorsulfonic acid.

Example 66

Pharmaceutical Lyophilised Formulations.

When providing a lyophilised product, an essential feature relates to the properties of the lyophilised cake. It needs to have good properties as to its form and structure, i.e. it should not collapse in that such collapsed cakes can be hard or even impossible to dissolve (reconstitute) before use. Conversely, the physical structure of the lyophilised cake may not be too loosen and soft. Hence, pharmaceutical lyophilised formulations of GLP-2 and variants are produced using mannitol, sucrose (bulking agents), and glycylglycine (buffering agent) at the following final concentrations:

| | |
|---|---|
| GLP-2 and variants: | 0.1-100 mg/ml |
| Sucrose: | 10 mg/ml |
| Mannitol: | 37 mg/ml |
| Glycylglycine: | 1.32 mg/ml | pH is adjusted to 8.00±0.03 using 0.1 N NaOH/HCl.

The solutions are filled in appropriate vials and lyophilised using standard lyophilisation methods as described by Wang et al, International Journal of Pharmaceutics 203 (2000): 1-60 (see section 4, page 16 ff.). Reconstitution of the lyophililised formulation is performed using an appropriate amount of water.

We claim:

1. A peptide comprising the amino acid sequence of formula I:

His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-Arg-$X^{21}$-Phe-Ile-$X^{24}$-Trp-Leu-Ile-$X^{28}$-Thr-Arg-Ile-Thr-$X^{33}$   (formula I)

wherein $X^2$ is Ala, Val, or Gly; $X^3$ is Asp or Glu; $X^5$ is Ser or Lys; $X^7$ is Ser or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn or Lys; $X^{12}$ is Thr or Lys; $X^{13}$ is Ile or Lys; $X^{14}$ is Leu or Lys; $X^{15}$ is Asp or Lys; $X^{16}$ is Asn or Lys; $X^{17}$ Leu or Lys; $X^{18}$ is Ala or Lys; $X^{21}$ is Asp or Lys; $X^{24}$ is Asn or Lys; $X^{28}$ is Gln or Lys; $X^{33}$ is Asp, Glu, or Lys and at least one of $X^5$, $X^7$, $X^8$, $X^9$, $X^{10}$, $X^{11}$, $X^{12}$, $X^{13}$, $X^{14}$, $X^{15}$, $X^{16}$, $X^{17}$, and $X^{18}$, $X^{21}$, $X^{24}$, $X^{28}$, $X^{33}$ is a Lys.

2. The peptide of claim 1, wherein the peptide consists essentially of an amino acid sequence:

His-$X^2$-$X^3$-Gly-$X^5$-Phe-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-Ala-Arg-$X^{21}$-Phe-Ile-$X^{24}$-Trp-Leu-Ile-$X^{28}$-Thr-Arg-Ile-Thr-$X^{33}$   (formula II)

wherein $X^2$ is Ala, Val, or Gly; $X^3$ is Asp or Glu; $X^5$ is Ser or Lys; $X^7$ is Ser or Lys; $X^8$ is Asp, Glu, or Lys; $X^9$ is Asp, Glu, or Lys; $X^{10}$ is Met, Lys, Leu, Ile, or Nor-Leucine; $X^{11}$ is Asn or Lys; $X^{12}$ is Thr or Lys; $X^{13}$ is Ile or Lys; $X^{14}$ is Leu or Lys; X¹⁵ is Asp or Lys; X¹⁶ is Asn or Lys; X¹⁷ is Leu or Lys; X¹⁸ is Ala or Lys; X²¹ is Asp or Lys; X²⁴ is Asn or Lys; X²⁸ is Gln or Lys; X³³ is Asp, Glu, or Lys and at least one of X⁵, X⁷, X⁸, X⁹, X¹⁰, X¹¹, X¹², X¹³, X¹⁴, X¹⁵, X¹⁶, X¹⁷, X¹⁸, X²¹, X²⁴, X²⁸, and X³³ is a Lys.

3. The peptide of claim 1, wherein the peptide consists of an amino acid sequence:

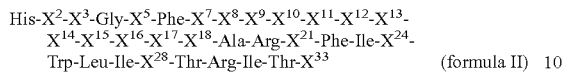

His-X²-X³-Gly-X⁵-Phe-X⁷-X⁸-X⁹-X¹⁰-X¹¹-X¹²-X¹³-X¹⁴-X¹⁵-X¹⁶-X¹⁷-X¹⁸-Ala-Arg-X²¹-Phe-Ile-X²⁴-Trp-Leu-Ile-X²⁸-Thr-Arg-Ile-Thr-X³³    (formula II)

wherein X² is Ala, Val, or Gly; X³ is Asp or Glu; X⁵ is Ser or Lys; X⁷ is Ser or Lys; X⁸ is Asp, Glu, or Lys; X⁹ is Asp, Glu, or Lys; X¹⁰ is Met, Lys, Leu, Ile, or Nor-Leucine; X¹¹ is Asn or Lys; X¹² is Thr or Lys; X¹³ is Ile or Lys; X¹⁴ is Leu or Lys; X¹⁵ is Asp or Lys; X¹⁶ is Asn or Lys; X¹⁷ is Leu or Lys; X¹⁸ is Ala or Lys; X²¹ is Asp, or Lys; X²⁴ is Asn, or Lys, X²⁸ is Gln, or Lys; X³³ is Asp, Glu, or Lys and at least one of X⁵, X⁷, X⁸, X⁹, X¹⁰, X¹¹, X¹², X¹³, X¹⁴, X¹⁵, X¹⁶, X¹⁷, X¹⁸, X²¹, X²⁴, X²⁸, and X³³ is a Lys.

4. The peptide of claim 1, wherein the amino acid sequence of formula I is characterized by at least one of the following X² is Ala or Gly; X⁵ is Ser; X⁷ is Ser; X⁸ is Asp or Glu; X⁹ is Asp or Glu; X¹⁰ is selected from the group consisting of Met, Leu, Ile, and Nor-Leucine; X¹¹ is Asn; X¹² is Thr; X¹³ is Ile; X¹⁴ is Leu; X¹⁵ is Asp; X¹⁶ is Asn; X¹⁷ is Leu; X¹⁸ is Ala; X²¹ is Asp; X²⁴ is Asn; X²⁸ is Gln; and X³³ is Asp or Glu.

5. The peptide of claim 2, wherein the amino acid sequence of formula II is characterized by at least one of the following X² is Ala or Gly; X⁵ is Ser; X⁷ is Ser; X⁸ is Asp or Glu; X⁹ is Asp or Glu; X¹⁰ is selected from the group consisting of Met, Leu, Ile, and Nor-Leucine; X¹¹ is Asn; X¹² is Thr; X¹³ is Ile; X¹⁴ is Leu; X¹⁵ is Asp; X¹⁶ is Asn; X¹⁷ is Leu; X¹⁸ is Ala; X²¹ is Asp; X²⁴ is Asn; X²⁸ is Gln; and X³³ is Asp or Glu.

6. The peptide of claim 3, wherein the amino acid sequence of formula II is characterized by at least one of the following X² is Ala or Gly; X⁵ is Ser; X⁷ is Ser; X⁸ is Asp or Glu; X⁹ is Asp or Glu; X¹⁰ is selected from the group consisting of Met, Leu, Ile, and Nor-Leucine; X¹¹ is Asn; X¹² is Thr; X¹³ is Ile; X¹⁴ is Leu; X¹⁵ is Asp; X¹⁶ is Asn; X¹⁷ is Leu; X¹⁸ is Ala; X²¹ is Asp; X²⁴ is Asn; X²⁸ is Gln; and X³³ is Asp or Glu.

7. The peptide of claim 4, wherein X² is Ala.
8. The peptide of claim 4, wherein X² is Gly.
9. The peptide of claim 4, wherein X³ is Asp.
10. The peptide of claim 4, wherein X³ is Glu.
11. The peptide of claim 4, wherein X⁵ is Ser.
12. The peptide of claim 4, wherein X⁷ is Ser.
13. The peptide of claim 4, wherein X⁸ is Asp.
14. The peptide of claim 4, wherein X⁸ is Glu.
15. The peptide of claim 4, wherein X⁹ is Asp.
16. The peptide of claim 4, wherein X⁹ is Glu.
17. The peptide of claim 4, wherein X¹⁰ is selected from the group consisting of Met, Leu, Ile, and Nor-Leucine.
18. The peptide of claim 4, wherein X¹¹ is Asn.
19. The peptide of claim 4, wherein X¹² is Thr.
20. The peptide of claim 4, wherein X¹³ is Ile.
21. The peptide of claim 4, wherein X¹⁴ is Leu.
22. The peptide of claim 4, wherein X¹⁵ is Asp.
23. The peptide of claim 4, wherein X¹⁶ is Asn.
24. The peptide of claim 4, wherein X¹⁷ is Leu.
25. The peptide of claim 4, wherein X¹⁸ is Ala.
26. The peptide of claim 4, wherein X²¹ is Asp.
27. The peptide of claim 4, wherein X²⁴ is Asn.
28. The peptide of claim 4, wherein X²⁸ is Gln.
29. The peptide of claim 4, wherein X³³ is Asp.
30. The peptide of claim 4, wherein X³³ is Glu.
31. The peptide of claim 1, wherein the peptide is selected from the group consisting of: S5K/K30R-GLP-2(1-33); S7K/K30R-GLP-2(1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); I13K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/I13K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); and D3E/Q28K/K30R/D33E-GLP-2(1-33).

* * * * *

SEQUENCE LISTING

<160> NUMBER OF SEQ ID NOS: 3

<210> SEQ ID NO 1
<211> LENGTH: 33
<212> TYPE: PRT
<213> ORGANISM: Human

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: xaa=Ala, Val or Gly
<220> FEATURE:
<221> NAME/KEY: MISC_FEATURE
<222> LOCATION: (3)..(3)
<223> OTHER INFORMATION: xaa=Asp or Glu
<220> FEATURE:
<221> NAME/KEY: MISC_FEATURE
<222> LOCATION: (5)..(5)
<223> OTHER INFORMATION: xaa=Ser or Lys
<220> FEATURE:
<221> NAME/KEY: MISC_FEATURE
<222> LOCATION: (7)..(7)
<223> OTHER INFORMATION: xaa=Ser or Lys
<220> FEATURE:
<221> NAME/KEY: MISC_FEATURE
<222> LOCATION: (8)..(8)
<223> OTHER INFORMATION: xaa=Asp or Glu
<220> FEATURE:
<221> NAME/KEY: MISC_FEATURE
<222> LOCATION: (9)..(9)
<223> OTHER INFORMATION: xaa=Asp, Glu or Lys
<220> FEATURE:
<221> NAME/KEY: MISC_FEATURE
<222> LOCATION: (10)..(10)
<223> OTHER INFORMATION: xaa=Met, Lys, Leu, Ile or Nor-Leucine
<220> FEATURE:
<221> NAME/KEY: MISC_FEATURE
<222> LOCATION: (11)..(11)
<223> OTHER INFORMATION: xaa=Asn or Lys
<220> FEATURE:
<221> NAME/KEY: MISC_FEATURE
<222> LOCATION: (12)..(12)
<223> OTHER INFORMATION: xaa=Thr or Lys
<220> FEATURE:
<221> NAME/KEY: MISC_FEATURE
<222> LOCATION: (13)..(13)
<223> OTHER INFORMATION: xaa=Ile or Lys
<220> FEATURE:
<221> NAME/KEY: MISC_FEATURE
<222> LOCATION: (14)..(14)
<223> OTHER INFORMATION: xaa=Leu or Lys
<220> FEATURE:
<221> NAME/KEY: MISC_FEATURE
<222> LOCATION: (14)..(14)
<223> OTHER INFORMATION: xaa=Leu or Lys
<220> FEATURE:
<221> NAME/KEY: MISC_FEATURE
<222> LOCATION: (15)..(15)
<223> OTHER INFORMATION: xaa=Asp or Lys

```
<220> FEATURE:
<221> NAME/KEY: MISC_FEATURE
<222> LOCATION: (16)..(16)
<223> OTHER INFORMATION: xaa=Asn or Lys
<220> FEATURE:
<221> NAME/KEY: MISC_FEATURE
<222> LOCATION: (17)..(17)
<223> OTHER INFORMATION: xaa=Leu or Lys
<220> FEATURE:
<221> NAME/KEY: MISC_FEATURE
<222> LOCATION: (18)..(18)
<223> OTHER INFORMATION: xaa=Ala or Lys
<220> FEATURE:
<221> NAME/KEY: MISC_FEATURE
<222> LOCATION: (21)..(21)
<223> OTHER INFORMATION: xaa=Asp or Lys
<220> FEATURE:
<221> NAME/KEY: MISC_FEATURE
<222> LOCATION: (24)..(24)
<223> OTHER INFORMATION: xaa=Asn or Lys
<220> FEATURE:
<221> NAME/KEY: MISC_FEATURE
<222> LOCATION: (28)..(28)
<223> OTHER INFORMATION: xaa=Gln or Lys
<220> FEATURE:
<221> NAME/KEY: MISC_FEATURE
<222> LOCATION: (33)..(33)
<223> OTHER INFORMATION: xaa=Asp, Glu or Lys

<400> SEQUENCE: 2

His Xaa Xaa Gly Xaa Phe Xaa Xaa Xaa Xaa Xaa Xaa Xaa Xaa Xaa
 1               5                  10                  15

Xaa Xaa Ala Arg Xaa Phe Ile Xaa Trp Leu Ile Xaa Thr Arg Ile Thr
             20                  25                  30

Xaa

<210> SEQ ID NO 3
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: xaa=Ala, Val or Gly
<220> FEATURE:
<221> NAME/KEY: MISC_FEATURE
<222> LOCATION: (3)..(3)
<223> OTHER INFORMATION: xaa=Asp or Glu
<220> FEATURE:
<221> NAME/KEY: MISC_FEATURE
<222> LOCATION: (5)..(5)
<223> OTHER INFORMATION: xaa=Ser or Lys
<220> FEATURE:
<221> NAME/KEY: MISC_FEATURE
<222> LOCATION: (7)..(7)
<223> OTHER INFORMATION: xaa=Ser or Lys
<220> FEATURE:
<221> NAME/KEY: MISC_FEATURE
<222> LOCATION: (8)..(8)
<223> OTHER INFORMATION: xaa=Asp, Glu or Lys
<220> FEATURE:
<221> NAME/KEY: MISC_FEATURE
<222> LOCATION: (9)..(9)
<223> OTHER INFORMATION: xaa=Asp, Glu or Lys
<220> FEATURE:
<221> NAME/KEY: MISC_FEATURE
<222> LOCATION: (10)..(10)
<223> OTHER INFORMATION: xaa=Met, Lys, Leu, Ile or Nor-Leucine
<220> FEATURE:
<221> NAME/KEY: MISC_FEATURE
<222> LOCATION: (11)..(11)
<223> OTHER INFORMATION: xaa=Asn or Lys
<220> FEATURE:
```

```
<221> NAME/KEY: MISC_FEATURE
<222> LOCATION: (12)..(12)
<223> OTHER INFORMATION: xaa=Thr or Lys
<220> FEATURE:
<221> NAME/KEY: MISC_FEATURE
<222> LOCATION: (13)..(13)
<223> OTHER INFORMATION: xaa=Ile or Lys
<220> FEATURE:
<221> NAME/KEY: MISC_FEATURE
<222> LOCATION: (14)..(14)
<223> OTHER INFORMATION: xaa=Leu or Lys
<220> FEATURE:
<221> NAME/KEY: MISC_FEATURE
<222> LOCATION: (15)..(15)
<223> OTHER INFORMATION: xaa=Asp or Lys
<220> FEATURE:
<221> NAME/KEY: MISC_FEATURE
<222> LOCATION: (16)..(16)
<223> OTHER INFORMATION: xaa=Asn or Lys
<220> FEATURE:
<221> NAME/KEY: MISC_FEATURE
<222> LOCATION: (17)..(17)
<223> OTHER INFORMATION: xaa=Leu or Lys
<220> FEATURE:
<221> NAME/KEY: MISC_FEATURE
<222> LOCATION: (18)..(18)
<223> OTHER INFORMATION: xaa=Ala or Lys
<220> FEATURE:
<221> NAME/KEY: MISC_FEATURE
<222> LOCATION: (20)..(20)
<223> OTHER INFORMATION: xaa=Arg or Lys
<220> FEATURE:
<221> NAME/KEY: MISC_FEATURE
<222> LOCATION: (21)..(21)
<223> OTHER INFORMATION: xaa=Asp or Lys
<220> FEATURE:
<221> NAME/KEY: MISC_FEATURE
<222> LOCATION: (24)..(24)
<223> OTHER INFORMATION: xaa=Asn or Lys
<220> FEATURE:
<221> NAME/KEY: MISC_FEATURE
<222> LOCATION: (28)..(28)
<223> OTHER INFORMATION: xaa=Gln or Lys
<220> FEATURE:
<221> NAME/KEY: MISC_FEATURE
<222> LOCATION: (30)..(30)
<223> OTHER INFORMATION: xaa=Arg or Lys
<220> FEATURE:
<221> NAME/KEY: MISC_FEATURE
<222> LOCATION: (33)..(33)
<223> OTHER INFORMATION: xaa=Asp, Glu or Lys

<400> SEQUENCE: 3

His Xaa Xaa Gly Xaa Phe Xaa Xaa Xaa Xaa Xaa Xaa Xaa Xaa Xaa
1               5                   10                  15

Xaa Xaa Ala Xaa Xaa Phe Ile Xaa Trp Leu Ile Xaa Thr Xaa Ile Thr
            20                  25                  30

Xaa
```